United States Patent
Bhatnagar

(10) Patent No.: US 12,325,760 B2
(45) Date of Patent: *Jun. 10, 2025

(54) INHIBITORS OF NF KAPPA-B ACTIVITY FOR TREATMENT OF DISEASES AND DISORDERS

(71) Applicant: Rajendra Sahai Bhatnagar, Burlingame, CA (US)

(72) Inventor: Rajendra Sahai Bhatnagar, Burlingame, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/453,807

(22) Filed: Aug. 22, 2023

(65) Prior Publication Data

US 2024/0083941 A1    Mar. 14, 2024

Related U.S. Application Data

(60) Division of application No. 17/505,544, filed on Oct. 19, 2021, now Pat. No. 11,773,135, which is a division of application No. 15/982,837, filed on May 17, 2018, now Pat. No. 11,174,286, which is a continuation of application No. 14/866,040, filed on Sep. 25, 2015, now Pat. No. 10,030,048.

(60) Provisional application No. 62/055,982, filed on Sep. 26, 2014.

(51) Int. Cl.
| | |
|---|---|
| C07K 5/10 | (2006.01) |
| C07K 5/083 | (2006.01) |
| C07K 7/06 | (2006.01) |
| A61K 38/00 | (2006.01) |

(52) U.S. Cl.
CPC ............ *C07K 5/10* (2013.01); *C07K 5/0806* (2013.01); *C07K 7/06* (2013.01); *A61K 38/00* (2013.01)

(58) Field of Classification Search
CPC .......... C07K 5/10; C07K 7/06; C07K 5/0806; A61K 38/00; A61P 43/00; A61P 29/00; A61P 25/04; A61P 17/00
See application file for complete search history.

(56) References Cited

U.S. PATENT DOCUMENTS

| | | |
|---|---|---|
| 5,354,736 A | 10/1994 | Bhatnagar |
| 5,635,482 A | 6/1997 | Bhatnagar |
| 5,661,127 A | 8/1997 | Bhatnagar et al. |
| 5,674,848 A | 10/1997 | Bhatnagar |
| 5,707,632 A | 1/1998 | Williams et al. |
| 5,780,436 A | 7/1998 | Bhatnagar et al. |
| 5,958,428 A | 9/1999 | Bhatnagar |
| 6,268,348 B1 | 7/2001 | Bhatnagar |
| 6,489,165 B2 | 12/2002 | Bhatnagar et al. |
| 6,509,318 B1 | 1/2003 | Bhatnagar et al. |
| 6,638,912 B2 | 10/2003 | Bhatnagar et al. |
| 6,818,620 B2 | 11/2004 | Bhatnagar |
| 6,864,355 B1 | 3/2005 | May et al. |
| 7,199,103 B2 | 4/2007 | Bhatnagar |
| 8,211,858 B2 | 7/2012 | Jankun et al. |
| 8,507,436 B2 | 8/2013 | Higazi |
| 9,943,566 B2 | 4/2018 | Brooks et al. |
| 10,030,048 B2 | 7/2018 | Bhatnagar |
| 11,174,286 B2 | 11/2021 | Bhatnagar |
| 11,773,135 B2 * | 10/2023 | Bhatnagar ............... A61P 43/00 514/1.9 |
| 2002/0010134 A1 | 1/2002 | Bhatnagar |
| 2003/0077825 A1 | 4/2003 | Bhatnagar et al. |
| 2003/0083265 A1 | 5/2003 | Bhatnagar |
| 2005/0100533 A1 | 5/2005 | Bhatnagar et al. |
| 2006/0211075 A1 | 9/2006 | Lawrence |
| 2006/0293227 A1 | 12/2006 | Bhatnagar |
| 2006/0293228 A1 | 12/2006 | Bhatnagar |
| 2007/0009568 A1 | 1/2007 | Bhatnagar |
| 2007/0032411 A1 | 2/2007 | Wilks |
| 2008/0274102 A1 | 11/2008 | Wallach |
| 2009/0092582 A1 | 4/2009 | Bogin et al. |
| 2010/0184667 A1 | 7/2010 | Jankun et al. |
| 2010/0215636 A1 | 8/2010 | Higazi |
| 2011/0015138 A1 | 1/2011 | Kufe et al. |
| 2011/0150828 A1 | 6/2011 | Galipeau et al. |
| 2011/0178273 A1 | 7/2011 | Aabersold et al. |
| 2012/0064099 A1 | 3/2012 | Landry |
| 2013/0190236 A1 | 7/2013 | Patterson |
| 2016/0000682 A1 | 1/2016 | Brooks et al. |
| 2016/0151270 A1 | 6/2016 | Brooks et al. |
| 2017/0051012 A1 | 2/2017 | Bhatnagar |
| 2018/0298055 A1 | 10/2018 | Bhatnagar |
| 2022/0133837 A1 | 5/2022 | Bhatnagar |

(Continued)

FOREIGN PATENT DOCUMENTS

| | | |
|---|---|---|
| CN | 1233171 A | 10/1999 |
| CN | 1379772 A | 11/2002 |
| CN | 103223175 A | 7/2013 |

(Continued)

OTHER PUBLICATIONS

Calzado et al [Curr.Med.Chem., 2007, 14(3), 367-76] (Year: 2007).*
Baima, E.T. et al. (Apr. 30, 2010). "Novel Insights Into the Cellular Mechanisms of the Anti-inflammatory Effects of NF-κB Essential Modulator Binding Domain Peptides," The J. Biological Chemistry 285(18):13498-13506.
Baud, V. et al. (Jan. 2009). Is NF-κB a Good Target for Cancer Therapy? Hopes and Pitfalls Nature Reviews 8:33-40.
Betts, M.J. et al. (2003). "Amino Acid Properties and Consequences of Substitutions," Chapter 13 in Bioinformatics for Geneticists, by M.R.Barnes et al., John Wiley & Sons Ltd., pp. 289-316.
Bowen, J. M. et al. (2008). "New Pathways for Alimentary Mucositis" Journal of Oncology (7 pages).

(Continued)

*Primary Examiner* — Sudhakar Katakam
(74) *Attorney, Agent, or Firm* — MORRISON & FOERSTER LLP

(57) ABSTRACT

Peptides and methods of use thereof, are disclosed for use in treating various diseases and disorders, including inflammation, pain, oral mucositis, oral lesions, and cancer. The peptides modulate the activity of the transcription factor NF κB.

21 Claims, 17 Drawing Sheets

Specification includes a Sequence Listing.

(56) References Cited

U.S. PATENT DOCUMENTS

2024/0180997 A1      6/2024   Bhatnagar

FOREIGN PATENT DOCUMENTS

| | | |
|---|---|---|
| JP | 2013176368 A | 9/2013 |
| WO | 199102537 A1 | 3/1991 |
| WO | 199311781 A1 | 6/1993 |
| WO | 199516709 A2 | 6/1995 |
| WO | 200182773 A2 | 11/2001 |
| WO | 200226935 A2 | 4/2002 |
| WO | 2006133027 A2 | 12/2006 |
| WO | 2007002469 A2 | 1/2007 |
| WO | 2007002594 A1 | 1/2007 |
| WO | 2016003505 A1 | 1/2016 |
| WO | 2016049580 A2 | 3/2016 |

OTHER PUBLICATIONS

European Extended Search Report mailed on Apr. 6, 2020 for EP Application No. 15844064.4 filed on Apr. 13, 2017, 5 pages.
European Extended Search Report mailed on Jul. 19, 2018 for EP Application No. 15844064.4 filed on Apr. 13, 2017, 2 pages.
European Supplementary Search Report mailed on May 23, 2018 for EP Application No. 15844064.4 filed on Apr. 13, 2017, 2 pages.
Gilmore, T.D. et al. (Oct. 30, 2006). "Inhibitors of NF-κB Signaling: 785 and Counting," Oncogene 25 (51):6887-6899.
Gupta, S.C. et al. (Oct. 1, 2010; e-published on May 21, 2010). "Inhibiting NF-κB Activation by Small Molecules as a Therapeutic Strategy," Biochimica et Biophysica Acta 1799(10-12):775-787.
International Search Report mailed on Mar. 4, 2016, for PCT Application No. PCT/US2015/052467, 5 pages.
Kang, Y. et al. (Nov. 1996). "Identification and Cloning of a Novel Type I Serine/Threonine Kinase Receptor of the TGF-beta/BMP Superfamily in Rat Prostate," Biochemistry and Molecular Biology International 40(5):993-1001.
Kavitha, K. et al. (Jul. 2014; e-published on Feb. 27, 2014). "Cytomodulin-1, A Synthetic Peptide Abrogates Oncogenic Signaling Pathways to Impede Invasion and Angiogenesis in the Hamster Cheek Pouch Carcinogenesis Model," Biochimie 102:56-67.
Kudrimoti, M. et al. (2016, e-pub. Oct. 13, 2016). "Dusquetide: A Novel Innate Defense Regulator Demonstrating A Significant and Consistent Reduction in the Duration of Oral Mucositis in Preclinical Data and a Randomized, Placebo-Controlled Phase 2a Clinical Study," Journal of Biotechnology, 239:115-125.
Lam, H.J. et al. (2004) "Synthetic Peptides Cytomodulin-1 (Cm-1) And Cytomodulin-2 (Cm-2) Promote Collagen Synthesis And Wound Healing In Vitro," Proceedings Of The 26 Annual International Conference Of The Ieee Embs, San Francisco, CA , USA, Sep. 1-5, 2004, 5028-5030, 3 Pages.
Lin, L. et al. (2012). "Tissue Plasminogen Activator Activates NF-κB Through a Pathway Involving Annexin A2/CD11b and Intergrin-Linked Kinase" J Am Soc Nephrol 23:1329-1338, 13 pages.
Liu, S.F. et al. (2006), "Nf- κb Activation as a Pathological Mechanism of Septic Shock and Inflammation," Am J. Physiol, 290:L622-L645.
NCBI Blast. (Aug. 10, 2017). BLAST search of YMAPEV retrieved from https://blast.ncbi.nlm.nih.gov/Blast.cgi, 7 pages.
Niederberger, E. et al. (Oct. 2008). "The IKK-NF-κB Pathway: A Source for Novel Molecular Drug Targets in Pain Therapy?" The FASEB Journal 22:3432-3442.
Olive, M. F. et al. (2015). Prescription Pain Relievers, Understanding Drugs, Infobase Publishing, p. 110, one page.
Record, C.J. et al. (2010), "Structural Comparison of Human Mammalian Ste-20-Like Kinases", PLoS ONE, 5(8): e11905, 11 pages.
Thundimadathil, J. et al. (Mar./Apr. 2014). "Improving Stability of Peptide Drugs Through Chemical Modifications," Oligos & Peptides—Chimica Oggi—Chemistry Today 32(2):35-38.
Written Opinion mailed on Mar. 4, 2016, for PCT Application No. PCT/US2015/052467, 10 pages.
Fujii, N. (2005). "Damage and Aging of Skin Proteins Caused by Solar Ultraviolet Rays Assessed by D-Amino Acids," Torike University Nuclear Reactor Research Institute, Cosmetology 13:P29-P32, 6 pages. (Translation of the Abstract Only).

* cited by examiner

| SEQ ID NO. | PEPTIDE SEQUENCE | PERCENT INHIBITION |
|---|---|---|
| 001 | YMAPEV | 55 |
| 002 | IIAPEG | 60 |
| 003 | EIAEAL | 72 |
| 004 | SNVAEA | 70 |
| 005 | ANIAEA | 57 |
| 006 | ANMAEN | 85 |
| 007 | NWAENA | 55 |
| 008 | LWAEAK | 50 |
| 009 | LIAEAK | 65 |
| 010 | NVAENA | 56 |
| 011 | LVAEAH | 45 |
| 012 | LIANAK | 73 |
| 013 | LFAP[D]EA | 87 |
| 014 | LIAP[D]EA | 35 |

| SAMPLE | FIREFLY LUCIFERASE READING | RENELLA LUCIFERASE READING | RATIO |
|---|---|---|---|
| CONTROL | 0.295 | 0.118 | 3.321 |
| TNFα | 0.969 | 0.069 | 13.96 |
| LFAP[D]EA (SEQ ID NO: 13) | 0.000 | 0.081 | 0.000 |
| TNF a + LFAP[D]EA (SEQ ID NO: 13) | 0.058 | 0.076 | 0.768 |

Western blot for p65 (NFκB) activation and inhibition in SiHa cells

Peptide NP-1 SEQ ID NO: 008 LWAEAK
Peptide NP-2 SEQ ID NO: 015 TNWAEN
Peptide NP-3 SEQ ID NO: 016 TWAPES
Peptide NP-4 SEQ ID NO: 017 TWSPEL

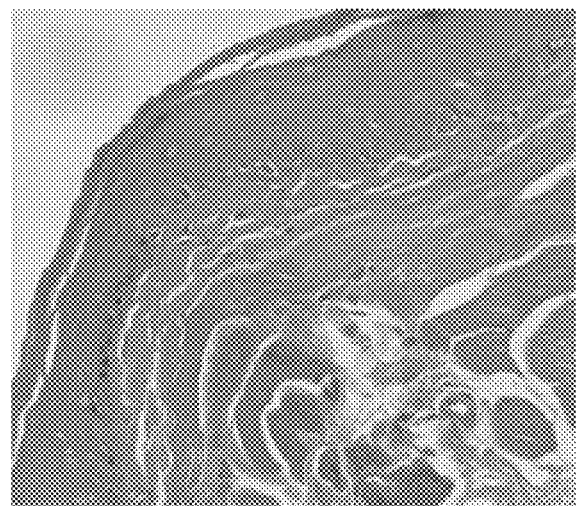
FIG. 6A  Untreated Control
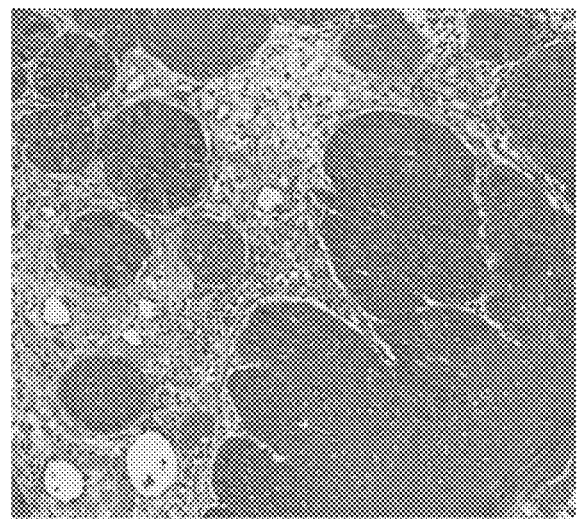
FIG. 6B  DMBA Treated
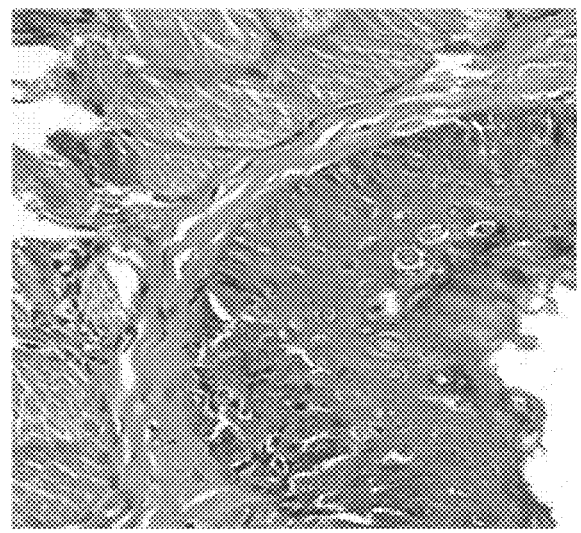
FIG. 6C  DMBA Treated then Treated with Peptide

| | |
|---|---|
| AGER | advanced glycosylation end product-specific receptor |
| ALOX12B | arachidonate 12-lipoxygenase, 12R type |
| APOC3 | apolipoprotein C-III |
| BCL2 | B-cell CLL/lymphoma 2 |
| BCL2A1 | BCL2-related protein A1 |
| BCL2L1 | BCL2-like 1 |
| BCL3 | B-cell CLL/lymphoma 3 |
| BDKRB1 | bradykinin receptor B |
| BLR1 | Burkitt lymphoma receptor 1, GTP binding protein (chemokine (C-X-C motif) receptor 5 CXCR5) |
| BM2 | beta-2-microglobulin |
| CARD15 | caspase recruitment domain family, member 15 (Nod2) |
| CCL11 | chemokine (C-C motif) ligand 11 |
| CCL15 | chemokine (C-C motif) ligand 15 (MIP-3alpha) |
| CCL2 | chemokine (C-C motif) ligand 2 (MCP1/JE) |
| CCL5 | chemokine (C-C motif) ligand 5 (RANTES) |
| CCND1 | cyclin D1 (PRAD1: parathyroid adenomatosis 1) |
| CCR5 | chemokine (C-C motif) receptor 5 |
| CCR7 | chemokine (C-C motif) receptor 7 |
| CD105 | endoglin (Osler-Rendu-Weber syndrome 1) (ENG) |
| CD209 | antigen (DC-SIGN) |
| CD3G | T-cell receptor/CD3gamma, CD3G antigen, gamma polypeptide (TiT3 complex) |
| CD44 | CD44 antigen (homing function and Indian blood group system) |
| CD48 | CD48 antigen (B-cell membrane protein) |
| CD69 | CD69 antigen (p60, early T-cell activation antigen) |
| CD74 | CD74 antigen (invariant polypeptide of major histocompatibility complex, class II antigen-associated) |
| CD80 | CD80 antigen (CD28 antigen ligand 1, B7-1 antigen) |
| CD83 | CD83 antigen (activated B lymphocytes, immunoglobulin superfamily) |
| CR2 | complement receptor 2 : complement component (3d/Epstein Barr virus) receptor 2 |
| CRP | C-reactive protein, pentraxin-related |
| CSF1 | colony stimulating factor 1 (macrophage) (M-CSF) |
| CSF2 | colony stimulating factor 2 (granulocyte-macrophage) (IGM-CSF) |
| CSF3 | colony stimulating factor 3 (granulocyte) (G-CSF) |
| CXCL5 | Neutrophil activating peptide-78, chemokine (C-X-C motif) ligand 5 |
| DEFB4 | defensing, beta 4 |
| ELF3 | E74-like factor 3 (ets domain transcription factor,epithelial-specific ) (ESE-1) |

*FIG. 7*

| | |
|---|---|
| F3 | coagulation factor III (thromboplastin, tissue factor) |
| GSTP1 | glutathione S-transferase pi |
| HC3 | proteasome subunit alpha-type 2 (PSMA2) |
| HMOX1 | heme oxygenase (decycling) 1 |
| ICAM1 | intercellular adhesion molecule 1 (CD54), human rhinovirus receptor |
| IER3 | immediate early response 3 (IEX-1L) |
| IFNB1 | interferon, beta 1, fibroblast |
| IGHG3 | immunoglobulin heavy constant gamma 3 (G3m marker) |
| IGHG4 | immunoglobulin heavy constant gamma 4 (G4m marker) |
| IL11 | interleukin 11 |
| IL13 | interleukin 13 |
| IL15 | interleukin 15 |
| IL15RA | interleukin 15 receptor, alpha |
| IL1A | interleukin 1, alpha |
| IL1B | interleukin 1, beta |
| IL1RN | interleukin 1 receptor antagonist |
| IL2 | interleukin 2 |
| IL2RA | IL-2 receptor alpha chain interleukin 2 receptor, alpha chain |
| IL6 | interleukin 6 (interferon, beta 2) |
| IL8 | interleukin 8 |
| IL9 | interleukin 9 |
| IRF1 | interferon regulatory factor 1 |
| IRF2 | interferon regulatory factor 2 |
| IRF4 | interferon regulatory factor 4 |
| IRF7 | interferon regulatory factor 7 |
| KLK3 | kallikrein 3, (prostate specific antigen) |
| LMP2 | proteasome (prosome, macropain) subunit, beta type, 9 (large multifunctional protease 2) (PSMB9) |
| LTA | lymphotoxin alpha (TNF superfamily, member 1) |
| LTB | lymphotoxin beta (TNF superfamily, member 3) |
| MMP9 | matrix metalloproteinase 9 (gelatinase B, 92kDa gelatinase, 92kDa type IV collagenase) |
| MYC | v-myc myelocytomatosis viral oncogene homolog (avian) |
| NFKB1 | nuclear factor of kappa light polypeptide gene enhancer in B-cells 1 (p105) |
| NFKB2 | nuclear factor of kappa light polypeptide gene enhancer in B-cells 2 (p49/p100) |
| NFKBIA | nuclear factor of kappa light polypeptide gene enhancer in B-cells inhibitor, alpha |
| NOS2A | nitric oxide synthase 2A (inducible, hepatocytes) |
| NQO1 | NAD(P)H dehydrogenase, quinone 1 |
| NR4A2 | nuclear receptor subfamily 4, group A, member 2 (NURR1) |

*FIG. 7 (cont.)*

| | |
|---|---|
| OPRM1 | opioid receptor, mu 1 |
| PDGFB | platelet-derived growth factor beta polypeptide (simian sarcoma viral (v-sis) oncogene homolog) |
| PLAU | urokinase-type plasminogen activator |
| PLCD1 | phospholipase C, delta 1 |
| PTAFR | platelet-activating factor receptor |
| PTGS2 | prostaglandin-endoperoxide synthase 2 (prostaglandin G/H synthase and cyclooxygenase) (COX-2) |
| PTX3 | pentaxin-related gene, rapidly induced by IL-1 beta |
| RELB | v-rel reticuloendotheliosis viral oncogene homolog B, nuclear factor of kappa light polypeptide gene enhancer in B-cells 3 (avian) |
| S100A6 | S100 calcium binding protein A6 (calcyclin) |
| SCNN1A | Amiloride-sensitive sodium channel, nonvoltage-gated 1 alpha |
| SELE | selectin E (endothelial adhesion molecule 1) ELAM1 |
| SELP | selectin P (granule membrane protein 140kDa, antigen CD62) |
| SLC2A5 | solute carrier family 2 (facilitated glucose/fructose transporter), member 5 (GLUT5) |
| SOD2 | MnSOD, superoxide dismutase 2, mitochondrial |
| STAT5A | signal transducer and activator of transcription 5A |
| TACR1 | tachykinin receptor 1, neurokinin 1 receptor (NK-1R) |
| TAP1 | transporter 1, ATP-binding cassette, sub-family B (MDR/TAP) |
| TFPI2 | tissue factor pathway inhibitor 2 |
| TGM2 | transglutaminase 2 (C polypeptide, protein-glutaminegamma-glutamyltransferase) |
| TNC | tenascin C (hexabrachion) |
| TNF | tumor necrosis factor (TNF superfamily, member 2) TNF alpha |
| TNFAIP3 | tumor necrosis factor, alpha-induced protein 3 (A20) |
| TNFRSF5 | tumor necrosis factor receptor superfamily, member 5 (CD40) |
| TNFRSF6 | tumor necrosis factor receptor superfamily, member 6 (cCD95 Fas) |
| TNFRSF9 | tumor necrosis factor receptor superfamily, member 9 (CD137) |
| TNFSF5 | t CD40L tumor necrosis factor (ligand) superfamily, member 5 (hyper-IgM syndrome) |
| TNFSF6 | tumor necrosis factor (fas ligand) superfamily, member 6 |
| TP53 | tumor protein p53 (Li-Fraumeni syndrome) |
| TPMT | thiopurine S-methyltransferase |
| VCAM1 | vascular cell adhesion molecule 1 |
| VEGF C | vascular endothelial growth factor C |
| VIM | vimentin |

*FIG. 7 (cont.)*

| SEQ ID NO. | SEQUENCE |
|---|---|
| 001 | YMAPEV |
| 002 | IIAPEG |
| 003 | EIAEAL |
| 004 | SNVAEA |
| 005 | ANIAEA |
| 006 | ANMAEN |
| 007 | NWAENA |
| 008 | LWAEAK |
| 009 | LIAEAK |
| 010 | NVAENA |
| 011 | LVAEAH |
| 012 | LIANAK |
| 013 | LFAP[D]EA |
| 014 | LIAP[D]EA |
| 015 | TNWAEN |
| 016 | TWAPES |
| 017 | TWSPEL |
| 018 | Sar-Trp-Ala-Glu-Ala-NMeAla |
| 019 | Sar-Trp-Ala-[D]Glu-Ala-Sar |
| 020 | AWAEAK |
| 021 | AWA[D]EAK |
| 022 | AWANAK |
| 023 | AWA[D]NAK |
| 024 | AWAPEA |
| 025 | AWAP[D]EA |
| 026 | PSAPEN |
| 027 | HMAPEV |
| 028 | YIAPEV |
| 029 | KAPEPL |
| 030 | LVAEAK |
| 031 | WMAPET |
| 032 | EAPEDL |
| 033 | DVAPED |
| 034 | YLAPEV |
| 035 | YMAPEH |
| 036 | QIAEGM |
| 037 | WTAPEA |
| 038 | WYAPEC |
| 039 | SNVAEA |
| 040 | YRAPEI |

*FIG. 8A*

| SEQ ID NO. | PEPTIDE SEQUENCE |
|---|---|
| 041 | ANVAEK |
| 042 | ANVAENA |
| 043 | GGQIANI |
| 044 | IAibAEAK |
| 045 | II(N-MeA)EAK |
| 046 | IWGLDG(βA)K |
| 047 | II(N-methyl)AEAK |
| 048 | L(Abu)AEAK |
| 049 | L(Aib)AEAK |
| 050 | LI[D]AEAK |
| 051 | LI(NmeA)EAK |
| 052 | LIA(Aib)EA |
| 053 | LIA[D]EAK |
| 054 | LIADEAK |
| 055 | LIAEAA |
| 056 | LIAEAK |
| 057 | LIAGEG |
| 058 | LIAGGE |
| 059 | LIAKGK |
| 060 | LIANAK |
| 061 | LIAPEA |
| 062 | LIAPXA X=Hydroxyproline |
| 063 | LIAQAK |
| 064 | IWGLDGβAK |
| 065 | LIAAibEA |
| 066 | LIAP[D]EAK |
| 067 | LIXEAK X=Hydroxyproline |
| 068 | WIALEGβAK |
| 069 | FIAP[D]EA |

*FIG. 8B*

| SEQ ID NO. | SEQUENCE |
|---|---|
| 070 | ANVAENA |
| 071 | LIAEAK |
| 072 | LIAPEA |
| 073 | LXAEAK |
| 074 | LIXEAK |
| 075 | LXAEAK |
| 076 | GGQIANI |
| 077 | EGIAGK |
| 078 | LIADAK |
| 079 | LIANAK |
| 080 | LIAEAA |
| 081 | LIAQAK |
| 082 | LIAGGE |
| 083 | LIAGEG |
| 084 | ANVAEK |
| 085 | LIAKGK |
| 086 | GTPGPQGIAGQRGVV |
| 087 | IXAEAK |
| 088 | LXAEAK |
| 089 | LPAEAK |
| 090 | LIPEAK |
| 091 | LIXEAK |
| 092 | LIAXEA |
| 093 | IWGLDGXK |
| 094 | WIALEGXK |
| 095 | GPQGIAGQR |
| 096 | QGIAGQ |
| 097 | QGIAGQR |
| 098 | FGIAGF |
| 099 | GIAGQ |
| 100 | QGAIAQ |
| 101 | FGIAGF |
| 102 | CGIAGC |
| 103 | EGIAGK |
| 104 | XIAA |
| 105 | IAX |
| 106 | XIAX |
| 107 | IIXEAK |
| 108 | LIXEAK |
| 109 | LIAXAK |
| 110 | LIAPXA |
| 111 | LIAXAK |
| 112 | LIAE |
| 113 | NVAE |

*FIG. 8C*

| AMINO ACID | 3-LETTER CODE | 1-LETTER CODE |
| --- | --- | --- |
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any Amino Acid As Above | Xaa | X |

*FIG. 9A*

| UNNATURAL AMINO ACID | SYMBOL | UNNATURAL AMINO ACID | SYMBOL |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
| carboxylate |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |

*FIG. 9B*

| UNNATURAL AMINO ACID | SYMBOL | UNNATURAL AMINO ACID | SYMBOL |
|---|---|---|---|
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododecylglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |

*FIG. 9B (cont.)*

| UNNATURAL AMINO ACID | SYMBOL | UNNATURAL AMINO ACID | SYMBOL |
|---|---|---|---|
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mval | L-α-methyltyrosine | Mtyr |
| L-α-methylleucine | Nmleu | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |
| N-methyl tryptophan | Ntrp | | |

FIG. 9B (cont.)

INHIBITORS OF NF KAPPA-B ACTIVITY FOR TREATMENT OF DISEASES AND DISORDERS

CROSS REFERENCE TO RELATED APPLICATIONS

This application is a divisional application of U.S. patent application Ser. No. 17/505,544, filed on Oct. 19, 2021, now U.S. Pat. No. 11,773,135 issued Oct. 3, 2023, which is a divisional application of U.S. patent application Ser. No. 15/982,837, filed on May 17, 2018, now U.S. Pat. No. 11,174,286 issued Nov. 16, 2021, which is a continuation of U.S. patent application Ser. No. 14/866,040, filed on Sep. 25, 2015, now U.S. Pat. No. 10,030,048 issued Jul. 24, 2018 which claims priority benefit of U.S. Provisional Patent Application No. 62/055,982, filed Sep. 26, 2014. The entire contents of those applications are hereby incorporated by reference herein.

SUBMISSION OF SEQUENCE LISTING ON ASCII TEXT FILE

The contents of the electronic sequence listing (750922000111seqlist.xml; Size: 155,470 bytes; and Date of Creation: Aug. 22, 2023) are herein incorporated by reference in their entirety.

FIELD OF THE INVENTION

Compositions and methods are disclosed for inhibition of activation of NF KB leading to treatment and prevention of diseases and disorders arising from dysregulation of NF KB (nuclear factor kappa-light-chain-enhancer of activated B cells; NF kappa-B).

TECHNICAL FIELD

The present invention relates to the use of the disclosed compounds to inhibit the activation of NF KB, for use in prevention and therapy of various diseases caused by agents that disturb normal modulation of NF KB, such as stress, injury, infection, inflammation, cytokines, free radicals, UV, ionizing radiation, oxidized LDL, bacterial and viral products and antigens, immunological disorders, certain drugs, and chemotherapy.

BACKGROUND

NF κB is a contributory factor in a large number of diseases and disorders. It is involved in numerous pathways mediating cell proliferation, survival, apoptosis, adhesion, invasion, and neo-vascularization in various cell types. Detailed listings of diseases and disorders that involve dysregulation of NF κB are presented below. Inhibition of the activation of NF κB is a highly desirable goal. Current clinical practice is based on the use of TNF α antagonists in treatment of diseases involving NF κB.

SUMMARY OF THE INVENTION

Compositions and methods for inhibiting the activity or the activation of NF κB are disclosed herein. Compounds which are 4-20 residue peptides, peptide-mimetics, or peptoids are disclosed herein. The term peptide in this application refers to peptides (that is, standard peptides excluding peptoids and peptide-mimetics), peptide-mimetics, and peptoids together. The invention as described here relates to the disclosed peptides and related compounds that inhibit the activation of NF κB, differentially modulate genes affected by NF κB, and methods for the use thereof, in the treatment of diseases and disorders in humans and non-human patients in the need for such treatments. Additional features and advantages of the invention will be apparent from the detailed description which follows, taken in conjunction with the accompanying drawings, which together illustrate, by way of example, features of the invention.

In any of the embodiments herein, any of the groups of peptides, or any of the groups of peptides indicated as usable for treatment of a disease or disorder, can additionally carry the proviso that the peptide contains at least one non-naturally-occurring amino acid. In any of the embodiments herein, any of the groups of peptides, or any of the groups of peptides indicated as usable for treatment of a disease or disorder, can additionally carry the proviso that the peptide contains at least one non-proteinogenic amino acid. In any of the embodiments herein, any of the groups of peptides, or any of the groups of peptides indicated as usable for treatment of a disease or disorder, can additionally carry the proviso that the peptide contains at least one D-amino acid.

In any of the embodiments herein, the disclosure of "peptides" includes disclosure of and embodiments directed to "standard peptides" (polymers of alpha-amino acids and/or imino acids without peptide bond modifications, that is, peptides excluding peptoids and peptide-mimetics).

In one embodiment, the NF kappa B inhibiting peptides are selected from the group consisting of peptides of four to twenty amino acid residues in length, comprising the sequence:

Xxx-Ala-Pro-Glu where Xxx is selected from the group consisting of Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala. This peptide motif is designated as CORE SEQUENCE (1). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS: 041-113. NF kappa B inhibiting peptides of four to twenty amino acid residues in length comprising CORE SEQUENCE (1) are designated as the peptides of CORE SEQUENCE (1).

In one embodiment of the peptides of CORE SEQUENCE (1), the NF kappa B inhibiting peptides are selected from the group consisting of peptides of four to twenty amino acid residues in length, comprising the sequence:

Xxx-Ala-Pro-Glu where Xxx is selected from the group consisting of Met, Ile, Val, Cys, Trp, Tyr, or Phe. This peptide motif is designated as CORE SEQUENCE (1-N). NF kappa B inhibiting peptides of four to twenty amino acid residues in length comprising CORE SEQUENCE (1-N) are designated as the peptides of CORE SEQUENCE (1-N). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS: 041-113.

In one embodiment of the peptides of CORE SEQUENCE (1), the NF kappa B inhibiting peptides are selected from the group consisting of peptides of four to twenty amino acid residues in length, comprising the sequence:

Xxx-Ala-Pro-Glu where Xxx is selected from the group consisting of 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala. This peptide motif is designated as CORE SEQUENCE (1-U). NF kappa B inhibiting peptides of four to twenty amino acid residues in length comprising CORE SEQUENCE (1-U) are designated as the peptides of CORE SEQUENCE (1-U). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (1), the NF kappa B inhibiting peptides are selected from the group consisting of peptides up to twenty amino acid residues in length comprising the sequence:
YMAPEV (SEQ ID NO:001), IIAPEG (SEQ ID NO:002), TWAPES (SEQ ID NO:016), AWAPEA (SEQ ID NO:024), PSAPEN (SEQ ID NO:026), HMAPEV (SEQ ID NO:027), YIAPEV (SEQ ID NO:028), KAPEPL (SEQ ID NO:029), WMAPET (SEQ ID NO:031), EAPEDL (SEQ ID NO:032), DVAPED (SEQ ID NO:033), YLAPEV (SEQ ID NO:034), YMAPEH (SEQ ID NO:035), WTAPEA (SEQ ID NO:037), WYAPEC (SEQ ID NO:038), YRAPEI (SEQ ID NO:040), and LIAPEA (SEQ ID NO:061). These peptides are designated as the peptides of GROUP (1-S).

In one embodiment of the peptides of CORE SEQUENCE (1), the NF kappa B inhibiting peptides are selected from the group consisting of peptides up to twenty amino acid residues in length comprising the sequence:
YMAPEV (SEQ ID NO:001), IIAPEG (SEQ ID NO:002), TWAPES (SEQ ID NO:016), AWAPEA (SEQ ID NO:024), PSAPEN (SEQ ID NO:026), HMAPEV (SEQ ID NO:027), YIAPEV (SEQ ID NO:028), KAPEPL (SEQ ID NO:029), WMAPET (SEQ ID NO:031), EAPEDL (SEQ ID NO:032), DVAPED (SEQ ID NO:033), YLAPEV (SEQ ID NO:034), YMAPEH (SEQ ID NO:035), WTAPEA (SEQ ID NO:037), WYAPEC (SEQ ID NO:038), and YRAPEI (SEQ ID NO:040), with the proviso that peptides comprising the sequence LIAEAK (SEQ ID NO:009), peptides comprising the sequence LIANAK (SEQ ID NO:012), and peptides comprising SEQ ID NOS:041-113 are excluded. These peptides are designated as the peptides of GROUP (1-T).

In one embodiment of the peptides of CORE SEQUENCE (1), the NF kappa B inhibiting peptides are selected from the group consisting of peptides of the sequence:
YMAPEV (SEQ ID NO:001), IIAPEG (SEQ ID NO:002), TWAPES (SEQ ID NO:016), AWAPEA (SEQ ID NO:024), PSAPEN (SEQ ID NO:026), HMAPEV (SEQ ID NO:027), YIAPEV (SEQ ID NO:028), KAPEPL (SEQ ID NO:029), WMAPET (SEQ ID NO:031), EAPEDL (SEQ ID NO:032), DVAPED (SEQ ID NO:033), YLAPEV (SEQ ID NO:034), YMAPEH (SEQ ID NO:035), WTAPEA (SEQ ID NO:037), WYAPEC (SEQ ID NO:038), YRAPEI (SEQ ID NO:040), and LIAPEA (SEQ ID NO:061). These peptides are designated as the peptides of GROUP (1-V).

In any of the foregoing embodiments, the peptides can be of length four to fifteen amino acids, four to twelve amino acids, four to ten amino acids, four to eight amino acids, six to twenty amino acids, six to fifteen amino acids, six to twelve amino acids, six to ten amino acids, or six to eight amino acids. Any of the foregoing embodiments can exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (1), the NF kappa B inhibiting peptides are selected from the group consisting of peptides of the sequence:
YMAPEV (SEQ ID NO:001), IIAPEG (SEQ ID NO:002), TWAPES (SEQ ID NO:016), AWAPEA (SEQ ID NO:024), PSAPEN (SEQ ID NO:026), HMAPEV (SEQ ID NO:027), YIAPEV (SEQ ID NO:028), KAPEPL (SEQ ID NO:029), WMAPET (SEQ ID NO:031), EAPEDL (SEQ ID NO:032), DVAPED (SEQ ID NO:033), YLAPEV (SEQ ID NO:034), YMAPEH (SEQ ID NO:035), WTAPEA (SEQ ID NO:037), WYAPEC (SEQ ID NO:038), and YRAPEI (SEQ ID NO:040). These peptides are designated as the peptides of GROUP (1-W).

In one embodiment, the NF kappa B inhibiting peptides are selected from the group consisting of peptides of four to twenty amino acid residues in length, comprising the sequence:

Xxx-Ala-Pro-D-Glu where Xxx is selected from the group consisting of Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala. This peptide motif is designated as CORE SEQUENCE (2). NF kappa B inhibiting peptides of four to twenty amino acid residues in length comprising CORE SEQUENCE (2) are designated as the peptides of CORE SEQUENCE (2). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS: 041-113.

In one embodiment of the peptides of CORE SEQUENCE (2), the NF kappa B inhibiting peptides are selected from the group consisting of peptides of four to twenty amino acid residues in length, comprising the sequence:

Xxx-Ala-Pro-D-Glu where Xxx is selected from the group consisting of Met, Ile, Val, Cys, Trp, Tyr, or Phe. This peptide motif is designated as CORE SEQUENCE (2-N). NF kappa B inhibiting peptides of four to twenty amino acid residues in length comprising CORE SEQUENCE (2-N) are designated as the peptides of CORE SEQUENCE (2-N). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS: 041-113.

In one embodiment of the peptides of CORE SEQUENCE (2), the NF kappa B inhibiting peptides are selected from the group consisting of peptides of four to twenty amino acid residues in length, comprising the sequence:

Xxx-Ala-Pro-D-Glu where Xxx is selected from the group consisting of 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala. This peptide motif is designated as CORE SEQUENCE (2-U). NF kappa B inhibiting peptides of four to twenty amino acid residues in length comprising CORE SEQUENCE (2-U) are designated as the peptides of CORE SEQUENCE (2-U). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (2), the NF kappa B inhibiting peptides are selected from the group consisting of peptides up to twenty amino acid residues in length comprising the sequence: LFAP$_{[D]}$EA (SEQ ID NO:013), LIAP$_{[D]}$EA (SEQ ID NO:014), or AWAP[D]EA (SEQ ID NO:025). These peptides are designated as the peptides of GROUP (2-S).

In one embodiment of the peptides of CORE SEQUENCE (2), the NF kappa B inhibiting peptides are selected from the group consisting of peptides up to twenty amino acid residues in length comprising the sequence: LFAP$_{[D]}$EA (SEQ ID NO:013), LIAP$_{[D]}$EA (SEQ ID NO:014), or AWAP[D]EA (SEQ ID NO:025), with the proviso that peptides comprising the sequence LIAEAK (SEQ ID NO:009), peptides comprising the sequence LIANAK (SEQ ID NO:012), and peptides comprising SEQ ID NOS:041-113 are excluded. These peptides are designated as the peptides of GROUP (2-T).

In any of the foregoing embodiments, the peptides can be of length four to fifteen amino acids, four to twelve amino acids, four to ten amino acids, four to eight amino acids, six to twenty amino acids, six to fifteen amino acids, six to twelve amino acids, six to ten amino acids, or six to eight amino acids. Any of the foregoing embodiments can exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (2), the NF kappa B inhibiting peptides are selected from the group consisting of peptides of the sequence: LFAP$_{[D]}$EA (SEQ ID NO:013), LIAP$_{[D]}$EA (SEQ ID NO:014), or AWAP[D]EA (SEQ ID NO:025). These peptides are designated as the peptides of GROUP (2-V).

In one embodiment, the NF kappa B inhibiting peptides are selected from the group consisting of peptides of four to twenty amino acid residues in length, comprising the sequence:

Xxx-Ala-Glu-Ala where Xxx is selected from the group consisting of Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala. This peptide motif is designated as CORE SEQUENCE (3). In a further embodiment, the peptides of this motif exclude peptides comprising the sequence LIAEAK (SEQ ID NO:009). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113. NF kappa B inhibiting peptides of four to twenty amino acid residues in length comprising CORE SEQUENCE (3) are designated as the peptides of CORE SEQUENCE (3).

In one embodiment of the peptides of CORE SEQUENCE (3), the NF kappa B inhibiting peptides are selected from the group consisting of peptides of four to twenty amino acid residues in length, comprising the sequence:

Xxx-Ala-Glu-Ala where Xxx is selected from the group consisting of Met, Ile, Val, Cys, Trp, Tyr, or Phe. This peptide motif is designated as CORE SEQUENCE (3-N). NF kappa B inhibiting peptides of four to twenty amino acid residues in length comprising CORE SEQUENCE (3-N) are designated as the peptides of CORE SEQUENCE (3-N). In a further embodiment, the peptides of CORE SEQUENCE (3-N) exclude peptides comprising the sequence LIAEAK (SEQ ID NO:009). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (3), the NF kappa B inhibiting peptides are selected from the group consisting of peptides of four to twenty amino acid residues in length, comprising the sequence:

Xxx-Ala-Glu-Ala where Xxx is selected from the group consisting of 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala. This peptide motif is designated as CORE SEQUENCE (3-U). NF kappa B inhibiting peptides of four to twenty amino acid residues in length comprising CORE SEQUENCE (3-U) are designated as the peptides of CORE SEQUENCE (3-U). In a further embodiment, the peptides of CORE SEQUENCE (3-U) exclude peptides comprising the sequence LIAEAK (SEQ ID NO:009). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS: 041-113.

In one embodiment of the peptides of CORE SEQUENCE (3), the NF kappa B inhibiting peptides are selected from the group consisting of peptides up to twenty amino acid residues in length having the sequence: EIAEAL (SEQ ID NO:003), SNVAEA (SEQ ID NO:004), ANIAEA (SEQ ID NO:005), LWAEAK (SEQ ID NO:008), LIAEAK (SEQ ID NO:009), LVAEAH (SEQ ID NO:011), Sar-Trp-Ala-Glu-Ala-NMeAl (SEQ ID NO:018), AWAEAK (SEQ ID NO:020), LVAEAK (SEQ ID NO:030), or SNVAEA (SEQ ID NO:039). These peptides are designated as the peptides of GROUP (3-S).

In another embodiment of the peptides of CORE SEQUENCE (3), the NF kappa B inhibiting peptides are selected from the group consisting of peptides up to twenty amino acid residues in length comprising the sequence: EIAEAL (SEQ ID NO:003), SNVAEA (SEQ ID NO:004), ANIAEA (SEQ ID NO:005), LWAEAK (SEQ ID NO:008), LVAEAH (SEQ ID NO:011), Sar-Trp-Ala-Glu-Ala-NMeAl (SEQ ID NO:018), AWAEAK (SEQ ID NO:020), LVAEAK (SEQ ID NO:030), or SNVAEA (SEQ ID NO:039), with the proviso that peptides comprising the sequence LIAEAK (SEQ ID NO:009), peptides comprising the sequence LIANAK (SEQ ID NO:012), and peptides comprising SEQ ID NOS:041-113 are excluded. These peptides are designated as the peptides of GROUP (3-T).

In any of the foregoing embodiments, the peptides can be of length four to fifteen amino acids, four to twelve amino acids, four to ten amino acids, four to eight amino acids, six to twenty amino acids, six to fifteen amino acids, six to twelve amino acids, six to ten amino acids, or six to eight amino acids. Any of the foregoing embodiments can exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (3), the NF kappa B inhibiting peptides are selected from the group consisting of peptides of the sequence:
EIAEAL (SEQ ID NO:003), SNVAEA (SEQ ID NO:004), ANIAEA (SEQ ID NO:005), LWAEAK (SEQ ID NO:008), LIAEAK (SEQ ID NO:009), LVAEAH (SEQ ID NO:011), Sar-Trp-Ala-Glu-Ala-NMeAl (SEQ ID NO:018), AWAEAK (SEQ ID NO:020), LVAEAK (SEQ ID NO:030), or SNVAEA (SEQ ID NO:039). These peptides are designated as the peptides of GROUP (3-V).

In another embodiment of the peptides of CORE SEQUENCE (3), the NF kappa B inhibiting peptides are selected from the group consisting of peptides of the sequence:
EIAEAL (SEQ ID NO:003), SNVAEA (SEQ ID NO:004), ANIAEA (SEQ ID NO:005), LWAEAK (SEQ ID NO:008), LVAEAH (SEQ ID NO:011), Sar-Trp-Ala-Glu-Ala-NMeAl (SEQ ID NO:018), AWAEAK (SEQ ID NO:020), LVAEAK (SEQ ID NO:030), or SNVAEA (SEQ ID NO:039). These peptides are designated as the peptides of GROUP (3-W).

In one embodiment, the NF kappa B inhibiting peptides are selected from the group consisting of peptides of four to twenty amino acid residues in length, comprising the sequence:
Xxx-Ala-D-Glu-Ala
where Xxx is selected from the group consisting of Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala. This peptide motif is designated as CORE SEQUENCE (4). NF kappa B inhibiting peptides of four to twenty amino acid residues in length comprising CORE SEQUENCE (4) are designated as the peptides of CORE SEQUENCE (4). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS: 041-113.

In one embodiment of the peptides of CORE SEQUENCE (4), the NF kappa B inhibiting peptides are selected from the group consisting of peptides of four to twenty amino acid residues in length, comprising the sequence:
Xxx-Ala-D-Glu-Ala
where Xxx is selected from the group consisting of Met, Ile, Val, Cys, Trp, Tyr, or Phe. This peptide motif is designated as CORE SEQUENCE (4-N). NF kappa B inhibiting peptides of four to twenty amino acid residues in length comprising CORE SEQUENCE (4-N) are designated as the peptides of CORE SEQUENCE (4-N). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS: 041-113.

In one embodiment of the peptides of CORE SEQUENCE (4), the NF kappa B inhibiting peptides are selected from the group consisting of peptides of four to twenty amino acid residues in length, comprising the sequence:
Xxx-Ala-D-Glu-Ala
where Xxx is selected from the group consisting of 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala. This peptide motif is designated as CORE SEQUENCE (4-U). NF kappa B inhibiting peptides of four to twenty amino acid residues in length comprising CORE SEQUENCE (4-U) are designated as the peptides of CORE SEQUENCE (4-U). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (4), the NF kappa B inhibiting peptides are selected from the group consisting of peptides up to twenty amino acid residues in length comprising the sequence: Sar-Trp-Ala-[D]Glu-Ala-Sar (SEQ ID NO:019) or AWA[D]EAK (SEQ ID NO:021). These peptides are designated as the peptides of GROUP (4-S).

In one embodiment of the peptides of CORE SEQUENCE (4), the NF kappa B inhibiting peptides are selected from the group consisting of peptides up to twenty amino acid residues in length comprising the sequence: Sar-Trp-Ala-[D]Glu-Ala-Sar (SEQ ID NO:019) or AWA[D]EAK (SEQ ID NO:021), with the proviso that peptides comprising the sequence LIAEAK (SEQ ID NO:009), peptides comprising the sequence LIANAK (SEQ ID NO:012), and peptides comprising SEQ ID NOS:041-113 are excluded. These peptides are designated as the peptides of GROUP (4-T).

In any of the foregoing embodiments, the peptides can be of length four to fifteen amino acids, four to twelve amino acids, four to ten amino acids, four to eight amino acids, six to twenty amino acids, six to fifteen amino acids, six to twelve amino acids, six to ten amino acids, or six to eight amino acids. Any of the foregoing embodiments can exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (4), the NF kappa B inhibiting peptides are selected from the group consisting of peptides of the sequence: Sar-Trp-Ala-[D]Glu-Ala-Sar (SEQ ID NO:019) or AWA[D]EAK (SEQ ID NO:021). These peptides are designated as the peptides of GROUP (4-V).

In one embodiment, the NF kappa B inhibiting peptides are selected from the group consisting of peptides of four to twenty amino acid residues in length, comprising the sequence:
Xxx-Ala-Asn-Ala
where Xxx is selected from the group consisting of Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala. This peptide motif is designated as CORE SEQUENCE (5). NF kappa B inhibiting peptides of four to twenty amino acid residues in length comprising CORE SEQUENCE (5) are designated as the peptides of CORE SEQUENCE (5). In a further embodiment, the peptides of CORE SEQUENCE (5) exclude peptides comprising the sequence LIANAK (SEQ ID NO:012). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (5), the NF kappa B inhibiting peptides are selected from the group consisting of peptides of four to twenty amino acid residues in length, comprising the sequence:
Xxx-Ala-Asn-Ala
where Xxx is selected from the group consisting of Met, Ile, Val, Cys, Trp, Tyr, or Phe. This peptide motif is designated as CORE SEQUENCE (5-N). NF kappa B inhibiting peptides of four to twenty amino acid residues in length comprising CORE SEQUENCE (5-N) are designated as the peptides of CORE SEQUENCE (5-N). In a further embodiment, the peptides of CORE SEQUENCE (5-N) exclude peptides comprising the sequence LIANAK (SEQ ID NO:012). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (5), the NF kappa B inhibiting peptides are selected from the group consisting of peptides of four to twenty amino acid residues in length, comprising the sequence:
Xxx-Ala-Asn-Ala
where Xxx is selected from the group consisting of 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala. This peptide motif is designated as CORE SEQUENCE (5-U). NF kappa B inhibiting peptides of four to twenty amino acid residues in length comprising CORE SEQUENCE (5-U) are designated as the peptides of CORE SEQUENCE (5-U). In a further embodiment, the peptides of CORE SEQUENCE (5-U) exclude peptides comprising the sequence LIANAK (SEQ ID NO:012). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (5), the NF kappa B inhibiting peptides are selected from the group consisting of peptides up to twenty amino acid residues in length comprising the sequence: LIANAK (SEQ ID NO:012) or AWANAK (SEQ ID NO:022). These peptides are designated as the peptides of GROUP (5-S).

In one embodiment of the peptides of CORE SEQUENCE (5), the NF kappa B inhibiting peptides are selected from the group consisting of peptides up to twenty amino acid residues in length comprising the sequence: AWANAK (SEQ ID NO:022), with the proviso that peptides comprising the sequence LIAEAK (SEQ ID NO:009), peptides comprising the sequence LIANAK (SEQ ID NO:012), and peptides comprising SEQ ID NOS:041-113 are excluded. These peptides are designated as the peptides of GROUP (5-T).

In any of the foregoing embodiments, the peptides can be of length four to fifteen amino acids, four to twelve amino acids, four to ten amino acids, four to eight amino acids, six to twenty amino acids, six to fifteen amino acids, six to twelve amino acids, six to ten amino acids, or six to eight amino acids. Any of the foregoing embodiments can exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (5), the NF kappa B inhibiting peptides are selected from the group consisting of peptides of the sequence:
LIANAK (SEQ ID NO:012) or AWANAK (SEQ ID NO:022). These peptides are designated as the peptides of GROUP (5-V).

In one embodiment of the peptides of CORE SEQUENCE (5), the NF kappa B inhibiting peptides are selected from the group consisting of peptides of the sequence:
AWANAK (SEQ ID NO:022). This peptide is designated as the peptide of GROUP (5-W).

In one embodiment, the NF kappa B inhibiting peptides are selected from the group consisting of peptides of four to twenty amino acid residues in length, comprising the sequence:

Xxx-Ala-D-Asn-Ala where Xxx is selected from the group consisting of Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala. This peptide motif is designated as CORE SEQUENCE (6). NF kappa B inhibiting peptides of four to twenty amino acid residues in length comprising CORE SEQUENCE (6) are designated as the peptides of CORE SEQUENCE (6). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (6), the NF kappa B inhibiting peptides are selected from the group consisting of peptides of four to twenty amino acid residues in length, comprising the sequence:

Xxx-Ala-D-Asn-Ala where Xxx is selected from the group consisting of Met, Ile, Val, Cys, Trp, Tyr, or Phe. This peptide motif is designated as CORE SEQUENCE (6-N). NF kappa B inhibiting peptides of four to twenty amino acid residues in length comprising CORE SEQUENCE (6-N) are designated as the peptides of CORE SEQUENCE (6-N). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (6), the NF kappa B inhibiting peptides are selected from the group consisting of peptides of four to twenty amino acid residues in length, comprising the sequence:

Xxx-Ala-D-Asn-Ala where Xxx is selected from the group consisting of 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala. This peptide motif is designated as CORE SEQUENCE (6-U). NF kappa B inhibiting peptides of four to twenty amino acid residues in length comprising CORE SEQUENCE (5) are designated as the peptides of CORE SEQUENCE (6-U). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (6), the NF kappa B inhibiting peptides are selected from the group consisting of peptides up to twenty amino acid residues in length comprising the sequence: AWA[D]NAK (SEQ ID NO:023). These peptides are designated as the peptide of GROUP (6-S).

In one embodiment of the peptides of CORE SEQUENCE (6), the NF kappa B inhibiting peptides are selected from the group consisting of peptides up to twenty amino acid residues in length comprising the sequence: AWA[D]NAK (SEQ ID NO:023), with the proviso that peptides comprising the sequence LIAEAK (SEQ ID NO:009), peptides comprising the sequence LIANAK (SEQ ID NO:012), and peptides comprising SEQ ID NOS:041-113 are excluded. These peptides are designated as the peptide of GROUP (6-T).

In any of the foregoing embodiments, the peptides can be of length four to fifteen amino acids, four to twelve amino acids, four to ten amino acids, four to eight amino acids, six to twenty amino acids, six to fifteen amino acids, six to twelve amino acids, six to ten amino acids, or six to eight amino acids. Any of the foregoing embodiments can exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (6), the NF kappa B inhibiting peptides are selected from the group consisting of the peptide of the sequence: AWA[D]NAK (SEQ ID NO:023). This peptide is designated as the peptide of GROUP (6-V).

In one embodiment, the NF kappa B inhibiting peptides are selected from the group consisting of peptides of four to twenty amino acid residues in length, comprising the sequence:

Xxx-Ala-Glu-Asn where Xxx is selected from the group consisting of Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala. This peptide motif is designated as CORE SEQUENCE (7). NF kappa B inhibiting peptides of four to twenty amino acid residues in length comprising CORE SEQUENCE (7) are designated as the peptides of CORE SEQUENCE (7). In a further embodiment, the peptides of CORE SEQUENCE (7) exclude peptides comprising the sequence ANVAENA (SEQ ID NO:042). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (7), the NF kappa B inhibiting peptides are selected from the group consisting of peptides of four to twenty amino acid residues in length, comprising the sequence:

Xxx-Ala-Glu-Asn where Xxx is selected from the group consisting of Met, Ile, Val, Cys, Trp, Tyr, or Phe. This peptide motif is designated as CORE SEQUENCE (7-N). NF kappa B inhibiting peptides of four to twenty amino acid residues in length comprising CORE SEQUENCE (7-N) are designated as the peptides of CORE SEQUENCE (7-N). In a further embodiment, the peptides of CORE SEQUENCE (7-N) exclude peptides comprising the sequence ANVAENA (SEQ ID NO:042). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (7), the NF kappa B inhibiting peptides are selected from the group consisting of peptides of four to twenty amino acid residues in length, comprising the sequence:

Xxx-Ala-Glu-Asn where Xxx is selected from the group consisting of 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala. This peptide motif is designated as CORE SEQUENCE (7-U). NF kappa B inhibiting peptides of four to twenty amino acid residues in length comprising CORE SEQUENCE (7-U) are designated as the peptides of CORE SEQUENCE (7-U). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (7), the NF kappa B inhibiting peptides are selected from the group consisting of peptides of four to twenty amino acid residues in length comprising the sequence: NVAENA (SEQ ID NO:010) or ANVAENA (SEQ ID NO:042). These peptides are designated as the peptides of GROUP (7-S).

In one embodiment of the peptides of CORE SEQUENCE (7), the NF kappa B inhibiting peptides are selected from the group consisting of peptides of four to twenty amino acid residues in length comprising the sequence: NVAENA (SEQ ID NO:010), with the proviso that peptides comprising the sequence LIAEAK (SEQ ID NO:009), peptides comprising the sequence LIANAK (SEQ ID NO:012), and peptides comprising SEQ ID NOS:041-113 are excluded. These peptides are designated as the peptides of GROUP (7-T).

In any of the foregoing embodiments, the peptides can be of length four to fifteen amino acids, four to twelve amino acids, four to ten amino acids, four to eight amino acids, six to twenty amino acids, six to fifteen amino acids, six to twelve amino acids, six to ten amino acids, or six to eight amino acids. Any of the foregoing embodiments can exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (7), the NF kappa B inhibiting peptides are selected from the group consisting of peptides of the sequence: NVAENA (SEQ ID NO:010) or ANVAENA (SEQ ID NO:042). These peptides are designated as the peptides of GROUP (7-V).

In one embodiment of the peptides of CORE SEQUENCE (7), the NF kappa B inhibiting peptide is: NVAENA (SEQ ID NO:010). This peptide is designated as the peptide of GROUP (7-W).

In one embodiment, the NF kappa B inhibiting peptides are selected from the group consisting of peptides of four to twenty amino acid residues in length, comprising the sequence:

Xxx-Ala-D-Glu-Asn where Xxx is selected from the group consisting of Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala. This peptide motif is designated as CORE SEQUENCE (8). NF kappa B inhibiting peptides of four to twenty amino acid residues in length comprising CORE SEQUENCE (8) are designated as the peptides of CORE SEQUENCE (8). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS: 041-113.

In one embodiment of the peptides of CORE SEQUENCE (8), the NF kappa B inhibiting peptides are selected from the group consisting of peptides of four to twenty amino acid residues in length, comprising the sequence:

Xxx-Ala-D-Glu-Asn where Xxx is selected from the group consisting of Met, Ile, Val, Cys, Trp, Tyr, or Phe. This peptide motif is designated as CORE SEQUENCE (8-N). NF kappa B inhibiting peptides of four to twenty amino acid residues in length comprising CORE SEQUENCE (8-N) are designated as the peptides of CORE SEQUENCE (8-N). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS: 041-113.

In one embodiment of the peptides of CORE SEQUENCE (8), the NF kappa B inhibiting peptides are selected from the group consisting of peptides of four to twenty amino acid residues in length, comprising the sequence:

Xxx-Ala-D-Glu-Asn where Xxx is selected from the group consisting of 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala. This peptide motif is designated as CORE SEQUENCE (8-U). NF kappa B inhibiting peptides of four to twenty amino acid residues in length comprising CORE SEQUENCE (8) are designated as the peptides of CORE SEQUENCE (8-U). In a further embodiment, the peptides of this motif exclude peptides comprising the sequence LIAPEA (SEQ ID NO:061) and exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (8), the NF kappa B inhibiting peptides are selected from the group consisting of peptides of four to twenty amino acid residues in length comprising the sequence: NVA[D]ENA (SEQ ID NO: 114) or ANVA[D]ENA (SEQ ID NO:115). These peptides are designated as the peptides of GROUP (8-S).

In one embodiment of the peptides of CORE SEQUENCE (8), the NF kappa B inhibiting peptides are selected from the group consisting of peptides of four to twenty amino acid residues in length comprising the sequence: NVA[D]ENA (SEQ ID NO: 114) or ANVA[D]ENA (SEQ ID NO:115), with the proviso that peptides comprising the sequence LIAEAK (SEQ ID NO:009), peptides comprising the sequence LIANAK (SEQ ID NO:012), and peptides comprising SEQ ID NOS:041-113 are excluded. These peptides are designated as the peptides of GROUP (8-T).

In any of the foregoing embodiments, the peptides can be of length four to fifteen amino acids, four to twelve amino acids, four to ten amino acids, four to eight amino acids, six to twenty amino acids, six to fifteen amino acids, six to twelve amino acids, six to ten amino acids, or six to eight amino acids. Any of the foregoing embodiments can exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS:041-113.

In one embodiment of the peptides of CORE SEQUENCE (8), the NF kappa B inhibiting peptides are selected from the group consisting of peptides of the sequence: NVA[D]ENA (SEQ ID NO:114) or ANVA[D]ENA (SEQ ID NO:115). These peptides are designated as the peptides of GROUP (8-V).

In a further embodiment, any set of peptides of CORE SEQUENCE (1), CORE SEQUENCE (1-N), CORE SEQUENCE (1-U), GROUP (1-S), GROUP (1-T), GROUP (1-V), GROUP (1-W), CORE SEQUENCE (2), CORE SEQUENCE (2-N), CORE SEQUENCE (2-U), GROUP (2-S), GROUP (2-T), GROUP (2-V), CORE SEQUENCE (3), CORE SEQUENCE (3-N), CORE SEQUENCE (3-U), GROUP (3-S), GROUP (3-T), GROUP (3-V), GROUP (3-W), CORE SEQUENCE (4), CORE SEQUENCE (4-N), CORE SEQUENCE (4-U), GROUP (4-S), GROUP (4-T), GROUP (4-V), CORE SEQUENCE (5), CORE SEQUENCE (5-N), CORE SEQUENCE (5-U), GROUP (5-S), GROUP (5-T), GROUP (5-V), GROUP (5-W), CORE SEQUENCE (6), CORE SEQUENCE (6-N), CORE SEQUENCE (6-U), GROUP (6-S), GROUP (6-T), GROUP (6-V), CORE SEQUENCE (7), CORE SEQUENCE (7-N), CORE SEQUENCE (7-U), GROUP (7-S), GROUP (7-T), GROUP (7-V), GROUP (7-W), CORE SEQUENCE (8), CORE SEQUENCE (8-N), CORE SEQUENCE (8-U), GROUP (8-S), GROUP (8-T), or GROUP (8-V), as recited in any part of this disclosure, can contain the additional proviso that peptides comprising the sequence LWAEAK (SEQ ID NO:008) are excluded; the additional proviso that peptides comprising the sequence LIAEAK (SEQ ID NO:009) are excluded; the additional proviso that peptides comprising the sequence LIANAK (SEQ ID NO:012) are excluded; the additional proviso that peptides comprising the sequence LVAEAK (SEQ ID NO:030) are excluded; the additional proviso that peptides comprising the sequence ANVAENA (SEQ ID NO:042) are excluded; the additional proviso that peptides comprising the sequence LIAEAK (SEQ ID NO:009) are excluded, the additional proviso that peptides comprising the sequence LIANAK (SEQ ID NO:012) are excluded, and peptides comprising the sequence ANVAENA (SEQ ID NO:042) are excluded; or the additional proviso that peptides comprising the sequence LWAEAK (SEQ ID NO:008), peptides comprising the sequence LIAEAK (SEQ ID NO:009), peptides comprising the sequence LIANAK (SEQ ID NO:012), peptides comprising the sequence LVAEAK (SEQ ID NO:030), and peptides comprising SEQ ID NOS:041-113 are excluded.

In a further embodiment, any set of peptides of CORE SEQUENCE (1), CORE SEQUENCE (1-N), CORE SEQUENCE (1-U), GROUP (1-S), GROUP (1-T), GROUP (1-V), GROUP (1-W), CORE SEQUENCE (2), CORE SEQUENCE (2-N), CORE SEQUENCE (2-U), GROUP (2-S), GROUP (2-T), GROUP (2-V), CORE SEQUENCE (3), CORE SEQUENCE (3-N), CORE SEQUENCE (3-U), GROUP (3-S), GROUP (3-T), GROUP (3-V), GROUP (3-W), CORE SEQUENCE (4), CORE SEQUENCE (4-N), CORE SEQUENCE (4-U), GROUP (4-S), GROUP (4-T), GROUP (4-V), CORE SEQUENCE (5), CORE SEQUENCE (5-N), CORE SEQUENCE (5-U), GROUP (5-S), GROUP (5-T), GROUP (5-V), GROUP (5-W), CORE SEQUENCE (6), CORE SEQUENCE (6-N), CORE SEQUENCE (6-U), GROUP (6-S), GROUP (6-T), GROUP (6-V), CORE SEQUENCE (7), CORE SEQUENCE (7-N), CORE SEQUENCE (7-U), GROUP (7-S), GROUP (7-T), GROUP (7-V), GROUP (7-W), CORE SEQUENCE (8), CORE SEQUENCE (8-N), CORE SEQUENCE (8-U), GROUP (8-S), GROUP (8-T), or GROUP (8-V), as recited in any part of this disclosure, can contain the additional proviso that one or more peptides comprising the sequence of any one or more of SEQ ID NOS:001-113 in any combination are excluded, with the further proviso that at least one peptide sequence remains in the resulting set.

In the sequences described above and any other sequence disclosed herein, methionine (Met) may be replaced with norleucine (Nor).

In any of the embodiments of the specific peptide sequences disclosed herein, and the methods of use of the peptide sequences disclosed herein, homologous sequences having at least about 70%, at least about 75%, at least about 80%, at least about 85%, at least about 90%, or at least about 95% sequence homology can be used, provided that the core sequence is maintained.

In any of the embodiments of the specific peptide sequences disclosed herein, and the methods of use of the peptide sequences disclosed herein, substitutions can be made in the non-core regions of the sequence by replacing one, two, or three amino acids with a homologous amino acid. Thus, negatively charged amino acids can be substituted for other negatively charged amino acids (Asp, Glu); positively charged amino acids can be substituted for other positively charged amino acids (Lys, Arg, His); hydrophobic amino acids can be substituted for other hydrophobic amino acids (Ala, Val, Ile, Leu, Met); hydrophilic amino acids can be substituted for other hydrophilic amino acids (Ser, Thr) (Asn, Gln); aromatic amino acids can be substituted for other aromatic amino acids (Phe, Tyr, Trp, His); and less bulky amino acids can be substituted for other less bulky amino acids (Ala, Gly). The groups of amino acids in parentheses indicate amino acids considered homologous for purposes of substitution.

In one embodiment, the invention encompasses a method of inhibiting NF κB activation or inhibiting NF κB activity in a cell, tissue, or organ, comprising contacting the cell, tissue, or organ with a therapeutically effective amount of a compound which inhibits NF κB activation or inhibits NF κB activity.

In one embodiment, the invention encompasses a method of inhibiting NF κB activation or inhibiting NF κB activity, for example, in a cell, tissue, organ, or organism, comprising contacting the cell, tissue, or organ with an effective amount of a compound which inhibits NF κB activation or inhibits NF κB activity. The effective amount can lower the activity of NF κB, for example, in a cell, tissue, organ, or organism, by an amount of at least about 10%, at least about 20%, at least about 30%, at least about 40%, at least about 50%, at least about 60%, at least about 70%, at least about 80%, or at least about 90% over the baseline level prior to contacting, as measured by any of the assays described herein. In one embodiment, the effective amount can lower the phosphorylation of NF κB (such as phosphorylation of the p65 subunit or the p50 subunit), for example, in a cell, tissue, organ, or organism, by an amount of at least about 10%, at least about 20%, at least about 30%, at least about 40%, at least about 50%, at least about 60%, at least about 70%, at least about 80%, or at least about 90% over the baseline level prior to contacting, as measured by any of the assays described herein. In one embodiment, the effective amount can lower the amount of expression of NF κB, for example, in a cell, tissue, organ, or organism, by an amount of at least about 10%, at least about 20%, at least about 30%, at least about 40%, at least about 50%, at least about 60%, at least about 70%, at least about 80%, or at least about 90% over the baseline level prior to contacting, as measured by any of the assays described herein. In a further embodiment, the compound is a peptide. In yet a further embodiment, the compound is a peptide selected from the group consisting of peptides of CORE SEQUENCE (1), CORE SEQUENCE (1-N), CORE SEQUENCE (1-U), GROUP (1-S), GROUP (1-T), GROUP (1-V), GROUP (1-W), CORE SEQUENCE (2), CORE SEQUENCE (2-N), CORE SEQUENCE (2-U), GROUP (2-S), GROUP (2-T), GROUP (2-V), CORE SEQUENCE (3), CORE SEQUENCE (3-N), CORE SEQUENCE (3-U), GROUP (3-S), GROUP (3-T), GROUP (3-V), GROUP (3-W), CORE SEQUENCE (4), CORE SEQUENCE (4-N), CORE SEQUENCE (4-U), GROUP (4-S), GROUP (4-T), GROUP (4-V), CORE SEQUENCE (5), CORE SEQUENCE (5-N), CORE SEQUENCE (5-U), GROUP (5-S), GROUP (5-T), GROUP (5-V), GROUP (5-W), CORE SEQUENCE (6), CORE SEQUENCE (6-N), CORE SEQUENCE (6-U), GROUP (6-S), GROUP (6-T), GROUP (6-V), CORE SEQUENCE (7), CORE SEQUENCE (7-N), CORE SEQUENCE (7-U), GROUP (7-S), GROUP (7-T), GROUP (7-V), GROUP (7-W), CORE SEQUENCE (8), CORE SEQUENCE (8-N), CORE SEQUENCE (8-U), GROUP (8-S), GROUP (8-T), GROUP (8-V), SEQ ID NOS:001-069, (SEQ ID NOS:001-008, 010, 011, and 013-040), and (SEQ ID NOS:001-007, 010, 011, 013-029, and 031-040), as defined herein.

In one embodiment, the invention embraces a method of treating pain in a patient in need thereof, comprising administering a composition comprising a therapeutically effective amount of a compound which inhibits NF κB activation or inhibits NF κB activity. In a further embodiment, the composition comprises a therapeutically effective amount of one or more peptides selected from the group consisting of peptides of CORE SEQUENCE (1), CORE SEQUENCE (1-N), CORE SEQUENCE (1-U), GROUP (1-S), GROUP (1-T), GROUP (1-V), GROUP (1-W), CORE SEQUENCE (2), CORE SEQUENCE (2-N), CORE SEQUENCE (2-U), GROUP (2-S), GROUP (2-T), GROUP (2-V), CORE SEQUENCE (3), CORE SEQUENCE (3-N), CORE SEQUENCE (3-U), GROUP (3-S), GROUP (3-T), GROUP (3-V), GROUP (3-W), CORE SEQUENCE (4), CORE SEQUENCE (4-N), CORE SEQUENCE (4-U), GROUP (4-S), GROUP (4-T), GROUP (4-V), CORE SEQUENCE (5), CORE SEQUENCE (5-N), CORE SEQUENCE (5-U), GROUP (5-S), GROUP (5-T), GROUP (5-V), GROUP (5-W), CORE SEQUENCE (6), CORE SEQUENCE (6-N), CORE SEQUENCE (6-U), GROUP (6-S), GROUP (6-T), GROUP (6-V), CORE SEQUENCE (7), CORE SEQUENCE (7-N), CORE SEQUENCE (7-U), GROUP (7-S), GROUP (7-T), GROUP (7-V), GROUP (7-W), CORE SEQUENCE (8), CORE SEQUENCE (8-N), CORE SEQUENCE (8-U), GROUP (8-S), GROUP (8-T), GROUP (8-V), SEQ ID NOS:001-069, (SEQ ID NOS:001-007, 010, 011, 013-029, and 031-040), and (SEQ ID NOS:001-007, 010, 011, 013-029, and 031-040) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (1) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (1-N) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (1-U) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (1-S) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (1-V) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (2) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (2-N) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (2-U) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (2-S) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (2-T) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (2-V) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (3) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (3-N) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (3-U) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (3-S) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (3-T) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (3-V) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (3-W) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (4) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (4-N) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (4-U) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (4-S) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (4-T) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (4-V) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (5) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (5-N) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (5-U) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (5-S) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (5-T) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (5-V) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (5-W) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (6) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (6-N) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (6-U) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (6-S) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (6-T) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (6-V) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (7) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (7-N) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (7-U) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (7-S) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (7-T) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (7-V) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (7-W) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (8) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (8-N) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of CORE SEQUENCE (8-U) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (8-S) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (8-T) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of GROUP (8-V) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of SEQ ID NOS:001 to 040 to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of SEQ ID NOS:001-008, 010, 011, and 013-040 to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating pain in a patient in need thereof, comprising administering a composition comprising a therapeutically effective amount of one or more peptides selected from the group consisting of SEQ ID NOS:041-069 to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the pain is associated with wound healing. In one embodiment, the pain excludes pain associated with wound healing.

In one embodiment, the invention embraces a method of treating inflammation in a patient in need thereof, comprising administering a composition comprising a therapeutically effective amount of a compound which inhibits NF κB activation or inhibits NF κB activity. In a further embodiment, the composition comprises a therapeutically effective amount of one or more peptides selected from the group consisting of peptides of CORE SEQUENCE (1), CORE SEQUENCE (1-N), CORE SEQUENCE (1-U), GROUP (1-S), GROUP (1-T), GROUP (1-V), GROUP (1-W), CORE SEQUENCE (2), CORE SEQUENCE (2-N), CORE SEQUENCE (2-U), GROUP (2-S), GROUP (2-T), GROUP (2-V), CORE SEQUENCE (3), CORE SEQUENCE (3-N), CORE SEQUENCE (3-U), GROUP (3-S), GROUP (3-T), GROUP (3-V), GROUP (3-W), CORE SEQUENCE (4), CORE SEQUENCE (4-N), CORE SEQUENCE (4-U), GROUP (4-S), GROUP (4-T), GROUP (4-V), CORE SEQUENCE (5), CORE SEQUENCE (5-N), CORE SEQUENCE (5-U), GROUP (5-S), GROUP (5-T), GROUP (5-V), GROUP (5-W), CORE SEQUENCE (6), CORE SEQUENCE (6-N), CORE SEQUENCE (6-U), GROUP (6-S), GROUP (6-T), GROUP (6-V), CORE SEQUENCE (7), CORE SEQUENCE (7-N), CORE SEQUENCE (7-U), GROUP (7-S), GROUP (7-T), GROUP (7-V), GROUP (7-W), CORE SEQUENCE (8), CORE SEQUENCE (8-N), CORE SEQUENCE (8-U), GROUP (8-S), GROUP (8-T), GROUP (8-V), SEQ ID NOS:001-069, (SEQ ID NOS:001-008, 010, 011, and 013-040), and (SEQ ID NOS:001-007, 010, 011, 013-029, and 031-040) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (1) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (1-N) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (1-U) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (1-S) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (1-V) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (2) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (2-N) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (2-U) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (2-S) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (2-T) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (2-V) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (3) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (3-N) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (3-U) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (3-S) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (3-T) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (3-V) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (3-W) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (4) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (4-N) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (4-U) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (4-S) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (4-T) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (4-V) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (5) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (5-N) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (5-U) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (5-S) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (5-T) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (5-V) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (5-W) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (6) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (6-N) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (6-U) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing.

In one embodiment, the invention embraces a method of treating inflammation in a patient in need thereof, comprising administering a composition comprising a therapeutically effective amount of one or more peptides selected from the group consisting of GROUP (6-S) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (6-T) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (6-V) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (7) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (7-N) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (7-U) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (7-S) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (7-T) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (7-V) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (7-W) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (8) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (8-N) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of CORE SEQUENCE (8-U) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (8-S) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (8-T) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of GROUP (8-V) to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of SEQ ID NOS:001 to 040 to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of SEQ ID NOS:001-008, 010, 011, and 013-040 to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating inflammation in a patient in need thereof, comprising administering a composition comprising a therapeutically effective amount of one or more peptides selected from the group consisting of SEQ ID NOS:041-069 to the patient. In one embodiment, the composition additionally comprises a pharmaceutically acceptable carrier. In one embodiment, the administration is topical application. In one embodiment, the administration is subcutaneous injection. In one embodiment, the administration is intravenous injection. In one embodiment, the inflammation is inflammation of the skin and dermis, inflammation of the eye, or inflammation due to wound healing. In one embodiment, the inflammation excludes inflammation of the skin and dermis, inflammation of the eye, and inflammation due to wound healing. In one embodiment, the inflammation is due to an autoimmune disorder; in additional embodiments, the autoimmune disorder is rheumatoid arthritis, multiple sclerosis, lupus, or amyotrophic lateral sclerosis (ALS). In one embodiment, the inflammation is due to a gastrointestinal disorder; in additional embodiments, the gastrointestinal disorder is inflammatory bowel disease, Crohn's disease, or colitis. In one embodiment, the inflammation is due to an infectious organism; in additional embodiments, the infectious organism is a bacterium, a virus, a fungus, or a parasite. In one embodiment, the inflammation is due to a neurodegenerative disease; in further embodiments, the neurodegenerative disease is Parkinson's Disease, Huntington's Disease, Alzheimer's Disease, amyotrophic lateral sclerosis, multiple sclerosis, traumatic brain injury, or stroke.

In one embodiment, the invention embraces a method of treating oral mucositis in a patient in need thereof, comprising administering a composition comprising a therapeutically effective amount of a compound which inhibits NF κB activation or inhibits NF κB activity. In a further embodiment, the composition comprises a therapeutically effective amount of one or more peptides selected from the group consisting of peptides of CORE SEQUENCE (1), CORE SEQUENCE (1-N), CORE SEQUENCE (1-U), GROUP (1-S), GROUP (1-T), GROUP (1-V), GROUP (1-W), CORE SEQUENCE (2), CORE SEQUENCE (2-N), CORE SEQUENCE (2-U), GROUP (2-S), GROUP (2-T), GROUP (2-V), CORE SEQUENCE (3), CORE SEQUENCE (3-N), CORE SEQUENCE (3-U), GROUP (3-S), GROUP (3-T), GROUP (3-V), GROUP (3-W), CORE SEQUENCE (4), CORE SEQUENCE (4-N), CORE SEQUENCE (4-U), GROUP (4-S), GROUP (4-T), GROUP (4-V), CORE SEQUENCE (5), CORE SEQUENCE (5-N), CORE SEQUENCE (5-U), GROUP (5-S), GROUP (5-T), GROUP (5-V), GROUP (5-W), CORE SEQUENCE (6), CORE SEQUENCE (6-N), CORE SEQUENCE (6-U), GROUP (6-S), GROUP (6-T), GROUP (6-V), CORE SEQUENCE (7), CORE SEQUENCE (7-N), CORE SEQUENCE (7-U), GROUP (7-S), GROUP (7-T), GROUP (7-V), GROUP (7-W), CORE SEQUENCE (8), CORE SEQUENCE (8-N), CORE SEQUENCE (8-U), GROUP (8-S), GROUP (8-T), GROUP (8-V), SEQ ID NOS:001-069, (SEQ ID NOS:001-008, 010, 011, and 013-040), and (SEQ ID NOS:001-007, 010, 011, 013-029, and 031-040) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (1) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (1-N) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (1-U) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (1-S) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (1-V) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (2) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (2-N) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (2-U) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (2-S) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (2-T) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (2-V) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (3) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (3-N) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (3-U) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (3-S) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (3-T) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (3-V) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (3-W) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (4) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (4-N) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (4-U) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (4-S) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (4-T) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (4-V) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (5) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (5-N) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (5-U) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (5-S) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (5-T) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (5-V) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (5-W) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (6) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (6-N) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (6-U) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (6-S) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (6-T) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (6-V) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (7) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (7-N) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (7-U) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (7-S) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (7-T) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (7-V) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (7-W) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (8) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (8-N) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of CORE SEQUENCE (8-U) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (8-S) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (8-T) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of GROUP (8-V) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of SEQ ID NOS:001 to 040 to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of SEQ ID NOS:001-008, 010, 011, and 013-040 to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral mucositis in a patient in need thereof, comprising administering a composition comprising a therapeutically effective amount of one or more peptides selected from the group consisting of SEQ ID NOS:041-069 to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of a compound which inhibits NF κB activation or inhibits NF κB activity. In a further embodiment, the composition comprises a therapeutically effective amount of one or more peptides selected from the group consisting of CORE SEQUENCE (1), CORE SEQUENCE (1-N), CORE SEQUENCE (1-U), GROUP (1-S), GROUP (1-T), GROUP (1-V), GROUP (1-W), CORE SEQUENCE (2), CORE SEQUENCE (2-N), CORE SEQUENCE (2-U), GROUP (2-S), GROUP (2-T), GROUP (2-V), CORE SEQUENCE (3), CORE SEQUENCE (3-N), CORE SEQUENCE (3-U), GROUP (3-S), GROUP (3-T), GROUP (3-V), GROUP (3-W), CORE SEQUENCE (4), CORE SEQUENCE (4-N), CORE SEQUENCE (4-U), GROUP (4-S), GROUP (4-T), GROUP (4-V), CORE SEQUENCE (5), CORE SEQUENCE (5-N), CORE SEQUENCE (5-U), GROUP (5-S), GROUP (5-T), GROUP (5-V), GROUP (5-W), CORE SEQUENCE (6), CORE SEQUENCE (6-N), CORE SEQUENCE (6-U), GROUP (6-S), GROUP (6-T), GROUP (6-V), CORE SEQUENCE (7), CORE SEQUENCE (7-N), CORE SEQUENCE (7-U), GROUP (7-S), GROUP (7-T), GROUP (7-V), GROUP (7-W), CORE SEQUENCE (8), CORE SEQUENCE (8-N), CORE SEQUENCE (8-U), GROUP (8-S), GROUP (8-T), GROUP (8-V), SEQ ID NOS:001-069, (SEQ ID NOS:001-008, 010, 011, and 013-040), and (SEQ ID NOS:001-007, 010, 011, 013-029, and 031-040), to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (1) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (1-N) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (1-U) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (1-S) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (1-V) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (2) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (2-N) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (2-U) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (2-S) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (2-T) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (2-V) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (3) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (3-N) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (3-U) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (3-S) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (3-T) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (3-V) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (3-W) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (4) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (4-N) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (4-U) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (4-S) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (4-T) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (4-V) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (5) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (5-N) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (5-U) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (5-S) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (5-T) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (5-V) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (5-W) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (6) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (6-N) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (6-U) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (6-S) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (6-T) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (6-V) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (7) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (7-N) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (7-U) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (7-S) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (7-T) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (7-V) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (7-W) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of a peptide of length seven to twenty residues comprising the sequence ANVAENA (SEQ ID NO:042) to the patient. In one embodiment, the invention embraces a method of treating oral cancer in a patient in need thereof, comprising administering a composition comprising a therapeutically effective amount of a peptide of length seven to fifteen residues comprising the sequence ANVAENA (SEQ ID NO:042) to the patient. In one embodiment, the invention embraces a method of treating oral cancer in a patient in need thereof, comprising administering a composition comprising a therapeutically effective amount of a peptide of length seven to twelve residues comprising the sequence ANVAENA (SEQ ID NO:042) to the patient. In one embodiment, the invention embraces a method of treating oral cancer in a patient in need thereof, comprising administering a composition comprising a therapeutically effective amount of the peptide of the sequence ANVAENA (SEQ ID NO:042) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (8) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (8-N) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of CORE SEQUENCE (8-U) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (8-S) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (8-T) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of GROUP (8-V) to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of SEQ ID NOS:001 to 040 to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of SEQ ID NOS:001-008, 010, 011, and 013-040 to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating oral cancer in a patient in need thereof, comprising administering a composition comprising a therapeutically effective amount of one or more peptides selected from the group consisting of SEQ ID NOS:041-069 to the patient. In one embodiment, the composition additionally comprises a pharmaceutical carrier suitable for administration in or to the oral cavity. In one embodiment, the administration is topical application. In one embodiment, the administration is subcutaneous injection.

In one embodiment, the invention embraces a method of treating a disease or disorder in a patient in need thereof, comprising administering a composition comprising a therapeutically effective amount of a compound which inhibits NF κB activation or inhibits NF κB activity. In a further embodiment, the composition comprises a therapeutically effective amount of one or more peptides selected from the group consisting of CORE SEQUENCE (1), CORE SEQUENCE (1-N), CORE SEQUENCE (1-U), GROUP (1-S), GROUP (1-T), GROUP (1-V), GROUP (1-W), CORE SEQUENCE (2), CORE SEQUENCE (2-N), CORE SEQUENCE (2-U), GROUP (2-S), GROUP (2-T), GROUP (2-V), CORE SEQUENCE (3), CORE SEQUENCE (3-N), CORE SEQUENCE (3-U), GROUP (3-S), GROUP (3-T), GROUP (3-V), GROUP (3-W), CORE SEQUENCE (4), CORE SEQUENCE (4-N), CORE SEQUENCE (4-U), GROUP (4-S), GROUP (4-T), GROUP (4-V), CORE SEQUENCE (5), CORE SEQUENCE (5-N), CORE SEQUENCE (5-U), GROUP (5-S), GROUP (5-T), GROUP (5-V), GROUP (5-W), CORE SEQUENCE (6), CORE SEQUENCE (6-N), CORE SEQUENCE (6-U), GROUP (6-S), GROUP (6-T), GROUP (6-V), CORE SEQUENCE (7), CORE SEQUENCE (7-N), CORE SEQUENCE (7-U), GROUP (7-S), GROUP (7-T), GROUP (7-V), GROUP (7-W), CORE SEQUENCE (8), CORE SEQUENCE (8-N), CORE SEQUENCE (8-U), GROUP (8-S), GROUP (8-T), GROUP (8-V), SEQ ID NOS:001-069, (SEQ ID NOS:001-008, 010, 011, and 013-040), and (SEQ ID NOS:001-007, 010, 011, 013-029, and 031-040), to the patient, where the disease or disorder is selected from the group consisting of ischemic diseases. In further embodiments, the ischemic disease is myocardial infarction, acute heart failure, chronic heart failure, cerebral infarction, or pulmonary infarction.

In one embodiment, the invention embraces a method of treating a disease or disorder in a patient in need thereof, comprising administering a composition comprising a therapeutically effective amount of a compound which inhibits NF κB activation or inhibits NF κB activity. In a further embodiment, the composition comprises a therapeutically effective amount of one or more peptides selected from the group consisting of CORE SEQUENCE (1), CORE SEQUENCE (1-N), CORE SEQUENCE (1-U), GROUP (1-S), GROUP (1-T), GROUP (1-V), GROUP (1-W), CORE SEQUENCE (2), CORE SEQUENCE (2-N), CORE SEQUENCE (2-U), GROUP (2-S), GROUP (2-T), GROUP (2-V), CORE SEQUENCE (3), CORE SEQUENCE (3-N), CORE SEQUENCE (3-U), GROUP (3-S), GROUP (3-T), GROUP (3-V), GROUP (3-W), CORE SEQUENCE (4), CORE SEQUENCE (4-N), CORE SEQUENCE (4-U), GROUP (4-S), GROUP (4-T), GROUP (4-V), CORE SEQUENCE (5), CORE SEQUENCE (5-N), CORE SEQUENCE (5-U), GROUP (5-S), GROUP (5-T), GROUP (5-V), GROUP (5-W), CORE SEQUENCE (6), CORE SEQUENCE (6-N), CORE SEQUENCE (6-U), GROUP (6-S), GROUP (6-T), GROUP (6-V), CORE SEQUENCE (7), CORE SEQUENCE (7-N), CORE SEQUENCE (7-U), GROUP (7-S), GROUP (7-T), GROUP (7-V), GROUP (7-W), CORE SEQUENCE (8), CORE SEQUENCE (8-N), CORE SEQUENCE (8-U), GROUP (8-S), GROUP (8-T), GROUP (8-V), SEQ ID NOS:001-069, (SEQ ID NOS:001-008, 010, 011, and 013-040), and (SEQ ID NOS:001-007, 010, 011, 013-029, and 031-040), to the patient, where the disease or disorder is selected from the group consisting of mucocutaneous diseases. In further embodiments, the disease or disorder is an erythematous, ulcerative, inflammatory, necrotic or erosive dysplasia of muco-cutaneous surfaces, such as those in the oral cavity, the nasal cavity, the gastrointestinal and respiratory tracts, the vagina, and the bladder; mucositis, oral mucositis, denture stomatitis, oral lichen planus, aphthous ulcers, pemphigus, bullous pemphigoid, oral lichen planus, oral mucous membrane contact dermatitis, herpetiform ulcers, canker sores, digestive mucositis, esophageal mucositis, intestinal mucositis, inflammatory bowel disease, ulcerative colitis, Crohn's disease, aphthous ulcers, pemphigus, bullous pemphigoid, oral lichen planus, oral mucous membrane contact dermatitis, herpetiform ulcers, canker sores, diseases of the nasal mucous membrane include sinusitis and rhinitis, interstitial cystitis. radiation cystitis, mucocutaneous complications of Behcet syndrome, radiation-induced mucositis, radiation-induced esophagitis, radiation proctitis, or mucosal injury from endoscopic procedures.

In one embodiment, the invention embraces a method of treating a disease or disorder in a patient in need thereof, comprising administering a composition comprising a therapeutically effective amount of a compound which inhibits NF κB activation or inhibits NF κB activity. In a further embodiment, the composition comprises a therapeutically effective amount of one or more peptides selected from the group consisting of CORE SEQUENCE (1), CORE SEQUENCE (1-N), CORE SEQUENCE (1-U), GROUP (1-S), GROUP (1-T), GROUP (1-V), GROUP (1-W), CORE SEQUENCE (2), CORE SEQUENCE (2-N), CORE SEQUENCE (2-U), GROUP (2-S), GROUP (2-T), GROUP (2-V), CORE SEQUENCE (3), CORE SEQUENCE (3-N), CORE SEQUENCE (3-U), GROUP (3-S), GROUP (3-T), GROUP (3-V), GROUP (3-W), CORE SEQUENCE (4), CORE SEQUENCE (4-N), CORE SEQUENCE (4-U), GROUP (4-S), GROUP (4-T), GROUP (4-V), CORE SEQUENCE (5), CORE SEQUENCE (5-N), CORE SEQUENCE (5-U), GROUP (5-S), GROUP (5-T), GROUP (5-V), GROUP (5-W), CORE SEQUENCE (6), CORE SEQUENCE (6-N), CORE SEQUENCE (6-U), GROUP (6-S), GROUP (6-T), GROUP (6-V), CORE SEQUENCE (7), CORE SEQUENCE (7-N), CORE SEQUENCE (7-U), GROUP (7-S), GROUP (7-T), GROUP (7-V), GROUP (7-W), CORE SEQUENCE (8), CORE SEQUENCE (8-N), CORE SEQUENCE (8-U), GROUP (8-S), GROUP (8-T), GROUP (8-V), SEQ ID NOS:001-069, (SEQ ID NOS:001-008, 010, 011, and 013-040), and (SEQ ID NOS:001-007, 010, 011, 013-029, and 031-040), to the patient, where the disease or disorder is selected from the group consisting of inflammatory diseases. In further embodiments, the disease or disorder is Acne, Ankylosing spondylitis, Barrett's esophagus, Chronic fatigue syndrome (CFS/CFIDS/ME), Chronic Lyme disease (borreliosis), Crohn's disease, Diabetes, Depression, Dermatitis, Fascitis, Fibromyalgia (FM), Gastroesophageal reflux disease (GERD), Gingivitis, Hashimoto's thyroiditis, Hypertension, Hyperthyroidism, Hypothyroidism, Irritable Bowel Syndrome (IBS), Interstitial cystitis (IC), Kidney stones, Lofgren's syndrome, Lupus erythematosus, Multiple Chemical Sensitivity (MCS), Migraine headache, Morgellon's, Multiple sclerosis, Osteoarthritis, Periodontitis, Polymyalgia rheumatica, Prostatitis, Psoriasis, Psoriatic arthritis, Raynaud's syndrome/phenomenon, Reactive arthritis (Reiter syndrome), Restless leg syndrome, Reflex Sympathetic Dystrophy (RSD), Rheumatoid arthritis, Sarcoidosis, Scleroderma, Sinusitis, Seasonal affective disorder (SAD), Sjögren's syndrome, Stomatitis, Tendonitis, Ulcerative colitis, Urticaria, Uveitis, or Vertigo.

In one embodiment, the invention embraces a method of treating a disease or disorder in a patient in need thereof, comprising administering a composition comprising a therapeutically effective amount of a compound which inhibits NF κB activation or inhibits NF κB activity. In a further embodiment, the composition comprises a therapeutically effective amount of one or more peptides selected from the group consisting of CORE SEQUENCE (1), CORE SEQUENCE (1-N), CORE SEQUENCE (1-U), GROUP (1-S), GROUP (1-T), GROUP (1-V), GROUP (1-W), CORE SEQUENCE (2), CORE SEQUENCE (2-N), CORE SEQUENCE (2-U), GROUP (2-S), GROUP (2-T), GROUP (2-V), CORE SEQUENCE (3), CORE SEQUENCE (3-N), CORE SEQUENCE (3-U), GROUP (3-S), GROUP (3-T), GROUP (3-V), GROUP (3-W), CORE SEQUENCE (4), CORE SEQUENCE (4-N), CORE SEQUENCE (4-U), GROUP (4-S), GROUP (4-T), GROUP (4-V), CORE SEQUENCE (5), CORE SEQUENCE (5-N), CORE SEQUENCE (5-U), GROUP (5-S), GROUP (5-T), GROUP (5-V), GROUP (5-W), CORE SEQUENCE (6), CORE SEQUENCE (6-N), CORE SEQUENCE (6-U), GROUP (6-S), GROUP (6-T), GROUP (6-V), CORE SEQUENCE (7), CORE SEQUENCE (7-N), CORE SEQUENCE (7-U), GROUP (7-S), GROUP (7-T), GROUP (7-V), GROUP (7-W), CORE SEQUENCE (8), CORE SEQUENCE (8-N), CORE SEQUENCE (8-U), GROUP (8-S), GROUP (8-T), GROUP (8-V), SEQ ID NOS:001-069, (SEQ ID NOS:001-008, 010, 011, and 013-040), and (SEQ ID NOS:001-007, 010, 011, 013-029, and 031-040), to the patient, where the disease or disorder is selected from the group consisting of fibrotic diseases and scarring. In further embodiments, the disease or disorder is fibrosis, scarring after incision or surgery, scarring after burning, or adhesions after incisions or surgery.

In one embodiment, the invention embraces a method of treating a disease or disorder in a patient in need thereof, comprising administering a composition comprising a therapeutically effective amount of a compound which inhibits NF κB activation or inhibits NF κB activity. In a further embodiment, the composition comprises a therapeutically effective amount of one or more peptides selected from the group consisting of CORE SEQUENCE (1), CORE SEQUENCE (1-N), CORE SEQUENCE (1-U), GROUP (1-S), GROUP (1-T), GROUP (1-V), GROUP (1-W), CORE SEQUENCE (2), CORE SEQUENCE (2-N), CORE SEQUENCE (2-U), GROUP (2-S), GROUP (2-T), GROUP (2-V), CORE SEQUENCE (3), CORE SEQUENCE (3-N), CORE SEQUENCE (3-U), GROUP (3-S), GROUP (3-T), GROUP (3-V), GROUP (3-W), CORE SEQUENCE (4), CORE SEQUENCE (4-N), CORE SEQUENCE (4-U), GROUP (4-S), GROUP (4-T), GROUP (4-V), CORE SEQUENCE (5), CORE SEQUENCE (5-N), CORE SEQUENCE (5-U), GROUP (5-S), GROUP (5-T), GROUP (5-V), GROUP (5-W), CORE SEQUENCE (6), CORE SEQUENCE (6-N), CORE SEQUENCE (6-U), GROUP (6-S), GROUP (6-T), GROUP (6-V), CORE SEQUENCE (7), CORE SEQUENCE (7-N), CORE SEQUENCE (7-U), GROUP (7-S), GROUP (7-T), GROUP (7-V), GROUP (7-W), CORE SEQUENCE (8), CORE SEQUENCE (8-N), CORE SEQUENCE (8-U), GROUP (8-S), GROUP (8-T), GROUP (8-V), SEQ ID NOS:001-069, (SEQ ID NOS:001-008, 010, 011, and 013-040), and (SEQ ID NOS:001-007, 010, 011, 013-029, and 031-040), to the patient, where the disease or disorder is selected from the group consisting of cancers. In further embodiments, the cancer is a lymphoproliferative disorder, a lymphoma, a leukemia, a carcinoma, a sarcoma, prostate cancer, breast cancer, cervical cancer, uterine cancer, endometrial cancer, bone cancer, gastric cancer, colon cancer, liver cancer, pancreatic cancer, various head and neck cancers, thyroid cancer, cancer of the central nervous system, cancer of the peripheral nervous system, brain cancer, kidney cancer, skin cancer, oral cancer, or an oral tumor.

In one embodiment, the invention embraces a method of treating a disease or disorder in a patient in need thereof, comprising administering a composition comprising a therapeutically effective amount of a compound which inhibits NF κB activation or inhibits NF κB activity. In a further embodiment, the composition comprises a therapeutically effective amount of one or more peptides selected from the group consisting of CORE SEQUENCE (1), CORE SEQUENCE (1-N), CORE SEQUENCE (1-U), GROUP (1-S), GROUP (1-T), GROUP (1-V), GROUP (1-W), CORE SEQUENCE (2), CORE SEQUENCE (2-N), CORE SEQUENCE (2-U), GROUP (2-S), GROUP (2-T), GROUP (2-V), CORE SEQUENCE (3), CORE SEQUENCE (3-N), CORE SEQUENCE (3-U), GROUP (3-S), GROUP (3-T), GROUP (3-V), GROUP (3-W), CORE SEQUENCE (4), CORE SEQUENCE (4-N), CORE SEQUENCE (4-U), GROUP (4-S), GROUP (4-T), GROUP (4-V), CORE SEQUENCE (5), CORE SEQUENCE (5-N), CORE SEQUENCE (5-U), GROUP (5-S), GROUP (5-T), GROUP (5-V), GROUP (5-W), CORE SEQUENCE (6), CORE SEQUENCE (6-N), CORE SEQUENCE (6-U), GROUP (6-S), GROUP (6-T), GROUP (6-V), CORE SEQUENCE (7), CORE SEQUENCE (7-N), CORE SEQUENCE (7-U), GROUP (7-S), GROUP (7-T), GROUP (7-V), GROUP (7-W), CORE SEQUENCE (8), CORE SEQUENCE (8-N), CORE SEQUENCE (8-U), GROUP (8-S), GROUP (8-T), GROUP (8-V), SEQ ID NOS:001-069, (SEQ ID NOS:001-008, 010, 011, and 013-040), and (SEQ ID NOS:001-007, 010, 011, 013-029, and 031-040), to the patient, where the disease or disorder is selected from the group consisting of an age-associated disease or disorder.

In one embodiment, the invention embraces a method of treating a disease or disorder in a patient in need thereof, comprising administering a composition comprising a therapeutically effective amount of a compound which inhibits NF κB activation or inhibits NF κB activity. In a further embodiment, the composition comprises a therapeutically effective amount of one or more peptides selected from the group consisting of CORE SEQUENCE (1), CORE SEQUENCE (1-N), CORE SEQUENCE (1-U), GROUP (1-S), GROUP (1-T), GROUP (1-V), GROUP (1-W), CORE SEQUENCE (2), CORE SEQUENCE (2-N), CORE SEQUENCE (2-U), GROUP (2-S), GROUP (2-T), GROUP (2-V), CORE SEQUENCE (3), CORE SEQUENCE (3-N), CORE SEQUENCE (3-U), GROUP (3-S), GROUP (3-T), GROUP (3-V), GROUP (3-W), CORE SEQUENCE (4), CORE SEQUENCE (4-N), CORE SEQUENCE (4-U), GROUP (4-S), GROUP (4-T), GROUP (4-V), CORE SEQUENCE (5), CORE SEQUENCE (5-N), CORE SEQUENCE (5-U), GROUP (5-S), GROUP (5-T), GROUP (5-V), GROUP (5-W), CORE SEQUENCE (6), CORE SEQUENCE (6-N), CORE SEQUENCE (6-U), GROUP (6-S), GROUP (6-T), GROUP (6-V), CORE SEQUENCE (7), CORE SEQUENCE (7-N), CORE SEQUENCE (7-U), GROUP (7-S), GROUP (7-T), GROUP (7-V), GROUP (7-W), CORE SEQUENCE (8), CORE SEQUENCE (8-N), CORE SEQUENCE (8-U), GROUP (8-S), GROUP (8-T), GROUP (8-V), SEQ ID NOS:001-069, (SEQ ID NOS:001-008, 010, 011, and 013-040), and (SEQ ID NOS:001-007, 010, 011, 013-029, and 031-040), to the patient, where the disease or disorder is selected from the group consisting of a disease or disorder associated with ageing of skin.

In one embodiment, the invention embraces a method of treating a disease or disorder in a patient in need thereof, comprising administering a composition comprising a therapeutically effective amount of a compound which inhibits NF κB activation or inhibits NF κB activity. In a further embodiment, the composition comprises a therapeutically effective amount of one or more peptides selected from the group consisting of CORE SEQUENCE (1), CORE SEQUENCE (1-N), CORE SEQUENCE (1-U), GROUP (1-S), GROUP (1-T), GROUP (1-V), GROUP (1-W), CORE SEQUENCE (2), CORE SEQUENCE (2-N), CORE SEQUENCE (2-U), GROUP (2-S), GROUP (2-T), GROUP (2-V), CORE SEQUENCE (3), CORE SEQUENCE (3-N), CORE SEQUENCE (3-U), GROUP (3-S), GROUP (3-T), GROUP (3-V), GROUP (3-W), CORE SEQUENCE (4), CORE SEQUENCE (4-N), CORE SEQUENCE (4-U), GROUP (4-S), GROUP (4-T), GROUP (4-V), CORE SEQUENCE (5), CORE SEQUENCE (5-N), CORE SEQUENCE (5-U), GROUP (5-S), GROUP (5-T), GROUP (5-V), GROUP (5-W), CORE SEQUENCE (6), CORE SEQUENCE (6-N), CORE SEQUENCE (6-U), GROUP (6-S), GROUP (6-T), GROUP (6-V), CORE SEQUENCE (7), CORE SEQUENCE (7-N), CORE SEQUENCE (7-U), GROUP (7-S), GROUP (7-T), GROUP (7-V), GROUP (7-W), CORE SEQUENCE (8), CORE SEQUENCE (8-N), CORE SEQUENCE (8-U), GROUP (8-S), GROUP (8-T), GROUP (8-V), SEQ ID NOS:001-069, (SEQ ID NOS:001-008, 010, 011, and 013-040), and (SEQ ID NOS:001-007, 010, 011, 013-029, and 031-040), to the patient, where the disease or disorder is pain.

In one embodiment, the invention embraces a method of treating a disease or disorder in a patient in need thereof, comprising administering a composition comprising a therapeutically effective amount of a compound which inhibits NF κB activation or inhibits NF κB activity. In a further embodiment, the composition comprises a therapeutically effective amount of one or more peptides selected from the group consisting of CORE SEQUENCE (1), CORE SEQUENCE (1-N), CORE SEQUENCE (1-U), GROUP (1-S), GROUP (1-T), GROUP (1-V), GROUP (1-W), CORE SEQUENCE (2), CORE SEQUENCE (2-N), CORE SEQUENCE (2-U), GROUP (2-S), GROUP (2-T), GROUP (2-V), CORE SEQUENCE (3), CORE SEQUENCE (3-N), CORE SEQUENCE (3-U), GROUP (3-S), GROUP (3-T), GROUP (3-V), GROUP (3-W), CORE SEQUENCE (4), CORE SEQUENCE (4-N), CORE SEQUENCE (4-U), GROUP (4-S), GROUP (4-T), GROUP (4-V), CORE SEQUENCE (5), CORE SEQUENCE (5-N), CORE SEQUENCE (5-U), GROUP (5-S), GROUP (5-T), GROUP (5-V), GROUP (5-W), CORE SEQUENCE (6), CORE SEQUENCE (6-N), CORE SEQUENCE (6-U), GROUP (6-S), GROUP (6-T), GROUP (6-V), CORE SEQUENCE (7), CORE SEQUENCE (7-N), CORE SEQUENCE (7-U), GROUP (7-S), GROUP (7-T), GROUP (7-V), GROUP (7-W), CORE SEQUENCE (8), CORE SEQUENCE (8-N), CORE SEQUENCE (8-U), GROUP (8-S), GROUP (8-T), GROUP (8-V), SEQ ID NOS:001-069, (SEQ ID NOS:001-008, 010, 011, and 013-040), and (SEQ ID NOS:001-007, 010, 011, 013-029, and 031-040), to the patient, where the disease or disorder is radiation injury or a sequela of radiation exposure. In one embodiment, the sequela of radiation exposure excludes mucositis.

In a further embodiment, the invention embraces a composition for use in treating any of the diseases or disorders disclosed herein, the use of a composition for treating any of the diseases or disorders disclosed herein, or the use of a composition for the manufacture of a medicament for treating any of the diseases and disorders disclosed herein, comprising administering a composition comprising a therapeutically effective amount of a compound which inhibits NF κB activation or inhibits NF κB activity. In a further embodiment, the composition comprises one or more peptides selected from the group consisting of CORE SEQUENCE (1), CORE SEQUENCE (1-N), CORE SEQUENCE (1-U), GROUP (1-S), GROUP (1-T), GROUP (1-V), GROUP (1-W), CORE SEQUENCE (2), CORE SEQUENCE (2-N), CORE SEQUENCE (2-U), GROUP (2-S), GROUP (2-T), GROUP (2-V), CORE SEQUENCE (3), CORE SEQUENCE (3-N), CORE SEQUENCE (3-U), GROUP (3-S), GROUP (3-T), GROUP (3-V), GROUP (3-W), CORE SEQUENCE (4), CORE SEQUENCE (4-N), CORE SEQUENCE (4-U), GROUP (4-S), GROUP (4-T), GROUP (4-V), CORE SEQUENCE (5), CORE SEQUENCE (5-N), CORE SEQUENCE (5-U), GROUP (5-S), GROUP (5-T), GROUP (5-V), GROUP (5-W), CORE SEQUENCE (6), CORE SEQUENCE (6-N), CORE SEQUENCE (6-U), GROUP (6-S), GROUP (6-T), GROUP (6-V), CORE SEQUENCE (7), CORE SEQUENCE (7-N), CORE SEQUENCE (7-U), GROUP (7-S), GROUP (7-T), GROUP (7-V), GROUP (7-W), CORE SEQUENCE (8), CORE SEQUENCE (8-N), CORE SEQUENCE (8-U), GROUP (8-S), GROUP (8-T), GROUP (8-V), SEQ ID NOS:001-069, (SEQ ID NOS:001-008, 010, 011, and 013-040), and (SEQ ID NOS:001-007, 010, 011, 013-029, and 031-040).

Some embodiments described herein are recited as "comprising" or "comprises" with respect to their various elements. In alternative embodiments, those elements can be recited with the transitional phrase "consisting essentially of" or "consists essentially of" as applied to those elements. In further alternative embodiments, those elements can be recited with the transitional phrase "consisting of" or "consists of" as applied to those elements. Thus, for example, if a composition or method is disclosed herein as comprising A and B, the alternative embodiment for that composition or method of "consisting essentially of A and B" and the alternative embodiment for that composition or method of "consisting of A and B" are also considered to have been disclosed herein. Likewise, embodiments recited as "consisting essentially of" or "consisting of" with respect to their various elements can also be recited as "comprising" as applied to those elements. Finally, embodiments recited as "consisting essentially of" with respect to their various elements can also be recited as "consisting of" as applied to those elements, and embodiments recited as "consisting of" with respect to their various elements can also be recited as "consisting essentially of" as applied to those elements.

When a composition is described as "consisting essentially of" the listed components, the composition contains the components expressly listed, and may contain other components which do not substantially affect the condition being treated such as inert excipients or carriers. However, the composition either does not contain any other components which do substantially affect the condition being treated other than those components expressly listed; or, if the composition does contain extra components other than those listed which substantially affect the condition being treated, the composition does not contain a sufficient concentration or amount of those extra components to substantially affect the condition being treated. When a method is described as "consisting essentially of" the listed steps, the method contains the steps listed, and may contain other steps that do not substantially affect the condition being treated, but the method does not contain any other steps which substantially affect the condition being treated other than those steps expressly listed.

The compositions and methods described herein, including any embodiment of the invention as described herein, may be used alone or may be used in combination with other compositions and methods.

BRIEF DESCRIPTION OF THE DRAWINGS

FIG. 5A shows a control animal. FIG. 5B shows an induced tumor in the hamster cheek. FIG. 5C shows the marked regression of the tumor after topical application of peptide inhibitor of NF κB, ANVAENA (SEQ ID NO:042), for six weeks.

FIG. 6A, FIG. 6B, and FIG. 6C show microscopic examination of a tumor produced by DMBA application and treated with NF κB inhibitor peptide NVAENA (SEQ ID NO: 010) as in FIG. 5. FIG. 6A shows untreated control tissue. FIG. 6B shows tissue treated with DMBA (i.e., tumor tissue). FIG. 6C shows tissue treated with DMBA, then treated with NF κB inhibitor peptide as in FIG. 5, showing that the histology is closer to normal histology after treatment.

FIG. 7 shows various NF-κB target genes, which are involved in numerous pathological processes, and expression of which contributes to a wide range of diseases. Suppression of these genes by inhibiting the activation of NF-κB can be expected to contribute to the prevention and treatment of diseases arising from the excessive production of these genes and their products. These genes may be affected or downregulated by NF κB inhibitor peptide NVAENA (SEQ ID NO: 010).

FIG. 8A and FIG. 8B show disclosed peptides for use in inhibiting NF κB activity. FIG. 8A shows SEQ IDS NOS: 001 through 040. SEQ IDS NOS:009 and 012 are peptides disclosed in U.S. Pat. Nos. 5,661,127, 5,780,436; and 6,638, 912. FIG. 8B shows SEQ IDS NOS:041 through 069, which are peptides disclosed in U.S. Pat. Nos. 5,661,127, 5,780, 436; and 6,638,912. FIG. 8C shows SEQ ID NOS:070 through 113, which are peptides disclosed in U.S. Patent Application Publication No. 2006/0293228.

FIG. 9A lists the naturally-occurring (proteinogenic) encoded amino acids. FIG. 9B lists unnatural and/or non-encoded (non-proteinogenic) amino acids.

DETAILED DESCRIPTION

Figure 1A:
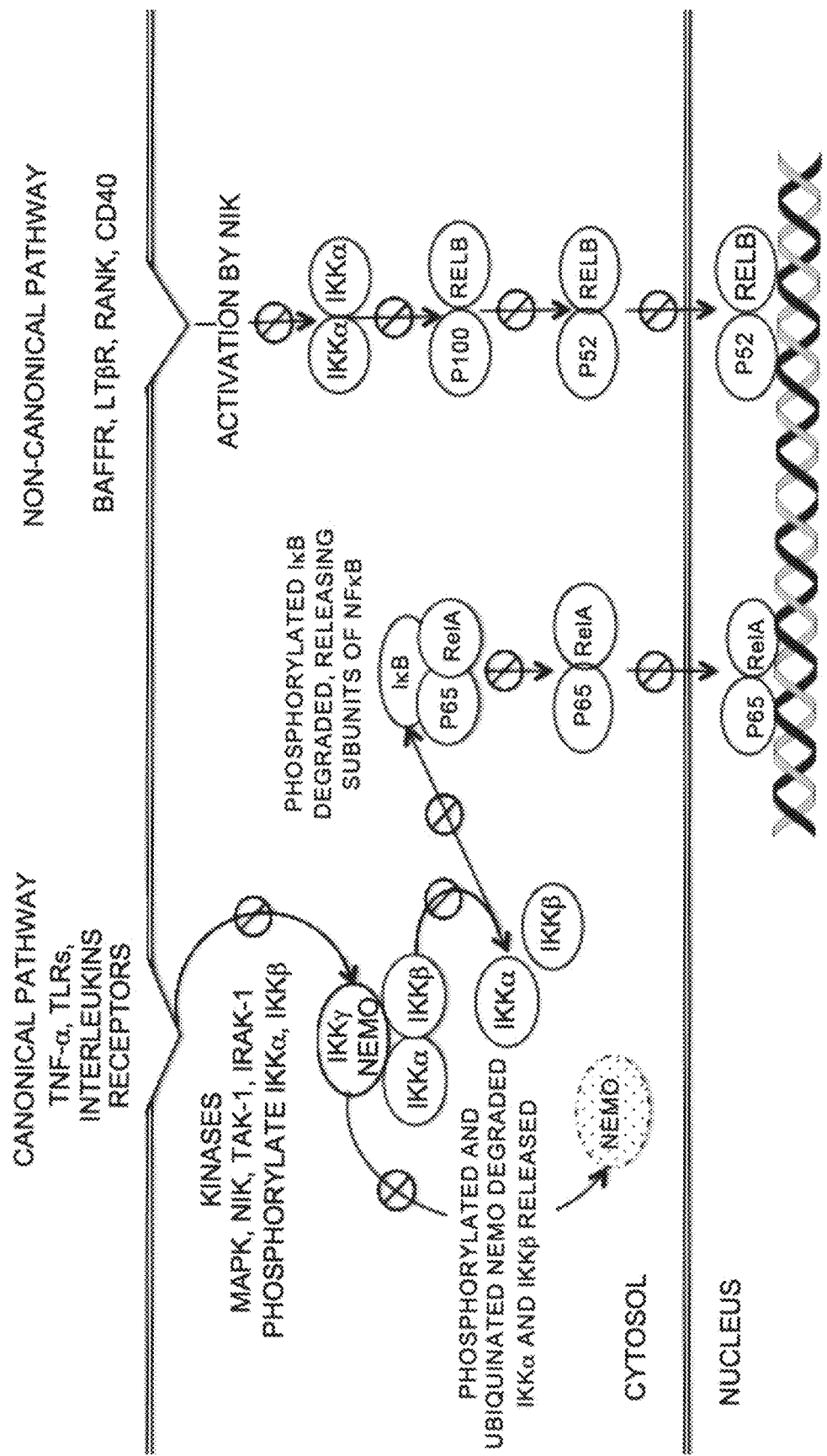
FIG. 1A shows a diagrammatic representation of potential steps in the activation pathway of NF κB which may be inhibited by the disclosed peptides. The inhibited steps are depicted by a circle with a  slash through it.

The invention described herein pertains to prevention or treatment of diseases and disorders that involve perturbations in the normal homeostasis of the transcription factor NF κB.

Perturbations in the normal homeostasis of the transcription factor NF κB are induced by over 150 stimuli, including free radicals, exposure to UV, ionizing radiation, inflammation, physico-chemical stress, infection, and injury. Currently used cytotoxic agents can induce NF κB activation as an unwarranted side effect, which confers apoptosis suppression and hence resistance to these drugs. Thus, NF κB inhibitory molecules may be clinically useful, either as single therapeutic agents or in combination with classical chemotherapeutic agents. "NF κB activation" can refer to translocation of NF kB to the nucleus, and/or the subsequent modulation of genes which are directly or indirectly under the control of an NF κB binding site. In functional terms, NF κB activation comprises the binding of NF κB to KB regulatory sequences in the DNA of a cell, so that transcription of the operatively associated gene is induced (other factors acting in combination with NF κB may be required to initiate transcription).

Active NF κB, in turn, participates in the control of transcription of over 150 target genes. Because a large variety of bacteria and viruses activate NF κB and because the transcription factor regulates the expression of inflammatory cytokines, chemokines, immunoreceptors, and cell adhesion molecules, NF κB has often been termed a central mediator of the human immune response. The collected data argue that NF κB functions more generally as a central regulator of stress responses. In addition, NF κB activation blocks apoptosis in several cell types. Coupling stress responsiveness and anti-apoptotic pathways through the use of a common transcription factor may result in increased cell survival following stress insults.

NF κB is an ubiquitously expressed transcription factor that controls the expression of a diverse range of genes involved in inflammation, immune response, lymphoid differentiation, growth control and development. The majority of NF κB controlled genes are considered cell stress responders and lead to inflammation, apoptosis, and cellular growth/expansion. NF κB and Wnt pathways are major components of the molecular pathology of mucositis. These pathways are molecular targets of the peptides disclosed herein. The disclosed peptides are stereo-allomers of certain common conformational epitopes naturally present in signaling enzymes, serine-threonine kinases, tyrosine kinases, and receptor kinases. The disclosed peptides mimic structural features of these kinases and participate in their allosteric modulation. The disclosed peptides act as molecular decoys and influence interactions between protein kinases and their substrates.

NF κB occurs as a homo- or hetero-dimer of five related proteins, p50, p52, p65 (RelA), c-Rel, and RelB. The most common active dimers are p50/RelA or p52/RelA heterodimers. Dimeric NF κB exists as part of an inactive complex with inhibitor proteins called IκB in the cytoplasm. The IκB proteins, p105, p100, IκBa, IκBb, IκBg, IκBe, IκBz, and Bcl-3 have different affinities for individual Rel/NF κB complexes, are regulated slightly differently, and are expressed in a tissue-specific manner. In order for NF κB to be activated, the inhibitory IκB protein must be dissociated from the inactive complex. This is achieved by the phosphorylation of IκB, and its subsequent ubiquitination and degradation in the proteasome. IκB becomes phosphorylated and degraded in response to various environmental stimuli, such as pro-inflammatory cytokines, viruses, lipopolysaccharides, oxidants, UV light and ionizing radiation.

The majority of the genes under NF κB transcriptional control are involved in immune signaling and inflammatory responses. Indeed, transcriptional control of cytokine expression by NF κB is likely one of the most important factors when evaluating the role of NF κB in pathologic states. Some of these cytokines include TNFα, IL-1α/β, IL-2, 3, 6, 12, GM-CSF, M-CSF, and G-CSF. NF κB also regulates expression of chemokines (MCP-1, KC, MIP-1 and several CCLs) and adhesion molecules (ICAM-1, E-selectin, and VCAM-1), which allow for the recruitment and attachment of immune cells to sites of inflammation. Furthermore, NF κB upregulates the expression of receptors (CD80/81, IL-2Rα chain, TLR-2) and proteins involved in antigen presentation (MHC class I and J2 microglobulin) on immune cells, allowing for proper innate and adaptive immune responses. Recently, NF κB has been shown to have an anti-apoptotic role in certain cell types, most likely by inducing the expression of anti-apoptotic genes. This function may protect tumor cells against anti-cancer treatments and opens the possibility to use NF κB inhibiting compounds to sensitize the tumor cells and to improve the efficiency of the anti-cancer treatment.

Disturbances in signaling by the NF κB and the wnt pathways play a critical role in disease. Signaling depends on protein phosphorylation catalyzed by serine threonine kinases and tyrosine kinases, together referred to as protein kinases. Protein kinases modify protein function by transferring phosphate groups from adenosine triphosphate (ATP) or guanosine triphosphate (GTP) to free hydroxyl groups of amino acids serine, threonine, and tyrosine. Protein kinases play crucial roles in signal transduction cascades: from controlling cell differentiation, growth and proliferation to the initiation and regulation of immunological responses. Aberrant kinase activity is implicated in an increasing number of diseases, with more than 400 human diseases now linked either directly or indirectly to protein kinases. Protein kinases are therefore regarded as highly important drug targets.

The structures of tyrosine kinases and serine threonine kinases are highly conserved. Serine threonine kinases possess multiple interactive sites that play distinct roles in intermolecular recognition, interaction and binding, and catalysis. Serine threonine kinase activity is modulated by allosteric mechanisms. Allosteric modulators provide a way to modulate natural regulation (amplify a naturally regulated response) rather than completely inhibit or continuously activate proteins.

Peptides can mimic protein-protein interactions. They provide a powerful means to regulate signaling events. The disclosed peptides mimic protein domains involved in the interaction of kinases and participate in allosteric modulation of these kinases. The disclosed peptides act as molecular decoys and influence interactions between protein kinases and their substrates. The disclosed peptides are allosteric modulators. They may act by inducing conformational change by interacting with specific host sites on some serine threonine kinases thereby activating them. As conformational decoys, the disclosed peptides are hypothesized to compete for interaction between certain key serine threonine kinases and their substrates. The disclosed peptides disrupt interactions between substrate binding and docking sites. The disclosed peptides dissociate the interactions between IKK-2 from an IKK complex and interfere with the interaction of NEMO-IKK-2. The peptides inhibit IKK-2 phosphorylation. This results in the inhibition of phosphorylation of p65 and inhibitor of IκB. These results are seen in FIG. 1-4. FIG. 1A shows a diagrammatic representation of inhibition by the disclosed peptides of steps in the activation pathway of NF κB. In silico studies show that the disclosed peptides may dock in interactive sites of certain serine threonine kinases, precluding the interaction of the enzyme with its substrate and inhibiting key enzymatic steps in the NF-κB activation pathway. These potentially inhibited pathways are shown in FIG. 1A, where the circles containing a slash show potential steps that may be inhibited by the peptides. Experimentally, the inhibition is observed as a decrease in the level of NF-κB activation (see FIG. 2 and FIG. 3), and as decreased phosphorylation of NF-κB subunits (see Example 2). The postulated overall mechanism of inhibition of NF-κB is described schematically based on these observations. Over 150 stimuli cause activation of NF κB. NF κB dimers are present in the cytoplasm as inactive complexes with IKB proteins which must be phosphorylated by specific IKB kinases, IKKα and IKKβ. IKKα and IKKβ are themselves present in inhibited complexes and are activated by stimulus induced kinases. Three of these, NIK, TAK1 and MEKK3 are shown in the diagram. The disclosed peptides may act as decoys for substrates and inhibit the kinases. The inhibition sites are depicted by block arrows. The abbreviations used in FIG. 1A are as follows: BAFFR: B-cell activating factor receptor; CD40: CD40 Antigen (TNF Receptor Superfamily Member 5); IκB: Nuclear Factor Of Kappa Light Polypeptide Gene Enhancer In B-Cells Inhibitor, Beta; IKKα: Nuclear Factor NFkappaB Inhibitor Kinase Alpha; IKKβ: Nuclear Factor NFkappaB Inhibitor Kinase Beta; IKKγ: (NEMO) Inhibitor Of Kappa Light Polypeptide Gene Enhancer In B-Cells Kinase Gamma; IRAK-1: Interleukin-1 Receptor-Associated Kinase 1; LTβR: Lymphotoxin Beta Receptor (TNFR Superfamily, Member 3); MAPK: Mitogen-Activated Protein Kinase; NIK: NF-Kappa-Beta-Inducing Kinase; P100: Nuclear Factor NF-Kappa-B P100 Subunit; P52: Nuclear Factor NF-Kappa-B P52 Subunit; P65: Nuclear Factor NF-Kappa-B P65 Subunit; RANK: Receptor Activator Of NF-κB; RelA: Nuclear Factor NF-Kappa-B P65 Subunit; RELB: Transcription Factor RelB; TAK-1: TGF-Beta Activated Kinase 1; TLR: Toll-Like Receptor; TNF-α: Tumor Necrosis Factor-Alpha.

The phosphorylation of the p65 NF-κB subunit provides a convenient assay for NF-κB activity. Such assays are described in Moreno et al., Nucleic Acids Research, 38(18): 6029-6044 (2010) and Wang et al., PLoS ONE Vol. 7, Issue 3, e34122 (2012). The Cellular Activation of Signaling ELISA (CASE™) Kit, available from SABiosciences Corporation, Frederick, Maryland and the NFkB p65 (Total/Phospho) InstantOne™ ELISA Kit, available from eBioscience, San Diego, California; or the NF kappaB p65 (total) ELISA Kit (Catalog No. KH00371) available from ThermoFisher Scientific, Waltham, Massachusetts, can be used to quantitate phosphorylated NF-κB p65. A decrease in the amount of phosphorylated NF-κB p65 indicates inhibition of NF-κB activity.

Figures 1B, 2:
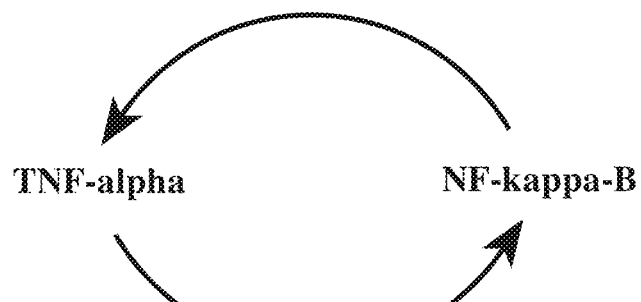
FIG. 1B shows a positive feedback loop for TNF-α activation of NF-κB.
FIG. 2 shows the inhibition by several of the disclosed peptides, of the activation of NF κB by TNF α.

Activation of NF κB allows the transcription factor to translocate in the nucleus and interaction with specific genomic sites results in the expression of genes that contribute to disease. These genes include chemokines, interleukins, TNF a and the receptors for these deleterious proteins amongst numerous other proteins. Thus, inhibition of the activation of NF κB by the disclosed peptides would also prevent further disorders that would be caused by the chemokines, cytokines, TNF α, and their related receptor proteins. Since these molecules also contribute to the activation of NF κB, it can be seen how the disclosed peptides which inhibit NF κB activation may stop a self-sustaining feedback system. Such a positive feedback system is illustrated in FIG. 1B.

TGF-β is a negative regulator of the cell cycle leading to growth arrest by directly affecting the cell cycle. TGF-β binding induces the formation of hetero-oligomeric complexes of different type I and type II serine/threonine kinase receptors, which can signal via Smad proteins, a class of transcription factors. Smad signaling requires that the growth factor bind to TGF-β receptor type II (TBRII), and the TBRII-growth factor complex interacts with TGF-β receptor type I (TBRI) phosphorylating TBRI. TBRI phosphorylation causes phosphorylation of smad2 which then associates with smad4, and this complex translocates to the nucleus, leading to transcriptional modulation of a series of target genes. In TGF-β signaling TBRII plays a key role. Radiation or oxidant-induced mutations or down-regulation of TBRII contribute to numerous diseases, including severe inflammatory disorders, neurodegenerative disorders, cancer, immune system disorders, failure to repair, kidney diseases, and vascular disease including aneurysms.

Figure 12B:
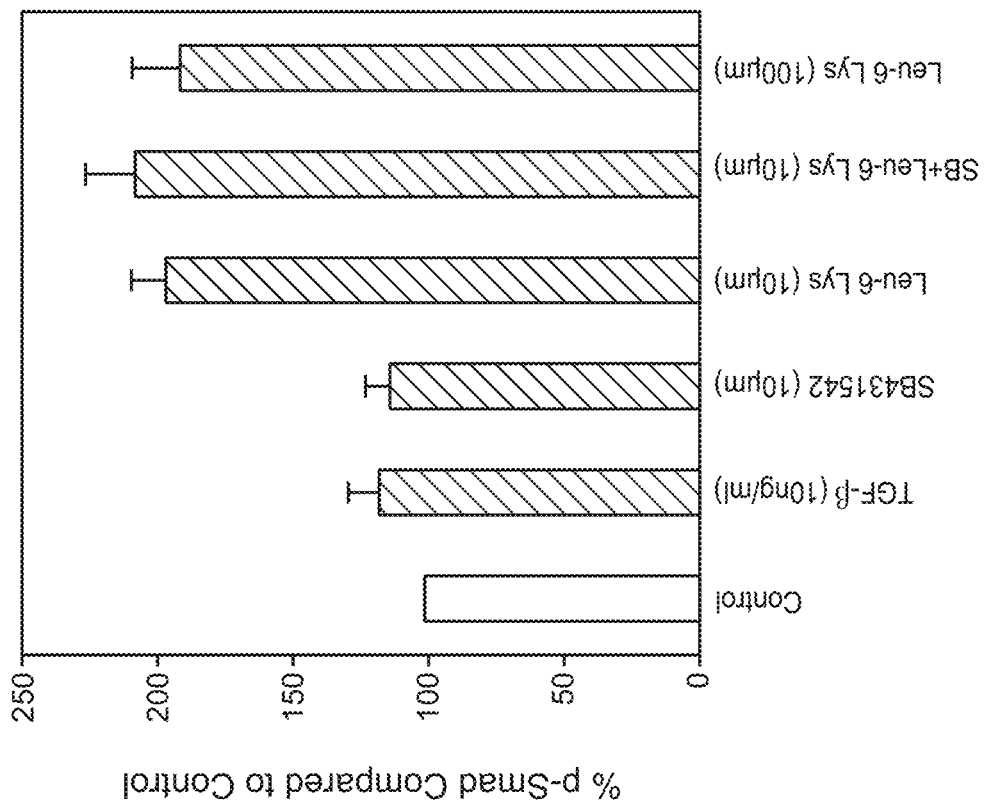
FIG. 12A and FIG. 12B show the effect of peptide LIANAK (SEQ ID NO:060, referred to as "Leu-6 Lys" in the figures) on the phosphorylation of Smad2.
Figure 12A:
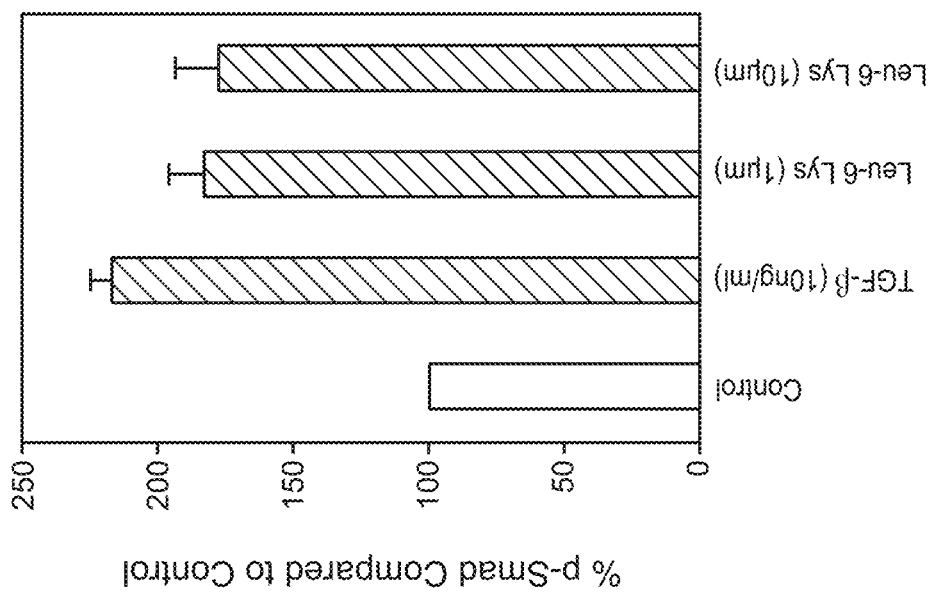

As seen in FIG. 12A and FIG. 12B, a peptide as disclosed herein LIANAK (SEQ ID NO:060, referred to as "Leu-6 Lys" in the figures) can bypass the receptor steps and induce smad signaling. Smad signaling was compared in HepG2 cells which contain an intact signaling system, and MCF-7 cells which lack a functional TBRII. HepG2 cells responded both to TGF-β and LIANAK (SEQ ID NO:060) with identical levels of smad2 phosphorylation. In contrast, only the peptide was able to induce smad2 phosphorylation in TBRII-deficient MCF-7 cells. Furthermore, SB431542 (4-[4-(1,3-benzodioxol-5-yl)-5-(2-pyridinyl)-1H-imidazol-2-yl]benzamide), a potent inhibitor of TBRI, failed to affect peptide-induced smad2 phosphorylation. Thus it can be surmised that the peptides function quite differently from TGF-β. The peptides have utility in the treatment of diseases in which TGF-b signaling is curtailed because of lack of functional TBRII.

Definitions

The following definitions are used herein.

A "subject," "individual," or "patient" is a vertebrate, preferably a mammal, more preferably a human. In other embodiments, the subject, individual, or patient is a food animal, such as a chicken, turkey, duck, goose, cow, lamb, sheep, pig, or goat. In other embodiments, the subject, individual, or patient is a domestic animal, such as a cat, dog, bird, rabbit, or guinea pig. The compounds, compositions, and methods disclosed herein can be used in human medicine and in veterinary medicine.

"Treating" a disease or disorder with the compounds and methods discussed herein is defined as administering one or more of the compounds discussed herein, with or without additional therapeutic agents, in order to reduce or eliminate either the disease or disorder or one or more symptoms of the disease or disorder, or to retard the progression of the disease or disorder or of one or more symptoms of the disease or disorder, or to reduce the severity of the disease or disorder or of one or more symptoms of the disease or disorder. "Suppression" of a disease or disorder with the compounds and methods discussed herein is defined as administering one or more of the compounds discussed herein, with or without additional therapeutic agents, in order to suppress the clinical manifestation of the disease or disorder, or to suppress the manifestation of adverse symptoms of the disease or disorder. The distinction between treatment and suppression is that treatment occurs after adverse symptoms of the disease or disorder are manifest in a subject, while suppression occurs before adverse symptoms of the disease or disorder are manifest in a subject. Suppression may be partial, substantially total, or total.

"Therapeutic use" of the compounds discussed herein is defined as using one or more of the compounds discussed herein to treat or suppress a disease or disorder, as defined above. A "therapeutically effective amount" of a compound is an amount of the compound, which, when administered to a subject, is sufficient to reduce or eliminate either a disease or disorder or one or more symptoms of a disease or disorder, or to retard the progression of a disease or disorder or of one or more symptoms of a disease or disorder, or to reduce the severity of a disease or disorder or of one or more symptoms of a disease or disorder, or to suppress the clinical manifestation of a disease or disorder, or to suppress the manifestation of adverse symptoms of a disease or disorder. A therapeutically effective amount can be given in one or more administrations.

As used herein, the singular forms "a," "an," "or," and "the" include plural referents unless the context clearly dictates otherwise.

Reference to "about" a value or parameter herein includes and describes variations that are directed to that value or parameter itself, as well as other values encompassed by "about." For example, description referring to "about X" includes description of the value "X."

"Administration near the affected area" indicates that a compound which inhibits NF κB activity is administered in sufficient proximity to a site of pathology, such that the compound is able to exert a therapeutic effect on the pathology.

"Inhibitors of NF κB," "inhibition of NF κB," and "NF κB inhibitors" refers to compounds which inhibit the activation or activity of NF κB by any mechanism. The terms "inhibitors of NF κB," "inhibition of NF κB," and "NF κB inhibitors" do not require or necessarily imply direct binding to NF κB; such binding may or may not occur when NF κB activity is inhibited.

"Peptoids" refer to peptide-like polymers comprising poly-N-substituted glycines. In peptoids, amino acid monomers are replaced with monomers where the side chain formerly attached to the alpha carbon of the amino acid is attached to the amino group instead, and the side chain on the alpha carbon has been replaced with hydrogen. Peptoids that can be used in the invention have the same sequence as the peptides indicated here, where the residues in the peptides have been replaced by their peptoid equivalents (for example, alanine in a peptide is replaced with N-methyl glycine). Where a residue indicated in a sequence already bears a non-hydrogen amino substituent, such as proline, that reside remains unchanged when occurring in a peptoid.

"Peptide mimetics" refer to peptides where one or more of the peptide bonds are replaced with an ester bond (—(C=O)—O— instead of —(C=O)—NH—; depsipeptides), where one or more of the peptide bonds are replaced with a thioester bond (—(C=O)—S— instead of —(C=O)—NH—), or where the carbonyl of one or more of the peptide bonds are replaced with a methylene group (—(CH$_2$)—NH— instead of —(C=O)—NH—; reduced amide bonds). Methods for making depsipeptides are described in Stawikowski et al, Methods Mol. Biol. 386: 321-39 (2007) and Albericio et al., Org. Lett. 7(4):597-600 (2005). Methods for making peptides with thioester bonds are described in Raz et al., Org. Lett. 13(7):1606-1609 (2011) and Stuhr-Hansen et al., European Journal of Organic Chemistry 2013(24):5290-5294 (2013). Methods for making peptides with reduced amide bonds are described in Sasaki et al., Peptides 8(1):119-121 and Meyer et al., J. Med. Chem. 38(18):3462-3468 (1995).

While the peptide compounds described herein can occur and can be used as the neutral (non-salt) compounds (including zwitterionic non-salt compounds), the description is intended to embrace all salts of the compounds described herein, as well as methods of using such salts of the compounds. In one embodiment, the salts of the compounds comprise pharmaceutically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N-dibenzylethylenediamine, and triethylamine salts. Salts of acidic compounds with amino acids, such as lysine salts, can also be prepared.

The compounds can be administered in prodrug form. Prodrugs are derivatives of the compounds, which are themselves relatively inactive but which convert into the active compound when introduced into the subject in which they are used by a chemical or biological process in vivo, such as an enzymatic conversion. Suitable prodrug formulations include, but are not limited to, peptide conjugates of the compounds disclosed herein and esters of compounds disclosed herein. Further discussion of suitable prodrugs is provided in H. Bundgaard, *Design of Prodrugs*, New York: Elsevier, 1985; in R. Silverman, *The Organic Chemistry of Drug Design and Drug Action*, Boston: Elsevier, 2004; in R. L. Juliano (ed.), *Biological Approaches to the Controlled Delivery of Drugs* (Annals of the New York Academy of Sciences, v. 507), New York: New York Academy of Sciences, 1987; and in E. B. Roche (ed.), *Design of Biopharmaceutical Properties Through Prodrugs and Analogs* (Symposium sponsored by Medicinal Chemistry Section, APhA Academy of Pharmaceutical Sciences, November 1976 national meeting, Orlando, Florida), Washington: The Academy, 1977.

GENE EXPRESSION DATA: Gene expression data in cells treated with NF κB-inhibitor peptide are presented in support of the unique biological properties of these compounds as potential therapeutic agents. Genes which may be affected by SEQ ID NO:010 are listed in FIG. 7.

PEPTIDES DELAY CELL PROLIFERATION: The cell cycle is subject to numerous controls that ensure correct cell division. The duration of various phases in the cell cycle is under control of checkpoints. Altering the duration of phases under control of checkpoints plays major role in cancer (Bartek and Lukas, Curr. Opin. Cell Biol. 13(6):738-747 (2001); Bartek and Lukas, Science 294(5540):66-7 (2001); Bartek and Lukas, FEBS Lett. 490(3):117-122 (2001)). Apoptosis and proliferation are intimately coupled. Some cell cycle regulators can influence both cell division and programmed cell death. Targeting the cell cycle thus presents unique opportunities for cancer treatment.

NF κB-inhibitor peptides were examined for growth arrest. While TGF R is known to cause G1 phase stasis of cell growth, NF κB-inhibitor peptides markedly prolonged the S— phase. Radiation, free radicals, and cytotoxic therapies are targeted against rapidly dividing diseased cells such as in cancer. By prolonging the S-phase, NF κB-inhibitor peptides offer protection from these cytotoxic therapies to cells that are not undergoing rapid division. Thus NF κB-inhibitor peptides can be useful as a protective measure in cells and tissue prior to receiving cytotoxic treatment.

DESCRIPTION OF COMPOUNDS USEFUL IN THE INVENTION: The inventive compounds are 4-20 residue peptides, peptide-mimetics, or peptoids. The term peptide in this application refers to peptides, peptide-mimetics, and peptoids. The term "standard peptide" is used to refer to polymers of alpha-amino acids and/or imino acids (for example, proline) without peptide bond modifications (that is, peptides excluding peptoids and peptide-mimetics). The compounds useful in the invention have specific tri-peptide core sequences within the body of the peptide as described below. The peptides are designed to emulate a common conformational feature present in protein kinases, both serine threonine kinases and protein tyrosine kinases. These peptides can assume conformations simulating certain interactive domains in signaling protein kinases, and they can modulate the activities of kinases as molecular decoys and by allosteric mechanisms.

CHARACTERISTICS OF PEPTIDES USEFUL IN THE INVENTION: The disclosed peptides mimic important physicochemical characteristics of certain interactive structural features in serine threonine kinases. These features can be simulated by many amino acid sequences. The activity of these peptides is dependent on the presence of one of several contiguous sequences within the body of the peptide. This sequence will be referred to as the "core sequence" hereinafter. The core sequences, each made up of four residues emulate surfaces presented by certain interactive sites present in numerous protein kinases, both protein tyrosine kinases and in serine threonine kinases. While none of these domains may participate in the catalytic activity of the enzymes, their presence both in the enzymes and in the substrate protein kinases is essential for intermolecular recognition and interaction. The peptide design is based on the argument that interactive sites on proteins need to be near the surface, that they may exist in more than one isoenergic conformation one of which presents an optimal surface to couple with a complementary receiving site on the interacting partner, that the interaction is fully consummated by induced fit, that the interactions typically involve weak bonds, and finally, the interactive domains do not need to be large. We have performed in silico interaction studies between several of the disclosed peptides and a number of protein kinases and our studies confirm stable peptide-kinase interactions. Specifically, these studies predict interaction with the similar receiving site on different kinases. Thus, we postulate that the peptides alter kinase activities by mimicking specific molecular domains on one partner (say Protein A) in its interaction with its specific receiving site on Protein B. Thus the peptides may be referred to as molecular decoys. The core sequences essential for the activity of the peptides are described below. While many of the amino acid residues listed here do not occur naturally in animal proteins, they are included here for their ability to contribute to peptide surfaces mimicking domains found in numerous enzymes and proteins associated with the activation of NF κB.

The peptides as disclosed herein contain various core sequences found to confer NF κB inhibitory activity. The peptides can range in length from four to twenty amino acids, four to fifteen amino acids, four to twelve amino acids, four to ten amino acids, four to eight amino acids, six to twenty amino acids, six to fifteen amino acids, six to twelve amino acids, six to ten amino acids, or six to eight amino acids, as long as the peptide comprises the appropriate core sequence. For peptides indicated as comprising a specific sequence, the lower limit of the peptide length is the specific sequence indicated, while the upper limit of the peptide length can be twenty amino acids, fifteen amino acids, twelve amino acids, ten amino acids, or eight amino acids, with the proviso that the upper limit of peptide length is greater than or equal to the lower limit of peptide length (that is, the upper limit of the peptide length cannot be shorter than the sequence specified for the peptide).

CORE SEQUENCE (1): Xxx-Ala-Pro-Glu, where Xxx is Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, or β-tert-butyl-Ala CORE SEQUENCE (2): Xxx-Ala-Pro-(D)Glu, where Xxx is Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, or β-tert-butyl-Ala CORE SEQUENCE (3): Xxx-Ala-Glu-Ala, where Xxx is Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, or β-tert-butyl-Ala CORE SEQUENCE (4): Xxx-Ala-[D]Glu-Ala where Xxx is Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, or β-tert-butyl-Ala CORE SEQUENCE (5): Xxx-Ala-Asn-Ala, where Xxx is Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, or β-tert-butyl-Ala CORE SEQUENCE (6): Xxx-Ala-(D)Asn-Ala, where Xxx is Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, or β-tert-butyl-Ala In some embodiments of peptides of the sequences described here, Pro is replaced by Hyp or by pyroglutamic acid.

In the sequences described above and any other sequence disclosed herein, in some embodiments of the peptides Ala may be replaced with Ser, N-methyl-Ser, N-methyl-Ala, Nva, N-methyl-Nva, Aab, N-methyl-Aab, Aib, N-methyl-Aib, Allyl-Gly, Sarcosine, propargyl-Gly, Indanyl-Gly, Cyclohexyl-Gly, phenyl-Gly, dehydroalanine, or homovaline.

In the sequences described above and any other sequence disclosed herein, Met may be replaced with the isostere norleucine (Nor).

In some embodiments, the residues on the C-terminus of the core sequences described above and any other sequence disclosed herein, may be un-natural amino acids such as 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, or β-tert-butyl-Ala.

In some embodiments the residue on the C-terminus of the core sequences described above and any other sequence disclosed herein, may be un-natural amino acids such as 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, or β-tert-butyl-Ala.

In other embodiments the residues on both the N- and C-terminus of the core sequences described above, and any other sequence disclosed herein, may be un-natural amino acids such as 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, or β-tert-butyl-Ala.

In some embodiments, the residues on the N- and C-termini of the core peptide sequences described above, and any other sequence disclosed herein, may be residues or compounds designed to protect the peptide from degradation by proteases or peptidases.

In another embodiment the peptide active core may be extended with additional amino acids on its N-terminus, or on its C-terminus, or on both termini such that the total number of amino acids may not exceed twenty.

In other embodiments, the active core sequence as described above, and any other sequence disclosed herein, or its extended forms as described herein may be coupled to a larger molecule such as polyethylene glycol, or a polysaccharide, to enhance its dwell time in tissues and in organs including the alimentary canal.

Peptides in various embodiments as described above may be modified to produce pro-drugs that would be transformed to the active form in physiologic milieu.

Peptides in various embodiments as described above may be coupled to a lipid molecule, to enhance penetration in tissues and dwell time in tissues and organs including the alimentary canal.

Peptides in various embodiments as described above may be modified to increase their stability in the presence of proteases present in tissue fluids, in serum, saliva, in the alimentary canal, and in various body fluids in the tissues under treatment. Such protective modifications include, but are not restricted to:

Addition of a D-amino acid on the N-terminus of the peptide;
Acetylation of the N-terminal amino group;
Modification of the N-terminal amino group with 1-amino-cyclohexane-carboxylic acid;
Modification of the N-terminal amino group with β-acetyl-2,3-diamino propionic acid;
Amidation of the C-terminal carboxyl group with —NH$_2$; and
Esterification of the C-terminal carboxyl group with —OCH$_3$ or —OCH$_2$CH$_3$.

Some of the peptides described here were previously disclosed in U.S. Pat. Nos. 5,661,127; 5,780,436; and 6,638,912, and U.S. Patent Publication No. 2006/0293228, that described TGF R-like activity of the peptides. In the present context, these peptides are demonstrated to act unexpectedly, in a manner opposite to that of TGF 3. In the present application, the peptides inhibit NF κB activation. In contrast, NF κB is a well-known antagonist of TGF R. Furthermore, the biological activity of TGF R requires the concerted action of two sets of receptors forming a quaternary complex with two TGF R molecules, each of which is a dimer of two 12.5 kD subunits. The inhibition of NF κB by these peptides is an unusual and unexpected property of these small peptides. While TGF R is known to cause G1 phase stasis of cell growth, NF κB-inhibitor peptides markedly prolonged the S— phase. Because of these highly unusual properties of the NF κB inhibitor peptides in comparison to growth factor like activity, this application incorporates peptides described in U.S. Pat. Nos. 5,661,127; 5,780,436; and 6,638,912, and U.S. Patent Publication No. 2006/0293228, by reference, and the list of peptides therein in their entirety.

In some embodiments, the total length of the peptide including core sequences may be seven, eight, nine, ten, eleven, twelve, thirteen, fourteen, fifteen, sixteen, seventeen, eighteen, nineteen or twenty residues, such that in a peptide nX(CORE)mX, where n is the number of residues X on the N-terminal of the core sequence, and m is the number of residues X on the C-terminal of the core sequence, the sum of n+m+the number of residues in the CORE sequence is five, six, seven, eight, nine, ten, eleven, twelve, thirteen, fourteen, fifteen, sixteen, seventeen, eighteen, nineteen or twenty.

In other embodiments, the numbers n and m may range from zero to sixteen, such that the core sequence may be part of a longer sequence in which the residues X on the N-terminal side and on the C-terminal side of the CORE sequence may not be the same, thus, the following sequences are contemplated:

(CORE)-mX where the residues on the C-terminal side of the core sequence may be none (0) to sixteen (16), m is the number of residues X on the C-terminus of the peptide;
nX-(CORE) where the residues X are zero to sixteen, n referring to the number of residues on the N-terminal side of the core sequence; and
nX-(CORE)-mX where the numbers n and m are independently variable.

As discussed above, the amino acids making up the residues X are also independently variable.

In any of the embodiments of the specific peptide sequences disclosed herein, homologous sequences having at least about 70%, at least about 75%, at least about 80%, at least about 85%, at least about 90%, or at least about 95% sequence homology can be used, provided that the core sequence is maintained.

In any of the embodiments of the specific peptide sequences disclosed herein, substitutions can be made in the non-core regions of the sequence by replacing one, two, or three amino acids with a homologous amino acid. Thus, negatively charged amino acids can be substituted for other negatively charged amino acids (Asp, Glu); positively charged amino acids can be substituted for other positively charged amino acids (Lys, Arg, His); hydrophobic amino acids can be substituted for other hydrophobic amino acids (Ala, Val, Ile, Leu, Met); hydrophilic amino acids can be substituted for other hydrophilic amino acids (Ser, Thr) (Asn, Gln); aromatic amino acids can be substituted for other aromatic amino acids (Phe, Tyr, Trp, His); and less bulky amino acids can be substituted for other less bulky amino acids (Ala, Gly). The groups of amino acids in parentheses indicate amino acids considered homologous for purposes of substitution.

SYNTHESIS OF PEPTIDES: The synthesis of peptides is commonly practiced and a person familiar with the art can easily reproduce the compounds disclosed here. Most commonly, peptides are synthesized in commercially available instruments, each of which is provided with directions and methods. Peptides may also be obtained from a large number of companies that specialize in the manufacture of peptides. The peptide may be synthesized by any suitable method for producing peptides of a given sequence. Preferably, peptides of the present invention can be synthesized by various suitable methods that are well known in the art, preferably by solid phase synthesis, manual or automated, as first developed by Merrifield and described by Stewart et al. in *Solid Phase Peptide Synthesis* (1984). Chemical synthesis joins the amino acids in the predetermined sequence starting at the C-terminus. Basic solid phase methods require coupling the C-terminal protected α-amino acid to a suitable insoluble resin support. Amino acids for synthesis require protection on the α-amino group to ensure proper peptide bond formation with the preceding residue (or resin support) and to ensure that only one amino acid is coupled to the growing peptide chain at each step. Amino acids with reactive side chains must also have side-chain protection that remains on the side chain during the synthesis, but which can be removed at the end of synthesis. Following completion of the condensation reaction at the carboxyl end, the α-amino protecting group is removed to allow the addition of the next residue. Several classes of α-protecting groups have been described, see Stewart et al. in *Solid Phase Peptide Synthesis* (1984), with the acid labile, urethanebased tertiary-butyloxycarbonyl (Boc) being the historically preferred. Other protecting groups, and the related chemical strategies, may be used, including the base labile 9-fluorenylmethyloxycarbonyl (FMOC). Also, the reactive amino acid sidechain functional groups require blocking until the synthesis is completed. The complex array of functional blocking groups, along with strategies and limitations to their use, have been reviewed by Bodansky in *Peptide Synthesis* (1976) and, Stewart et al. in *Solid Phase Peptide Synthesis* (1984). Fmoc synthesis of peptides is described in detail in W. C. Chan and Peter D. White (Editors), *Fmoc Solid Phase Peptide Synthesis: A Practical Approach* (*The Practical Approach Series*) 1st Edition, Oxford: Oxford University Press, 2000.

Solid phase synthesis using Boc chemistry is initiated by covalently attaching the C-terminal α-amino acid residue, with a protecting group on the α-amino group, to the solid-phase resin. The α-amino protecting group is removed by trifluoroacetic acid (25% or greater) in dichloromethane in the case of acid labile tertiary-butyloxycarbonyl (Boc) groups. A neutralizing step with triethylamine (10%) in dichloromethane recovers the free amine (versus the salt). Then the penultimate C-terminal amino acid is coupled to the C-terminal amino acid by using the Boc-protected version of the penultimate C-terminal α-amino acid. Coupling requires activating agents, such as dicyclohexylcarbodiimide (DCC) with or without 1-hydroxybenzo-triazole (HOBT), diisopropylcarbodiimide (DIIPC), or ethyldimethylaminopropylcarbodiimide (EDC). After coupling the penultimate C-terminal residue, the α-amino protecting group is again removed by trifluoroacetic acid (25% or greater) in dichloromethane in the case of acid labile tertiary-butyloxycarbonyl (Boc) groups. A neutralizing step with triethylamine (10%) in dichloromethane again recovers the free amine (versus the salt). The cycle of deprotection, neutralization and coupling, with intermediate wash steps, is repeated in order to extend the protected peptide chain. Each protected amino acid is introduced in excess (three to five fold) with equimolar amounts of coupling reagent in suitable solvent. Finally, after the completely blocked peptide is assembled on the resin support, reagents are applied to cleave the peptide form the resin and to remove the side chain blocking (protecting) groups. Anhydrous hydrogen fluoride (HF) cleaves the acid labile tertiary-butyloxycarbonyl (Boc) chemistry groups, cleaves side-chain protecting groups, and cleaves the peptide from the resin. Several nucleophilic scavengers, such as dimethylsulfide and anisole, are included to avoid side reactions especially on side chain functional groups.

Slight amino acid modifications to a peptide NF κB-inhibitor sequence will not affect the peptide's ability to form suitable NF κB-inhibitors. These modifications include techniques to confer resistance to enzymatic degradation such as adding blocking groups to both the N- and C-terminal residues. Another method for preventing degradation and premature clearance by the renal system is the use of unnatural amino acid substitutes in the peptide sequence. For example, N-methyl-alanine is often substituted for alanine and α-amino isobutyric acid and α-amino butyric acid are substitutes for bulky hydrophobic amino acids.

Recombinant techniques, as known in the art, may also be used to produce peptides suitable for the methods of the invention. Naturally-occurring proteins may be cleaved to produce a desired NF κB-inhibitor. Methods of designing and screening small molecules may also be used. Methods to generate and screen peptido-mimetics may also be useful in producing NF κB-inhibitors. Substances that are a mixture of peptide and peptido-mimetics may also be used.

While the foregoing invention has been described in some detail for purposes of clarity and understanding, it will be appreciated by one skilled in the art, from a reading of the disclosure, that various changes in form and detail can be made without departing from the true scope of the invention in the appended claims.

AMINO ACID RESIDUES: Amino acids and their three and one letter codes are used in their customary format; non-proteinogenic amino acids are listed in standard abbreviations.

EXAMPLES OF PEPTIDES USEFUL IN THE INVENTION: This list (FIGS. 8A and 8B) is presented only as examples of peptides incorporating the bioactive core sequences as described herein and is not meant to be comprehensive.

FORMULATION: According to some embodiments, the present invention provides a pharmaceutical composition comprising as an active ingredient an agent capable of inhibiting NF κB activation, and a pharmaceutically acceptable carrier, excipient or diluent. As used herein, a "pharmaceutical composition" refers to a preparation of one or more of the active ingredients described herein, with other components such as physiologically suitable carriers and excipients. The purpose of a pharmaceutical composition is to facilitate administration of a compound to a subject.

Hereinafter, the phrases "therapeutically acceptable carrier" and "pharmaceutically acceptable carrier", which may be used interchangeably, refer to a carrier or a diluent that does not cause significant irritation to an organism and does not abrogate the biological activity and properties of the administered compound. Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

In another embodiment of the present invention, a therapeutic composition further comprises a pharmaceutically acceptable carrier. As used herein, a "carrier" refers to any substance suitable as a vehicle for delivering of the agents or molecule of the present invention to a suitable in vivo or in vitro site. As such, carriers can act as a pharmaceutically acceptable excipient of a therapeutic composition of the present invention. Carriers of the present invention include: (1) excipients or formularies that transport, but do not specifically target a molecule to a cell (referred to herein as non-targeting carriers); and (2) excipients or formularies that deliver a molecule to a specific site in a subject or a specific cell (i.e., targeting carriers). Examples of non-targeting carriers include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Therapeutic compositions of the present invention can be sterilized by conventional methods.

Targeting carriers are herein referred to as "delivery vehicles". Delivery vehicles of the present invention are capable of delivering a therapeutic composition of the present invention to a target site in a subject. A "target site" refers to a site in a subject to which one desires to deliver a therapeutic composition. Examples of delivery vehicles include, but are not limited to, artificial and natural lipid-containing delivery vehicles. Natural lipid-containing delivery vehicles include cells and cellular membranes. Artificial lipid-containing delivery vehicles include liposomes and micelles. A delivery vehicle of the present invention can be modified to target to a particular site in a subject. Suitable modifications include manipulating the chemical formula of the lipid portion of the delivery vehicle and/or introducing into the vehicle a compound capable of specifically targeting a delivery vehicle to a preferred site, for example, a preferred cell type. Specifically targeting refers to causing a delivery vehicle to bind to a particular cell type by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. For example, an antibody specific for an antigen found on the surface of a target cell can be introduced to the outer surface of a liposome delivery vehicle so as to target the delivery vehicle to the target cell. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics. This list is not comprehensive and additional formulations may be developed to deliver the peptide inhibitor of NF κB.

One or more of the peptides may be formulated as a pharmaceutical composition. Such composition may be administered topically, orally, intravenously, by inhalation, by infusion, by injection, intraperitoneally, intramuscularly, subcutaneously, intra-aurally, by intra-articular administration, by intra-mammary administration, rectally, by topical administration or by absorption through epithelial and/or muco-cutaneous linings. This list is not comprehensive and additional formulations may be developed to deliver the peptide inhibitor of NF κB.

The peptides may be formulated such as: a solid, powder, lyophilized powder, aqueous solution, aqueous suspension, solution in an excipient liquid, emulsion, paste, spray, cream, lotion, controlled release formulation, tablet, pill, gel, liposome, on a patch, in an implant, on a tape, capsule, lozenge, dragee, gel, syrup, slurry and/or a suspension, formulated with a solid excipient, carbohydrate, protein filler, sugar such as lactose, sucrose, mannitol, sorbitol, starch, cellulose, methyl cellulose, hydroxypropylmethylcellulose sodium carboxy-methylcellulose, cross-linked polyvinyl pyrrolidone, gum, tragacanth, gelatin, collagen, disintegrating or solubilizing agent, agar, alginic acid alginic salt, sodium alginate. This list is not comprehensive and additional formulations may be developed to deliver the peptide inhibitor of NF κB.

The peptides in various embodiments as described above may be administered in delivery devices and systems such as slow release compositions, mechanical and electro-mechanical devices, nano-particles, microspheres, liposomes, adhesive films and pastes, mucoadhesives, oral mucoadhesives, vaginal mucoadhesives, Orajel, Orabase, pastes, solution, solid excipients, intravenously, intra-dermally, intramuscularly, intra-peritoneally, by ultrasound and iontophoresis, by electroporation, hydrophilic emulsion foam, lipophilic emulsion foam, nanoemulsion foam, aqueous foam, hydroethanolic foam, potent-solvent foam, suspension foam, ointment foam, hydrophilic ointment foam, oil foam, saccharide foams, as part of dendrimers. This list is not comprehensive and additional formulations may be developed to deliver the peptide inhibitor of NF κB.

The peptides in various embodiments as described above may be administered in combination with permeability enhancers such as: 8-(N-2-hydroxy-5-chloro-benzoyl)-amino-caprylic acid (5-CNAC), 23-lauryl ether, Aprotinin, Azone, Benzalkonium chloride, Cetylpyridinium chloride, Cetyltrimethylammonium bromide, Cyclodextrin, Cyclopentadecalactone, Dextran sulfate, Dodecyl-2-N,N-dimethylamino propionate (DDAIP), Lauric acid, Lauric acid/Propylene glycol, Lysophosphatidylcholine, Methoxysalicylate, Methyloleate, Oleic acid, Phosphatidylcholine, Polyoxyethylene, Polysorbate 80, Sodium EDTA, Sodium glycocholate, Sodium glycodeoxycholate, Sodium lauryl sulfate, and Sodium N-[8-(2-hydroxylbenzoyl)amino] caprylate (SNAC), Sodium salicylate, Sodium taurocholate, Sodium taurodeoxycholate, Sulfoxides, and various alkyl glycosides. This list is not comprehensive and additional formulations may be developed to deliver the peptide inhibitor of NF κB.

The peptides in various embodiments as described above may be administered in combination with and as adjuncts to therapeutic and palliative regimens and may be delivered with one or more of additives such as, analgesics, antibiotics, antivirals, growth factors, palliatives, anti-oxidants, vitamins, MMP-inhibitors. This list is not comprehensive and additional formulations may be developed to deliver the peptide inhibitor of NF κB.

In addition to the formulations described above, the compounds (that is, the disclosed peptides as described herein) can be formulated as pharmaceutical compositions by formulation with additives such as pharmaceutically acceptable excipients, pharmaceutically acceptable carriers, and pharmaceutically acceptable vehicles. Suitable pharmaceutically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference.

A pharmaceutical composition can comprise a unit dose formulation, where the unit dose is a dose sufficient to have a therapeutic or suppressive effect on a disease or disorder. The unit dose may be sufficient as a single dose to have a therapeutic or suppressive effect on a disease or disorder. Alternatively, the unit dose may be a dose administered periodically in a course of treatment or suppression of a disease or disorder.

Pharmaceutical compositions containing the compounds of the present invention (the disclosed peptides as described herein) and compositions containing the compounds of the present invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Time-release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the invention may be administered enterally, orally, parenterally, sublingually, by inhalation (e.g. as mists or sprays), rectally, or topically in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g. via nasal mucosa), subdural, rectal, gastrointestinal, and the like, and directly to a specific or affected organ or tissue. Microinjection can also be utilized, as well as needle-free injection, such as jet injection. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The compounds are mixed with pharmaceutically acceptable carriers, adjuvants, and vehicles appropriate for the desired route of administration. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

In some embodiments of the invention, especially those embodiments where a formulation is used for injection or other parenteral administration including the routes listed herein, but also including embodiments used for oral, gastric, gastrointestinal, or enteric administration, the formulations and preparations used in the methods of the invention are sterile. Sterile pharmaceutical formulations are compounded or manufactured according to pharmaceutical-grade sterilization standards (United States Pharmacopeia Chapters 797, 1072, and 1211; California Business & Professions Code 4127.7; 16 California Code of Regulations 1751, 21 Code of Federal Regulations 211) known to those of skill in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., Methods in Cell Biology, Volume XIV, Academic Press, New York, N.W., p. 33 et seq (1976).

The invention also provides articles of manufacture and kits containing materials useful for treating or suppressing diseases or disorders. The invention also provides kits comprising any one or more of the compounds of formula I. In some embodiments, the kit of the invention comprises the container described above.

In other aspects, the kits may be used for any of the methods described herein for treating a disease or disorder.

The amount of active ingredient that may be combined with the carrier materials to produce a single dosage form will vary depending upon the host to which the active ingredient is administered and the particular mode of administration. It will be understood, however, that the specific dose level for any particular patient will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy. The pharmaceutical unit dosage chosen is usually fabricated and administered to provide a defined final concentration of drug in the blood, tissues, organs, or other targeted region of the body. The therapeutically effective amount or effective amount for a given situation can be readily determined by routine experimentation and is within the skill and judgment of the ordinary clinician.

Examples of dosages which can be used are a therapeutically effective amount or effective amount within the dosage range of about 0.1 mg/kg to about 300 mg/kg body weight, or within about 1.0 mg/kg to about 100 mg/kg body weight, or within about 1.0 mg/kg to about 50 mg/kg body weight, or within about 1.0 mg/kg to about 30 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Compounds of the present invention may be administered in a single daily dose, or the total daily dosage may be administered in divided dosage of two, three or four times daily.

While the compounds of the invention can be administered as the sole active pharmaceutical agent, or as the sole active pharmaceutical agent present in a therapeutically effective amount, they can also be used in combination with one or more other agents used in the treatment or suppression of diseases or disorders. When additional active agents are used in combination with the compounds of the present invention, the additional active agents may generally be employed in therapeutic amounts as indicated in the Physicians' Desk Reference (PDR) 53rd Edition (1999), or such therapeutically useful amounts as would be known to one of ordinary skill in the art.

The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

The disclosed peptides and related compounds can inhibit the activation of NF κB in cells and tissues of human subjects and animals who are in need of treatment for diseases and disorders caused by perturbations in NF κB activation and its subsequent translocation to the cell.

The disclosed peptides and related compounds can be used to prevent, treat, ameliorate, remedy, cure, heal diseases caused by perturbations in NF κB activation.

The disclosed peptides and related compounds can pre-treat, prevent, treat, ameliorate, remedy, cure, diminish, and heal diseases caused by perturbations in NF κB activation, such diseases including inflammation, infection, and injury, burns, chronic wounds, ulcers, stasis ulcers, venous ulcers, and diabetic ulcers.

By prolonging the S-phase, NF κB-inhibitor peptides can protect tissues from cytotoxic therapies targeted at cancer cells. Thus NF κB-inhibitor peptides can be used as a protective measure in cells and tissue about to receive cytotoxic treatment.

NF κB-inhibitor peptides are not cytotoxic and do not interfere with normal cellular physiology. Low level of NF κB activation is key to normal tissue homeostasis and healthy immune function, whereas increased activation of NF κB is a hallmark of numerous diseases. Thus NF κB inhibitor peptides can be expected to have differential effects on normal and healthy tissues and diseased tissues, bringing the latter to a normal state by inhibiting NF κB activation.

Activation of NF κB allows the transcription factor to translocate in the nucleus and its interaction with specific genomic sites results in the expression of genes that contribute to disease. These genes include chemokines, interleukins, TNF α and the receptors for these deleterious proteins among numerous other undesirable proteins. Thus inhibition of the activation of NF κB by the disclosed peptides also prevents further disorders that would be caused by the chemokines, cytokines, TNF α, and their related receptors proteins. Since these molecules also contribute to the activation of NF κB, it can be seen how the disclosed peptide inhibitors of NF κB activation interrupt a self-sustaining feedback loop that perpetuates and exacerbates disease process.

Some of the diseases in which the therapeutic/prophylactic composition of the invention is indicated are those involving the cytokine TNF α. The cytokine TNF α plays a key role in inflammatory diseases. TNF α antagonists, primarily biologics that neutralize the cytokine are widely used for treatment of inflammatory diseases. While the use of such agents is expanding to cover a wider range of disorders, adverse side effects such as increased susceptibility to infection resulting from elimination of systemic TNF α raise serious concerns. Biologicals used as TNF α blockers have been associated increasingly with risks of serious infectious diseases including tuberculosis and musculoskeletal and dermal infections, autoimmune diseases such as lupus, psoriasis, ulcers, vasculitis and chronic venous insufficiency, demyelinating disease, urticaria, rash, congestive heart failure, and many forms of cancer. The primary mechanism of the pro-inflammatory effects of TNF α is the activation of NF κB, which then feeds the inflammatory process by increasing the expression of numerous proteins that contribute to pathophysiology, including feedback mechanisms that upregulate TNF α and other undesirable proteins. The disclosed peptides have been tested in experiments as antagonists of TNF α and interleukins, inhibiting the activation of NF κB by these cytokines. Thus, the disclosed NF κB-inhibitor peptides are a desirable alternative to TNF α scavengers.

DISEASES: Some of the diseases in which the therapeutic/prophylactic composition of the invention is indicated are specific NF κB associated diseases, that is to say diseases caused by the unwanted activation of genes under control of the transcriptional regulatory factor NF κB. Accordingly, the diseases disclosed herein can be treated with the disclosed peptides, including one or more peptides selected from the group consisting of CORE SEQUENCE (1), CORE SEQUENCE (1-N), CORE SEQUENCE (1-U), GROUP (1-S), GROUP (1-T), GROUP (1-V), GROUP (1-W), CORE SEQUENCE (2), CORE SEQUENCE (2-N), CORE SEQUENCE (2-U), GROUP (2-S), GROUP (2-T), GROUP (2-V), CORE SEQUENCE (3), CORE SEQUENCE (3-N), CORE SEQUENCE (3-U), GROUP (3-S), GROUP (3-T), GROUP (3-V), GROUP (3-W), CORE SEQUENCE (4), CORE SEQUENCE (4-N), CORE SEQUENCE (4-U), GROUP (4-S), GROUP (4-T), GROUP (4-V), CORE SEQUENCE (5), CORE SEQUENCE (5-N), CORE SEQUENCE (5-U), GROUP (5-S), GROUP (5-T), GROUP (5-V), GROUP (5-W), CORE SEQUENCE (6), CORE SEQUENCE (6-N), CORE SEQUENCE (6-U), GROUP (6-S), GROUP (6-T), GROUP (6-V), CORE SEQUENCE (7), CORE SEQUENCE (7-N), CORE SEQUENCE (7-U), GROUP (7-S), GROUP (7-T), GROUP (7-V), GROUP (7-W), CORE SEQUENCE (8), CORE SEQUENCE (8-N), CORE SEQUENCE (8-U), GROUP (8-S), GROUP (8-T), GROUP (8-V), SEQ ID NOS:001-069, (SEQ ID NOS:001-008, 010, 011, and 013-040), and (SEQ ID NOS:001-007, 010, 011, 013-029, and 031-040). Among these diseases are ischemic diseases, inflammatory diseases, autoimmune diseases, cancer metastasis and invasion, and cachexia. The ischemic diseases include ischemic diseases of organs, e.g. ischemic heart diseases such as myocardial infarction, acute heart failure, chronic heart failure, etc., ischemic brain diseases such as cerebral infarction, and ischemic lung diseases such as pulmonary infarction.

MUCOCUTANEOUS DISEASES: NF κB-inhibitor peptides can be used to treat and to ameliorate, diminish, improve, and/or inhibit unwanted side effects and symptoms, including those which are erythematous, ulcerative, inflammatory, necrotic or erosive dysplasias of muco-cutaneous surfaces, such as those in the oral cavity, the nasal cavity, the gastrointestinal and respiratory tracts, the vagina, and the bladder, mucositis, oral mucositis, denture stomatitis, oral lichen planus, aphthous ulcers, pemphigus, bullous pemphigoid, oral lichen planus, and oral mucous membrane contact dermatitis; herpetiform ulcers, canker sores, digestive mucositis, esophageal mucositis, intestinal mucositis, inflammatory bowel disease, ulcerative colitis and Crohn's disease, aphthous ulcers, pemphigus, bullous pemphigoid, oral lichen planus, and oral mucous membrane contact dermatitis; herpetiform ulcers, canker sores, diseases of the nasal mucous membrane include sinusitis and rhinitis; examples for the bladder include interstitial cystitis and radiation cystitis. Certain diseases such as Behcet syndrome, can affect the mucocutaneous membranes of several regions of the body. Many other ulcerative mucocutaneous diseases are known. There are also painful ulcerative disorders of mucosal surfaces which result as an adverse side-effect in certain therapies, such as chemotherapy and radiation therapy. Examples of such side-effects include mucositis, esophagitis, and radiation proctitis. Mucosal injury may also result from endoscopic procedures.

Figure 11:
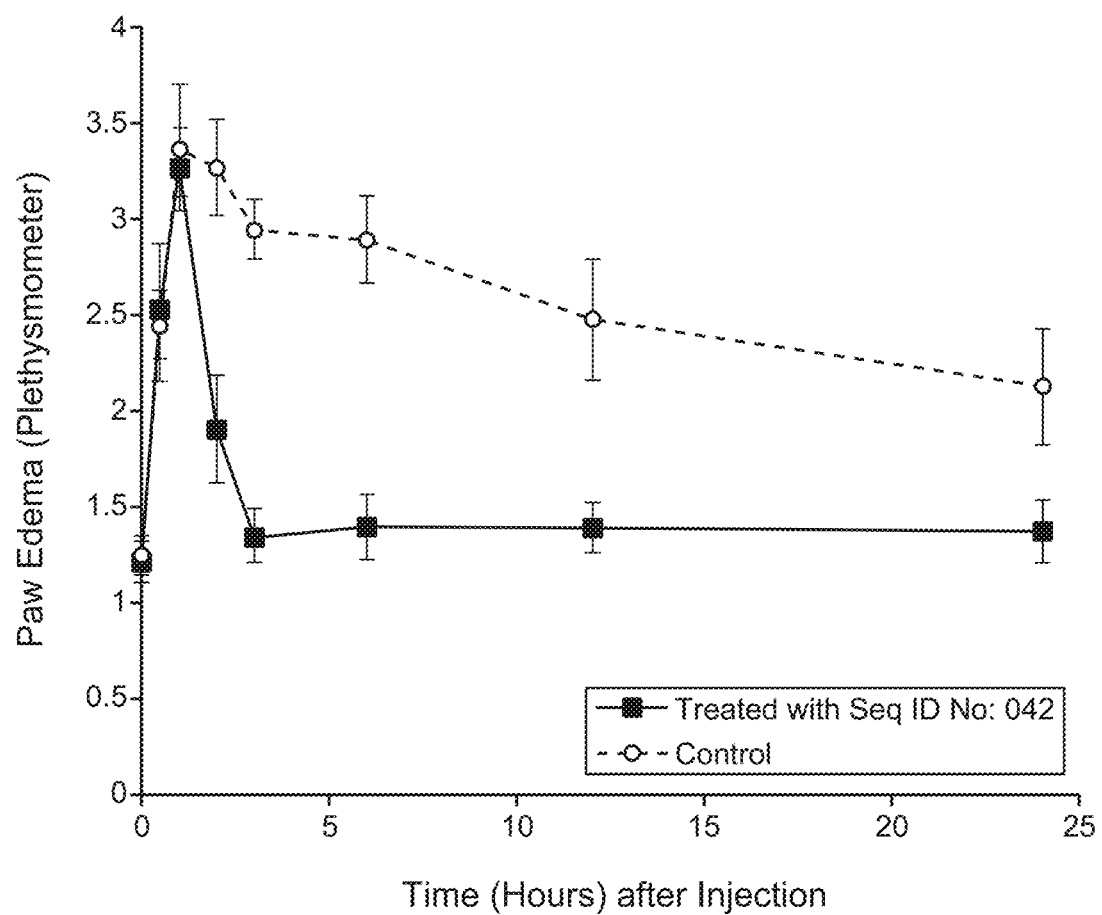
FIG. 11 shows amelioration of inflammation by the peptide ANVAENA (SEQ ID NO: 042). The lighter (upper) curve shows control, while the darker (lower) curve shows treatment with peptide.

INFLAMMATORY DISEASES AND FIBROTIC DISEASES: NF-κB is a prototypical proinflammatory signaling pathway, based on the activation of NF-κB by proinflammatory cytokines such as interleukin 1 (IL-1) and tumor necrosis factor a (TNF-α), and the subsequent role of NF-κB in the expression of other proinflammatory genes including cytokines, chemokines, and adhesion molecules. Inhibition of NF-κB can be expected to result in amelioration of inflammation. This was confirmed experimentally using peptide SEQ ID NO:042 in a standard model of carrageenan-induced inflammation in rat paw. This method measures acute inflammation induced by injection of carrageenan (Sakat et al., Inflammation 37(1):1-9 (2014)) and is used extensively to study antiinflammatory properties of drugs. Carrageenan is known to activate NF-κB (Bhattacharyya et al., Mediators of Inflammation, Vol. 2013, Article ID 397642; Bhattacharyya et al., American Journal of Physiology 301(3):G475-G486 (2011); Ellis et al., Ann. Rheum. Dis. 59:303-307 (2000); Pierce et al., J. Biol. Chem. 272: 21096-21103 (1997)). Example 6 and FIG. 11 show the high efficacy of peptide SEQ ID NO:042 in alleviating edema and inflammation. Nearly identical results (not shown here) were seen with peptide SEQ ID NO:001 (YMAPEV). Treatment of inflammation requires the subsidence of TNF-α and NF-κB pathways, which are part of the action of the disclosed peptides. These results support the use of the disclosed peptides in the treatment of acute and chronic inflammation, such as that seen in cases of injury, burns, infection, radiation damage to tissues, insect bites, allergic reactions; in chronic diseases in which inflammation is known to play a significant role including but not limited to Acne, Ankylosing spondylitis, Barrett's esophagus, Chronic fatigue syndrome (CFS/CFIDS/ME), Chronic Lyme disease (borreliosis), Crohn's disease, Diabetes, Depression, Dermatitis, Fascitis, Fibromyalgia (FM), Gastroesophageal reflux disease (GERD), Gingivitis, Guillain-Barré syndrome, Hashimoto's thyroiditis, Hypertension, Hyperthyroidism, Hypothyroidism, Irritable Bowel Syndrome (IBS), Insulin Resistance, Interstitial cystitis (IC), Kidney stones, Löfgren's syndrome, Lupus erythematosus, Multiple Chemical Sensitivity (MCS), Migraine headache, Morgellon's, Multiple sclerosis, Obesity, Osteoarthritis, Periodontitis, Polymyalgia rheumatica, Prostatitis, Psoriasis, Psoriatic arthritis, Raynaud's syndrome/phenomenon, Reactive arthritis (Reiter syndrome), Restless leg syndrome, Reflex Sympathetic Dystrophy (RSD), Rheumatoid arthritis, Sarcoidosis, Scleroderma, Septic Shock, Sinusitis, Seasonal affective disorder (SAD), Sjögren's syndrome, Stomatitis, Tendonitis, Ulcerative colitis, Urticaria, Uveitis, and Vertigo.

Chronic inflammation is seen in autoimmune diseases and thus the disclosed peptides are indicated as a treatment. Such diseases include rheumatoid arthritis, multiple sclerosis, lupus, and amyotrophic lateral sclerosis (ALS).

Chronic inflammation is also seen in auto-inflammatory diseases. Auto-inflammatory diseases are due to inflammation caused by the innate immune system (for unknown reasons), and include diseases such as familial mediterranean fever (FMF), neonatal onset multisystem inflammatory disease (NOMID), tumor necrosis factor (TNF) receptor-associated periodic syndrome (TRAPS), deficiency of the interleukin-1 receptor antagonist (DIRA), and Behçet's Disease.

Chronic inflammation is also seen in disorders of the gastrointestinal tract, such as Crohn's disease and colitis, and thus the disclosed peptides are indicated as a treatment. For disorders of the large intestine, compositions comprising the peptides can be administered as enemas or colonics.

Chronic inflammation can be caused by infectious agents, such as bacteria, viruses, fungi, or parasites such as worms or protozoans, and can result in, among other disorders, endocarditis. Infection can result in chronic inflammatory response due to secretion of inflammatory mediators, including chemokines [interleukin (IL)-8, macrophage chemotactic protein (MCP)-1, growth-regulated oncogene (GRO)-α] and cytokines [IL-10, tumor necrosis factor (TNF)-α, IL-6, IL-12, interferon (IFN)-γ], which can enter circulation and have a systemic effect. Helicobacter pylori caused inflammation and ulcers in the stomach and digestive tract. The disclosed peptides can be used to treat such inflammation, by topical, systemic, or other modes of administration.

Edema is a common symptom of inflammation. The disclosed peptides can be used to treat edema, such as that caused by toxins, by infectious agents, by irritation, by cardiovascular disorders, by electrolyte imbalance, or by other causes.

Chronic inflammation is also seen in neurodegenerative diseases or disorders. Accordingly, the disclosed peptides can be used to treat such inflammation as occurs in Parkinson's Disease, Huntington's Disease, Alzheimer's Disease, amyotrophic lateral sclerosis, multiple sclerosis, traumatic brain injury, or stroke.

Cancer has a significant inflammatory component, and the disclosed peptides can be used to treat such inflammation.

Intermittent hypoxia can lead to inflammation, followed by liver injury, fibrogenesis and steatosis, steatohepatitis, cirrhosis, and hepatocellular carcinoma.

Diabetes can lead to inflammation, and complications such as diabetic retinopathy and peripheral neuropathy.

Oxidative stress can contribute to various diseases with inflammatory components, such as Alzheimer's disease, Parkinson's disease, amyotrophic lateral sclerosis (ALS), poly glutamine diseases, ischemia, atherosclerosis, bipolar disorder, prion diseases, cancer, diabetes, auto immune disorders, and cardiovascular disorders.

Other diseases for which peptides which inhibit NF κB activity can be used (such as diseases that involve perturbations in the homeostasis of NF κB) include diseases involving dysregulation of NF κB, including Alzheimer's disease, inflammation associated with infection and certain viral infections, including acquired immune deficiency syndrome (AIDS), adult respiratory distress syndrome, Hodgkin's disease, cachexia, various inflammatory diseases such as nephritis, hepatitis, acute renal failure, chronic renal failure, reperfusion disorder in ischemic disease selected from a group consisting of ischemic heart disease, ischemic brain disease and Ischemic lung disease, Sjogren's syndrome, hyaline membrane disease, arthritis including rheumatoid arthritis, cardiac hypertrophy, muscle wasting, catabolic disorders, obesity, fetal growth retardation, hypercholesterolemia, heart disease, chronic heart failure, ischemia/reperfusion, stroke, cerebral aneurysm, angina pectoris, pulmonary disease, cystic fibrosis, acid-induced lung injury, pulmonary hypertension, asthma, chronic obstructive pulmonary disease, scleroderma, kidney disease, glomerular disease, Crohn's disease, colitis, ocular allergy, appendicitis, Paget's disease, pancreatitis, periodontitis, endometriosis, inflammatory bowel disease, skin diseases including psoriasis, anhidrotic ectodermal dysplasia, alcoholic liver disease, gut diseases, peritoneal endometriosis, lupus, Behcet's disease, incontinentia pigmenti, tuberculosis, asthma, inflammatory lung disease, silica-induced diseases, sleep apnea, AIDS, neuropathological diseases, familial amyloidotic polyneuropathy, inflammatory neuropathy, Parkinson's disease, multiple sclerosis, amyotrophic lateral sclerosis, Huntington's disease, cataracts, neuropathic pain, atherosclerosis, type 1 diabetes, type 2 diabetes, leptospirosis, renal disease, glaucoma, retinal disease, ageing, headache, pain, complex regional pain syndrome, cardiac hypertrophy, muscle wasting, catabolic disorders and infarcts and aneurysms. The disclosed peptides can ameliorate, diminish, improve, and/or inhibit unwanted side effects and symptoms, including those which are erythematous, ulcerative, inflammatory, necrotic or erosive dysplasias of muco-cutaneous surfaces, such as those in the oral cavity, the nasal cavity, the gastrointestinal and respiratory tracts, the vagina, and the bladder, mucositis, oral mucositis, denture stomatitis, oral lichen planus, aphthous ulcers, pemphigus, bullous pemphigoid, oral lichen planus, and oral mucous membrane contact dermatitis; herpetiform ulcers, canker sores, digestive mucositis, esophageal mucositis, intestinal mucositis, inflammatory bowel disease, ulcerative colitis and Crohn's disease, aphthous ulcers, pemphigus, bullous pemphigoid, oral lichen planus, and oral mucous membrane contact dermatitis; herpetiform ulcers, canker sores, diseases of the nasal mucous membrane include sinusitis and rhinitis; examples for the bladder include interstitial cystitis and radiation cystitis. Certain diseases such as Behcet syndrome, can affect the mucocutaneous membranes of several regions of the body. Many other ulcerative mucocutaneous diseases are known. There are also painful ulcerative disorders of mucosal surfaces which result as an adverse side-effect in certain therapies, such as chemotherapy and radiation therapy. Examples of such side-effects include mucositis, esophagitis, and radiation proctitis. Mucosal injury may also result from endoscopic procedures.

CANCER AND RELATED DISEASES: The disclosed peptides can be used to treat a wide range of cancers and metastatic disease. Such cancers include lymphoproliferative disorders, lymphomas, leukemias, carcinomas and sarcomas, cancers of the prostate, breast cancers, cervical cancer, uterine cancer, endometrial cancer, bone cancer, gastric and colon cancers, liver cancer, pancreatic cancer, various head and neck cancers, thyroid cancer, cancers of the central and peripheral nervous system, brain cancer, kidney cancer, and skin cancers. The disclosed peptides are particularly effective against oral cancer and oral tumors, as shown in Example 3, FIG. 5, and FIG. 6. The tumor may include pediatric solid tumors, e.g., Wilms' tumor, hepatoblastoma and embryonal rhabdomyosarcoma, wherein each possibility represents a separate embodiment of the present invention. In other embodiments, the tumor includes, but is not limited to, germ cell tumors and trophoblastic tumors (e.g. testicular germ cell tumors, immature teratoma of the ovary, sacrococcygeal tumors, choriocarcinoma and placental site trophoblastic tumors), wherein each possibility represents a separate embodiment of the present invention. According to additional embodiments, the tumor includes, but is not limited to, epithelial adult tumors (e.g. bladder carcinoma, hepatocellular carcinoma, ovarian carcinoma, cervical carcinoma, lung carcinoma, breast carcinoma, squamous cell carcinoma in head and neck, colon carcinoma, renal cell carcinoma and esophageal carcinoma), wherein each possibility represents a separate embodiment of the present invention. In yet further embodiments, the tumor includes, but is not limited to, neurogenic tumors (e.g. astrocytoma, ganglioblastoma and neuroblastoma), wherein each possibility represents a separate embodiment of the present invention. In another embodiment, the tumor is prostate cancer. In another embodiment, the tumor is pancreatic cancer. In other embodiments, the tumor includes, for example, Ewing sarcoma, congenital mesoblastic nephroma, gastric adenocarcinoma, parotid gland adenoid cystic carcinoma, duodenal adenocarcinoma, T-cell leukemia and lymphoma, nasopharyngeal angiofibroma, melanoma, osteosarcoma, uterus cancer and non-small cell lung carcinoma, wherein each possibility represents a separate embodiment of the present invention. The above list is not comprehensive but is provided here to describe the range of diseases that may be addressed by the disclosed inhibitors of NF κB activity and NF κB activation. The disclosed inhibitors of NF κB activation can be used in preventing and treating other diseases that may be found to be treatable by inhibition of NF κB. See also Alam et al., "Loss of keratin 8 phosphorylation leads to increased tumor progression and correlates with clinico-pathological parameters of OSCC patients," PLoS One. 2011; 6 (11):e27767; and Alam et al., "Loss of keratins 8 and 18 leads to alterations in α6β4-integrin-mediated signalling and decreased neoplastic progression in an oral-tumour-derived cell line," J. Cell Sci. 124 (Pt 12):2096-2106 (2011) for discussions relevant to oral tumors and oral cancer.

AGEING: NF κB is closely associated with the process of ageing. Cellular processes that regulate lifespan are subject to modulation by NF κB. Dysfunctional NF κB signaling plays a major role in age-related diseases. NF κB is therefore an important target to address in age-related changes and progeroid diseases. The disclosed NF κB inhibitory peptides are ideally suited to fulfill this need. Parkinson's Disease, Huntington's Disease, and Alzheimer's Diseases are among the diseases associated with ageing that can be treated using peptides of the invention.

AGEING OF SKIN: Skin is the organ that is most exposed to environmental factors such as radiation and chemicals that contribute to DNA damage and aberrant NF κB activation. Recent studies show that genetic manipulation of NF κB reverses signs of ageing in rodent skin. Studies show physical changes in human skin, and in altered gene expression pattern in fibroblasts that show a return to a younger phenotype. The disclosed peptides which inhibit NF κB activity can be used for restoring a youthful phenotype in skin.

FIBROSIS AND SCARRING: The growth factor TGF 31 plays a crucial role in promoting adhesions, fibrosis and scarring during wound healing. NF κB signaling is a major factor in fibrosis and scarring. The disclosed peptide inhibitors of NF κB activity can prevent scarring during incisional wound repair.

PAIN: Pain is the most common ailment of humans and non-human animals. Pain can arise from injury, infection, inflammation, or a host of diseases including inflammatory diseases and cancer. Pain can affect all structures and tissues in the body. The efficacy of the disclosed peptides against pain arises from the ability of these peptides to abrogate the TNF-α-NF-κB nexus which plays a key role in pain. Thus these peptides can be a useful addition to pain therapies.

Direct or indirect interactions of inflammatory cytokines (e.g. TNF-α, IL-1β, IL-6) are crucial factors in pain. The inflammatory cytokines TNF-α and IL-6 have been demonstrated to play a direct role in sensitization of nociceptors and the development of mechanical allodynia. These cytokines are regulated by the TNF-α-NF-κB nexus (Bowles et al., Arthritis Rheumatol. 66(3):637-46 (2014); Niederberger and Geisslinger, FASEB J. 22(10):3432-42 (2008)). The crucial role of NF-κB in several pathologies that accompany pain provides evidence that intervention with the NF-κB signaling cascade might have beneficial antinociceptive effects. The NF-κB-activating pathways, in particular the canonical activation, offer several targets for the disclosed peptide inhibitors of NF-κB activity. Inhibition of TNF-α-induced activation of NF-κB is described below in Example 1, using a luciferase assay. Studies using such luciferase assays are described in Wang et al., Asian Pac. J. Cancer Prev. 11(1):193-200 (2010); Lewis et al., American Journal of Human Genetics 96:221-234 (2015); and Wei et al., PLOS ONE vol. 9, issue 6, e100515 (June 2014). NF-κB Reporter Luciferase Assay kits are sold commercially by several vendors, such as BPS Bioscience, San Diego, California (NF-κB Reporter Kit Catalog #60614) and QIAGEN, Valencia, California (Cignal Lenti NFκB Reporter (luc) Kit CLS-013L).

To establish the efficacy of the disclosed peptide inhibitors of NF-κB activity in analgesia, hyperalgesia was induced in rat paws with injections of carrageenan. The experiment is as described in Example 5. Injection of carrageenan in a hind paw of rats produced severe hyperalgesia. Subsequent treatment with peptides SEQ ID NO:001, and SEQ ID NO:042 markedly ameliorated nociception in the animals. These data are presented in FIG. 10. The two peptides gave showed nearly identical efficacy. Only the results with peptide SEQ ID NO:042 are shown here.

SEQUELAE OF RADIATION EXPOSURE: The peptides can be used for treatment of the sequelae (after-effects) of radiation, such as tissue damage or changes caused by exposure to ionizing radiation. Radiation can result from exposure to gamma rays, X-rays, and such high-energy particles as neutrons, electrons, and alpha particles. Sources of ionizing radiation may be natural (e.g., radioactive substances such as the element radium or the radioisotopes potassium-40 and carbon-14; cosmic rays at high altitude) or man-made (X-ray machines, nuclear reactors, particle accelerators, nuclear weapons, nuclear waste, etc.).

Exposure to radiation can result in production of toxic oxygen free radicals, which increases oxidative stress. This can be followed by lipid peroxidation in the cell membranes and the replacement of fibrous tissue, and depletion of endogenous antioxidant enzymes and accumulation of iron complexes.

The disclosed peptides can be used to treat radiation-induced diseases and disorders, such as basal cell carcinoma, melanoma, squamous cell carcinoma, radiation dermatitis, radiation burns, radiation induced inflammation, radiation dermatitis, sun burn, injury and atrophy to respiratory epithelia, radiation induced fibrosis in tissues, radiation mucositis in the alimentary canal, radiation enteritis, radiation proctitis, radiation proctosigmoiditis, radiation induced ulcers, radiation-induced heart disease (RIHD) myocardial fibrosis, cardiomyopathy, coronary artery disease, valvular disease, pericardial disease, and arrhythmias, radiation hepatitis, radiation induced arterial stenosis including carotid stenosis, radiogenic cataracts, radiation necrosis, or radiation proctocolitis.

The peptides can be used prophylactically (that is, administered in anticipation of radiation exposure), and therapeutically (that is, administered after radiation exposure). The peptides can be used for treatment of dermal tissues, the alimentary canal, or mucosal tissues. The peptides can be used for radiation burns, radiation induced inflammation, and radiation dermatitis. The peptides can be used for protection against epilation.

The disclosed peptides can be used for prophylaxis and therapy of sunburn and skin damage caused by UV radiation, such as actinic keratosis.

ADDITIONAL EMBODIMENTS

The invention is further described by the following embodiments. The features of each of the embodiments are combinable with any of the other embodiments where appropriate and practical.

Embodiment 1. A composition of matter consisting of peptides that inhibit the activation of NF κB in vitro and in vivo.

Embodiment 2. A composition of matter consisting of peptides that down-regulate in vitro and in vivo, genes whose expression is known to be upregulated by NF κB, thereby mitigating the injurious effects of NF κB activation.

Embodiment 3. A composition of matter consisting of peptides that upregulate genes whose expression is downregulated by NF κB, in vitro and in vivo thereby correcting the injurious effects of NF κB activation.

Embodiment 4. A composition of matter consisting of peptides in Embodiments (1)-(3) that have 4-6 residues including a core sequence of certain contiguous amino acids, such bioactive cores being (1) Xxx-Ala-Pro-Glu, (2) Xxx-Ala-Pro-[D]Glu, (3) Xxx-Ala-Glu-Ala, (4) Xxx-Ala-[D]Glu-Ala, (5) Xxx-Ala-Asn-Ala, and (6) Xxx-Ala-[D]Asn-Ala in which the residue Xxx immediately on the N-terminus of the core sequence is one of the following residues: Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, or β-tert-butyl-Ala.

Embodiment 5. Peptides in Embodiments (1)-(4) that have 4-10 residues including a core sequence as defined in embodiment (4).

Embodiment 6. Peptides in Embodiments (1)-(4) that have 4-20 residues including a core sequence as defined in embodiment (4).

Embodiment 7. Peptides in Embodiments (1) to (6) that contain Core sequence 1: Xxx-Ala-Pro-Glu, where Xxx is Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, or β-tert-butyl-Ala.

Embodiment 8. Peptides in Embodiments (1) to (6) that contain a Core sequence 2: Xxx-Ala-[D]Pro-Glu, where Xxx is Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, or β-tert-butyl-Ala.

Embodiment 9. Peptides in Embodiments (1) to (6) that contain Core sequence 3: Xxx-Ala-Glu-Ala, where Xxx is Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, or β-tert-butyl-Ala.

Embodiment 10. Peptides in Embodiments (1) to (6) that contain Core sequence 3: Xxx-Ala-[D]Glu-Ala, where Xxx is Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, or β-tert-butyl-Ala.

Embodiment 11. Peptides in Embodiments (1) to (6) that contain Core sequence 5: Xxx-Ala-Asn-Ala, where Xxx is Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, or β-tert-butyl-Ala.

Embodiment 12. Peptides in Embodiments (1) to (6) which contain Core sequence 6: Xxx-Ala-[D]Asn-Ala, where Xxx is Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, or β-tert-butyl-Ala.

Embodiment 13. Peptides in Embodiments (1) to (6) in which Pro is replaced with Hyp or by pyroglutamic acid.

Embodiment 14. Peptides in Embodiments (1) to (6) in which Ala is replaced with Ser, N-methyl-Ser, N-methyl-Ala, Nva, N-methyl-Nva, Aab, N-methyl-Aab, Aib, N-methyl-Aib, Allyl-Gly, Sarcosine, propargyl-Gly, Indanyl-Gly, Cyclohexyl-Gly, phenyl-Gly, dehydroalanine, or homovaline.

Embodiment 15. Peptides in Embodiments (1) to (6) in which the residues on the C-terminus of the core sequences described above, may be un-natural amino acids such as 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, or β-tert-butyl-Ala.

Embodiment 16. Peptides in Embodiments (1) to (6) in which the residue on the C-terminus of the core sequences may be un-natural amino acids such as 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, or β-tert-butyl-Ala.

Embodiment 17. Peptides in Embodiments (1) to (6) in which the residues on both the N- and C-terminus of the core sequences described above may be un-natural amino acids such as 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, or β-tert-butyl-Ala.

Embodiment 18. In some embodiments, the total length of the peptide including core sequences may be seven, eight, nine, ten, eleven, twelve, thirteen, fourteen, fifteen, sixteen seventeen, eighteen, nineteen or twenty residues, such that in a peptide NnX(CORE)NcZ, where Nn is the number of residues X on the N-terminal of the core sequence, and Nc is the number of residues Z on the C-terminal of the core sequence, the sum of Nn+Nc+ CORE sequence is five, six, seven, eight, nine, ten, eleven, twelve, thirteen, fourteen, fifteen, sixteen, seventeen, eighteen, nineteen or twenty.

Embodiment 19. In other embodiments, the numbers Nn and Nc may range from zero to sixteen, such that the core sequence may be part of a longer sequence in which the residues X on the N-terminal side and Z on the C-terminal side of the CORE sequence may not be even, thus the peptides may have structures as below:
(CORE)-NcY where the residues Y are zero to sixteen
NnX-(CORE) where the residues X are zero to sixteen
NnX-(CORE)-NcY where the numbers Nn and Nc are independently variable.

Embodiment 20. In peptide inhibitors of NF κB, amino acids making up the residues X and Y are also independently variable and drawn from the Lists of amino acids in FIG. 9 (FIG. 9A and FIG. 9B).

Embodiment 21. Peptides in Embodiments (1) to (6) that have protective groups on the N-terminal, or the C-terminal or on both N- and C-terminal sides.

Embodiment 22. A composition of matter consisting of peptides in embodiment (1) to (6) that are selected from sequence i.d. 1-40, as listed in Table 8.

Embodiment 23. A composition of matter consisting of peptides in embodiments (1) to (6) that are selected from the peptides listed in Table 9.

Embodiment 24. A composition of matter consisting of peptides in embodiment (1) to (21) that follow the structure Xn-(core sequence)-Xm where the sum of n+m is between 6 and 20, where the amino acids X are from the group of natural proteinogenic amino acids.

Embodiment 24A. A composition of matter consisting of peptides in embodiment (1) to (21) that follow the structure Xn-(core sequence)-Xm where the sum of n+m is between 6 and 20, where the amino acids X are from the group of un-natural (non-proteinogenic) amino acids.

Embodiment 25. A composition of matter consisting of peptides and core sequences as described in Embodiments (1) to (18) coupled to polymers, polyethylene glycols, or polysaccharides.

Embodiment 26. A composition of matter consisting of peptides in various embodiments as described above modified to produce pro-drugs that would be transformed to the active form in physiologic milieux.

Embodiment 27. A composition of matter consisting of peptides in various embodiments as described above coupled to a moiety such as propionyl, pentyl, hexyl, cyclopentyl, lipoyl, benzoyl, myristoyl, palmitoyl, stearyl, propargyl, farnesyl, α-eleostearoyl, oligoarginyl, oligolysyl, polyethylene, pluronic etc., to enhance penetration in tissues and dwell time in tissues and organs including the alimentary canal, and facilitate entry into nervous system and its tissues.

Embodiment 28. A composition of matter consisting of peptides in various embodiments as described above containing additional groups to protect them from proteolysis in body fluids, including addition of one or more [D]-amino acid, acetylation of the N-terminal group, modification of the N-terminal amino group with 1-amino-cyclohexane-carboxylic acid, modification of the N-terminal amino group with β-acetyl-2,3-diamino propionic acid.

Embodiment 29. A method of inhibiting the activation of nuclear factor NF-κB in cells in vitro or in vivo, comprising the step of treating said cells with a NF κB Inhibitor peptide compounds as described in (1)-(26).

Embodiment 30. A therapeutic or prophylactic composition comprising a pharmaceutically acceptable carrier and a peptide inhibitor of NF κB activation as described in (1)-(26).

Embodiment 31. A method for treating a subject suffering from or at risk of suffering from a disease caused by perturbations in NF κB activation as enumerated in paragraphs [0061] to [0068], using one or more NF κB inhibitor as described in embodiments (1) to (26), in pharmaceutically appropriate formulations, in doses appropriate to the severity of disease.

Embodiment 32. A method for treating a subject suffering from or at risk of suffering from a disease caused by NF κB activation as enumerated in paragraphs [0061] to [0068], using one or more NF κB inhibitor as described in embodiments (1) to (26), in combination with other therapeutic drugs or compounds, or concomitant with procedures such as radiation therapy, in pharmaceutically appropriate formulations, in doses appropriate to the severity of disease.

EXAMPLES

The following examples are provided to illustrate, but not limit, the invention.

Example 1

Inhibition by Peptides of TNF-α-Induced and Constitutive Activation of NF κB

SiHa cells (ATCC HTB-35) were seeded in the wells of a 96 well plate at 25,000 cells/well. The cells were transfected with the respective luciferase construct (p-SBE4, p-ARE-Luc in combination with FAST-1, p-NF κB) using Lipofectamine 2000 reagent (Invitrogen Technologies Inc.), as per the manufacturer's instructions. 18 hours post transfection; the cells were subjected to the respective treatments such as TGF-β, TNF-α, and the peptides. After 24 hours of treatment, the plates were removed from the incubator; medium from the cells was discarded. The wells were filled with 50 μl of PLB (passive lysis buffer) provided along with the Promega dual luciferase assay kit. The luciferase assay was performed as per the supplier's instruction manual, after transferring the lysates to a white plate for luminescence measurements. Expression of luciferase, and measurement of the resulting luminescence, thus provides a measurement of the extent of expression of NF-κB.

As per the data in FIG. 2, the disclosed peptides inhibit TNF-α-activation of NF-κB. As per the data in FIG. 3, the disclosed peptide LFAP$_{[D]}$EA (SEQ ID NO:013) inhibits both TNF-α-induced and constitutive activation of NF-κB. The ratio between the firely/renilla luciferase was used to compare TNF-α induced activation of NF-κB over constitutive NF-κB activity.

Example 2

Inhibition by Peptides of Phosphorylation of p65 Subunit of NF κB

Inhibition of the activation of NF-κB requires numerous phosphorylation events catalyzed by serine threonine kinases (STKs) (see FIG. 1). Many of these steps contribute to the two-step release of NF-κB subunits from a complex with the inhibitory protein IκB. To dissociate the complex between IKB and NF-κB, IKB must be phosphorylated by specific STKs, IKKBα and IKKBβ. IKKBα and IKKBβ are present in inactive complex with the protein IKKγ. Several STKs listed in FIG. 1 phosphorylate IKKBα and IKKBβ, resulting in the release and activation of these STKs. Released from the inhibitory complex, IKKBα and IKKBβ phosphorylate IκB, resulting in its dissociation from NF-κB. The subunits of NF-κB are then subjected to phosphorylation and translocation into the nucleus where they act as transcriptional regulators of gene expression.

The overall inhibition of NF-κB activation by TNF-α supports the concept that the peptides inhibit the phosphorylation of NF-κB subunits, possibly by inhibition of at least one of the numerous STKs involved in the release of IKKBα, IKKBβ.

Figures 3, 4:
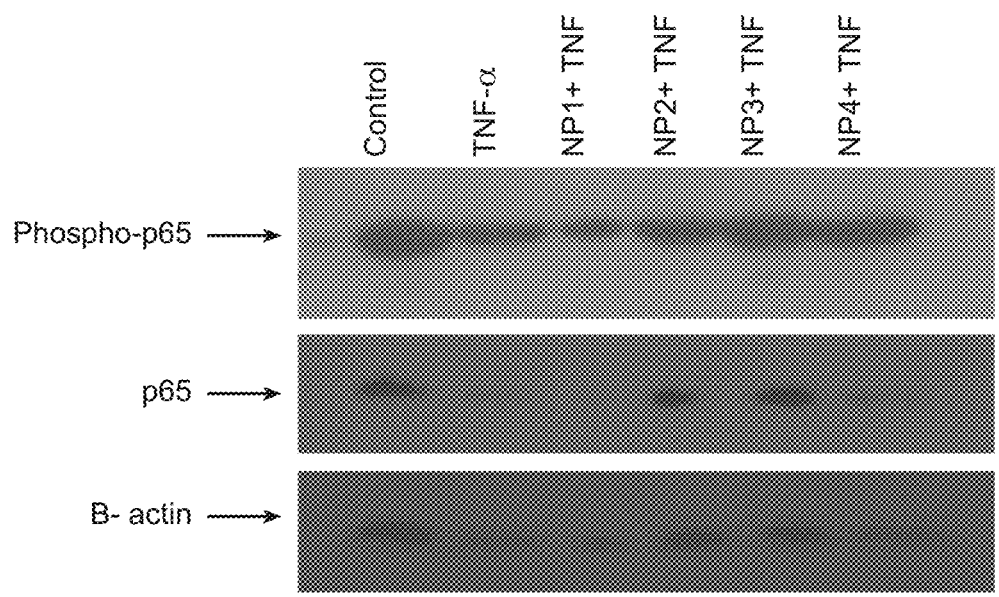
FIG. 3 shows inhibition of both TNF α-induced and constitutive activation of NF κB by the disclosed peptides. Firefly luciferase reading shows TNF α-stimulated NF κB levels, while Renella luciferase shows constitutive levels of NF κB activation.
FIG. 4 shows a Western blot for p65 (NF κB) activation and inhibition in SiHa cells. The disclosed peptides inhibit the phosphorylation of the p65 subunit of NF κB. Peptide NP-1 is SEQ ID NO:008 (LWAEAK); Peptide NP-2 is SEQ ID NO:015 (TNWAEN); Peptide NP-3 is SEQ ID NO:016 (TWAPES); Peptide NP-4 is SEQ ID NO:017 (TWSPEL).

To confirm this concept, the phosphorylation of subunits of NF-κB was examined using an ELISA kit assay. In vivo and in vitro studies showed marked inhibition of phosphorylation of NF-κB subunits p50, p65, and the kinases IKBα and IKKβ. FIG. 4 shows a Western blot demonstrating the inhibition of phosphorylation by the peptides of SEQ ID NO: 008 (LWAEAK), SEQ ID NO: 015 (TNWAEN), SEQ ID NO: 016 (TWAPES), and SEQ ID NO: 017 (TWSPEL).

Example 3

Treatment of Oral Tumor Oral Cancer: Regression of Tumor in Hamster Cheek by Peptide Inhibitor of NF κB Activity; Histological Examination of Tumor Tissue A peptide inhibitor of NF κB activity disclosed herein was tested for treatment of induced oral tumors. Male Syrian hamsters aged 8 to 10 weeks weighing between 100 and 110 g were used. The animals were fed a standard pellet diet and water ad libitum, and were maintained in accordance with applicable ethical and institutional guidelines. The animals were randomized into 10 groups of 8 animals each, and the right buccal pouches of hamsters in groups 1-5 were painted with 0.5% 7,12-dimethylbenz[a]anthracene (DMBA) in liquid paraffin three times a week for 12 weeks.

Mucoadhesive gels containing peptides were prepared by slowly adding Noveon AA1 (0.675% w/w) and Carbopol 971P NF (0.788% w/w) to purified water. The mixture was stirred at 1,025 rpm for one hour to allow full rehydration. Then 0.9% w/w glycerine, 2-phenoxyethanol, benzyl alcohol, and EDTA were added, followed by mixing at 875 rpm for one hour at room temperature. Finally, the desired peptide was added to the gel, and the gel mixed at 875 rpm for one hour to homogenize the gel (Kavitha et al., Biochimie 102:56-67 (2014); Mallery et al., Pharm Res. 24(4):728-737 (2007)).

Hamsters in Group 1 received no further treatment. For hamsters in Groups 2 and 3, peptide gel was applied topically to the right buccal pouches of the hamsters from the 12th to the 18th week daily at concentrations of 10 microgram/ml (2.35 microgram dosage of peptide per application) and 100 microgram/ml (23.5 microgram dosage of peptide per application) respectively. Another group of animals painted with liquid paraffin alone served as control. The experiment was terminated after 18 weeks and all animals were sacrificed by cervical dislocation after an overnight fast.

Figure 5A:
FIG. 5A, FIG. 5B, and FIG. 5C show the regression of a chemically induced tumor in hamster cheek by a NF κB inhibitor peptide applied topically.
Figure 5B:
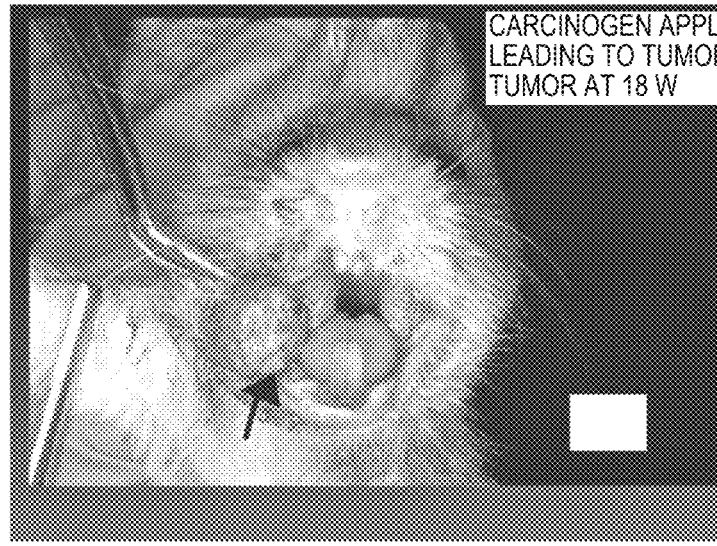
Figure 5C:
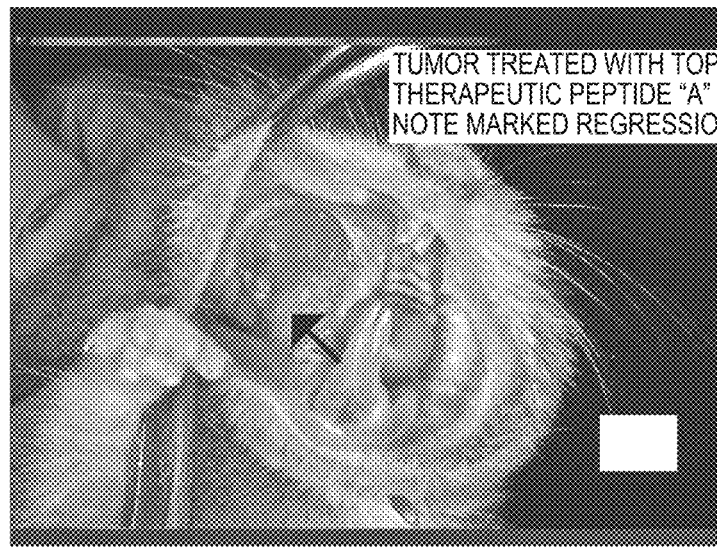

FIG. 5 shows the results of treatment of a chemically induced tumor in hamster cheek by a NF κB inhibitor peptide applied topically. FIG. 5A shows a control animal, with a normal cheek. FIG. 5B shows a tumor in the hamster cheek induced by application of DMBA. FIG. 5C shows the cheek of a hamster where DMBA was applied to the cheek to induce a tumor. The cheek was subsequently treated by topical application of peptide inhibitor of NF κB activity, ANVAENA (SEQ ID NO:042), for six weeks, at an applied concentration of 100 microgram/ml (23.5 microgram dosage of peptide per application), demonstrating marked inhibition of tumor growth as compared to FIG. 5B.

FIG. 6A shows a histological sample of tissue from a control animal, while FIG. 6B shows a histological sample from tissue after application of DMBA. FIG. 6C shows a histological sample of tissue treated with DMBA, then with the peptide inhibitor of NF κB activity, ANVAENA (SEQ ID NO:042), which demonstrates an effect at the microscopic level of treatment with the peptide.

Example 4

Gene Microarray Analysis of Gene Expression

NF κB inhibitor peptide SEQ ID NO: 010 down-regulates expression of genes known to be associated with the pathobiological action of NF κB and TNF α. FIG. 7 shows genes the expression of which may be affected by SEQ ID NO: 010, based on a gene microarray analysis of gene expression in human dermal fibroblasts exposed to 1.0 micromolar peptide SEQ ID NO: 010. The upregulation of certain target genes by the transcription factor NF κB is a major contributory factor in diseases and disorders attributed to the activation of NF κB. The downregulation of these genes by the NF κB inhibitor peptides can be expected to provide prophylaxis and therapy for such disorders. (The downregulation of some of these genes was confirmed in vivo in a study to examine the efficacy of NF κB inhibitor peptide, SEQ ID NO: 010.) Certain genes were also tested in a rodent squamous cell carcinoma model, by PCR and by immunoblots (mRNA levels were monitored by PCR and the corresponding protein levels were monitored by immunoblots).

Example 5

Analgesic Effect of Disclosed Peptides

Figure 10:
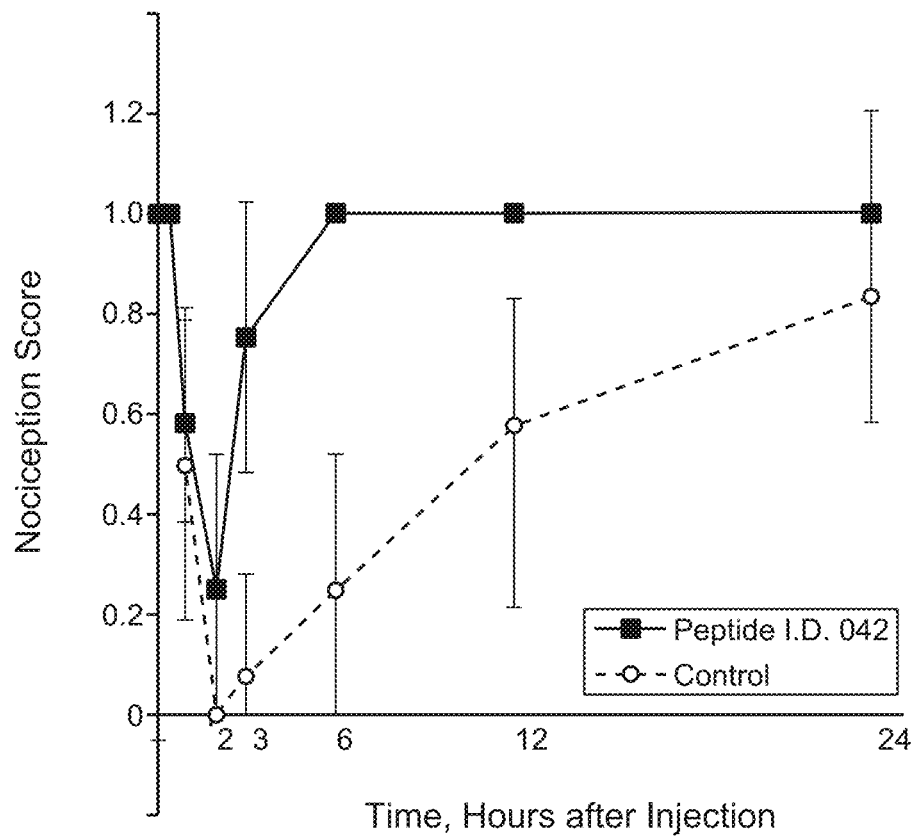
FIG. 10 shows amelioration of hyperalgesia by the peptide ANVAENA (SEQ ID NO: 042).

The ability of the disclosed peptides to affect nociception was determined using a modification of the Randell-Selitto paw withdrawal method. Groups (n=6) of healthy albino rats were injected in the paw with 3 mg carrageenan alone in phosphate buffered saline (PBS). The control group received only PBS and these animals did not show significant edema. As inflammation became obvious (15 min) in carrageenan-treated animals, test animals were injected with 70 nanogram of peptide SEQ ID NO:001, or peptide SEQ ID NO:042 in PBS. The animals are allowed to walk on a metal grid before and after injecting the drugs and the observations were noted. The scoring system was based on normal gait=1, marked limping=0.5, and three legged gait=0. The scores are transformed into percent analgesia and subjected to statistical analysis. The two peptides gave very similar results. The results shown in FIG. 10 are from animals treated with peptide SEQ ID NO:042.

Example 6

Anti-Inflammatory Effect of Disclosed Peptides

Groups (n=6) of healthy albino rats were injected in the paw with 3 mg carrageenan alone in phosphate buffered saline (PBS). The control group received only PBS and these animals did not show significant edema. As inflammation became obvious (15 min) in carrageenan-treated animals, test animals were injected with 70 nanogram of peptide SEQ ID NO:001, or peptide SEQ ID NO:042 in PBS. A plethysmometer was used to measure paw edema at 0, 0.5, 1.0, 2.0, 3.0, 6.0, 12.0, and 24 hours after injections. The two peptides showed nearly identical patterns, and only the data from peptide SEQ ID NO:042 are shown here. Initially there was no significant difference in edema between the carrageenan-treated and carrageenan+peptide treated animals, but at 2 h animals receiving the peptide displayed significant decrease in edema and inflammation. By 3.0 h, inflammation subsided almost completely and no inflammation was noted up to 24 h post injection in peptide treated animals. In contrast, animals not receiving peptide continued to show significant inflammation at all time points. These data show the high efficacy of the peptide as a potent anti-inflammatory agent with an efficacy approximately 103 times greater than that reported for celecoxib (Francischi et al., Br. J. Pharmacol. 137(6):837-44 (2002)).

Example 7

A. Treatment of Mucositis with Disclosed Peptides

Oral mucositis is induced in experimental hamsters by administration of radiation (see Wu et al., "A novel peptide to treat oral mucositis blocks endothelial and epithelial cell apoptosis," Int. J. Radiat. Oncol. Biol. Phys. 83(3):e409-15 (2012); Alvarez et al., "Preclinical characterization of CG53135 (FGF-20) in radiation and concomitant chemotherapy/radiation-induced oral mucositis," Clin. Cancer Res. 9:3454-3461 (2003); and Murphy et al., "Efficacy of superoxide dismutase mimetic M40403 in attenuating radiation-induced oral mucositis in hamsters" Clin. Cancer Res. 14:4292-4297 (2008)). Radiation is administered in a single dose of radiation (for example, 40 Gy at a rate of 3.2 Gy/min), or in fractionated doses (for example, two doses of 7.5 Gy each day for four days, followed by three days with no radiation, followed by two doses of 7.5 Gy each day for four additional days).

Mucoadhesive gels containing a peptide as disclosed herein are prepared as in Example 3. Peptide gel is administered to the buccal pouch of groups of hamsters daily at concentrations of 10 microgram/ml (2.35 microgram dosage of peptide per application) and 100 microgram/ml (23.5 microgram dosage of peptide per application) respectively. One group of hamsters is treated starting five days before commencing irradiation; another group of hamsters is treated started the day before commencing irradiation. Additional groups of hamsters serve as vehicle controls, scrambled peptide controls, irradiated untreated controls, and non-irradiated untreated controls. Another group of hamsters may be used as a non-irradiated control group which is treated with peptide gel.

The buccal pouches of the hamsters are evaluated, with evaluation starting before treatment and continuing through the end of radiation therapy and for at least a week thereafter. Evaluation is conducted according to standard protocols (see, for example, Alvarez et al., "Preclinical characterization of CG53135 (FGF-20) in radiation and concomitant chemotherapy/radiation-induced oral mucositis," Clin. Cancer Res. 9:3454-3461 (2003)), and the efficacy of the disclosed peptides in the treatment of oral mucositis is assessed.

B. Clinical Study of Mucositis Treatment with Disclosed Peptides

Peptides are studied for treatment of mucositis on head and neck cancer patients about to undergo chemo-radiation therapy. Informed consent will be obtained from all subjects, and the study will comply with all applicable regulatory, ethical, and institutional guidelines. The patients are divided into four groups. The radiation will be 2Gy/day for 5 days/week for 7 weeks, during which they will receive one dose of cisplatin each of the seven weeks. Each of the four groups will be randomized 1:1 to peptide treatment or placebo. In addition to a medical history, physical examination and blood and urine tests, each patient will undergo a complete oral examination to establish a baseline condition and to determine if any dental work needs to be performed prior to treatment. Vital signs will be obtained weekly. Blood and urine laboratory studies will be obtained at the end of the seventh week of therapy and day 70. A physical examination will be done at the end of week seven of therapy and on day 70. Twenty ml of solution of peptide, such as ANVAENA (SEQ ID NO:042), will be administered daily from three days prior to radiation therapy to 21 days post therapy. Patients will complete a daily oral mucosa questionnaire and their mouth will be examined twice a week by a trained observer. Subjects will complete a daily self-administered questionnaire grading his/her mouth soreness. The active formulation consists of varying concentrations of peptide in USP/EP 1% carboxymethyl cellulose sodium, and 1% glycerin in normal saline. The placebo will be a solution similar in color, taste and mouth feel to the peptide solution.

Prior to the morning meal, the patient will swish 20 ml peptide solution or placebo in their mouth for one minute and then expectorate the remainder. The patient will refrain from eating or drinking for another hour. The dose will be administered daily from three days prior to initiation of radiation therapy to 21 days following discontinuation of therapy. Group 1 will receive 0.5 mg/ml peptide (about 0.75 micromolar) gel or placebo; group 2-1.0 mg/ml (about 1.5 micromolar) or placebo, group 3-1.5 mg/ml (about 2.25 micromolar) or placebo, and group 4-2.0 mg/ml (about 3 micromolar) or placebo. On the first day of each week of radiation therapy subjects will receive 40 mg/m$^2$ cisplatin. One hour after first dose administration and before the morning meal, subjects will have their vital signs taken again and recorded. In addition to the times for vital signs defined above, the subjects' vital signs will also be obtained during the weekly visit to have his/her mouth examined.

Efficacy of peptide treatment is assessed by the difference between the number of peptide-treated and placebo subjects who develop WHO grades 3 and 4 adverse events (WHO Handbook, 1979). Additional assessments are based on time to WHO grade 3, time to first narcotic use, amount of narcotic use, global assessment VAS (visual analog scale), incidence of bacterial infection, incidence of fungal infection, need for parenteral nutrition, sum of MTS alternative scores, Question 2 (Stiff et al., Bone Marrow Transplant. 37(4):393-401 (2006)), and incidence of adverse effects. Peptides of the invention which show statistically significant effects are used for mucositis treatment.

Example 8

Peptide Effect on Smad2 Signaling

As illustrated in FIG. 12A, both TGF-β and peptide LIANAK (SEQ ID NO:060, referred to as "Leu-6 Lys" in the figure) induce phosphorylation of smad2 in HepG2 cells which contain intact TGF-β signaling network with both TBRII and TBRI present. TGF-β signaling requires both receptors.

MCF-7 cells do not express TBRII, and do not respond to TGF-β. In contrast peptide LIANAK (SEQ ID NO:060, referred to as "Leu-6 Lys" in the figure) induces TGF-β signaling in these cells by causing the phosphorylation of smad2 indicating that it does not bind to TBRII, an essential step in the action of TGF-β (see FIG. 12B). In this experiment SB431542, an inhibitor of TBRI, did not prevent smad2 phosphorylation, indicating that the effect of the peptide on TGF-β signaling may be independent of the receptors.

Phosphorylation of smad2 was determined by Enzyme-Linked Immunosorbent Assay (ELISA) using a kit obtained from a commercial source. The Phospho-Smad2 Sandwich ELISA Kit is a solid phase sandwich enzyme-linked immunosorbent assay (ELISA) that recognizes endogenous levels of phospho-Smad2 (Ser465/467) and Smad3 (Ser423/425) proteins. A Smad2/3 Mouse Antibody has been coated on the microwells. After incubation with cell lysates, Smad2/3 proteins (phospho and nonphospho) are captured by the coated antibody. Following extensive washing, a Phospho-Smad2 (Ser465/467)/Smad3 (Ser423/425) Detection Antibody is added to detect captured phospho-Smad2 (Ser465/467) and phospho-Smad3 (Ser423/425) proteins. Anti-rabbit IgG, HRP-linked Antibody is then used to recognize the bound detection antibody. HRP substrate, TMB, is added to develop color. The magnitude of the absorbance for this developed color is proportional to the quantity of phospho-Smad2 (Ser465/467) and phospho-Smad3 (Ser423/425) proteins.

Example 9

Peptides Alter Cell Cycle

Cell cycle analysis was performed in oral cancer cell line AW 13516 after treatment with TGF-β alone, peptide alone or in combination. Cell cycle analysis was carried out using flow cytometry (Guava Technologies) using reagent kits provided by the instrument maker. The samples were prepared after propidium iodide staining and flow cytometric analysis was performed. Data is shown in Table 1 below. TGF-β causes G1 arrest in cells as expected. The disclosed peptides in contrast markedly shortened the G1 phase and prolonged the S-phase, promoting a more faithful synthesis of DNA prior to cell division. Thus, the disclosed peptides have effects which differ from the effects of growth factors.

TABLE 1

| TREATMENT | % CELLS IN Go Phase | % CELLS IN G1 Phase | % CELLS IN S Phase | % CELLS IN M Phase |
| --- | --- | --- | --- | --- |
| Untreated | 0.40 | 74.87 | 10.67 | 14.06 |
| TGF-β | 8.32 | 79.83 | 3.62 | 8.23 |
| SEQ ID NO: 042 | 2.02 | 62.73 | 16.14 | 19.10 |
| SEQ ID NO: 057 | 14.59 | 52.59 | 21.63 | 11.18 |
| SEQ ID NO: 061 | 2.33 | 60.05 | 19.03 | 18.59 |
| SEQ ID NO: 013 | 2.87 | 62.05 | 20.21 | 14.86 |
| SEQ ID NO: 014 | 3.19 | 62.69 | 19.78 | 13.52 |

The disclosures of all publications, patents, patent applications and published patent applications referred to herein by an identifying citation are hereby incorporated herein by reference in their entirety. Web sites references using "World-Wide-Web" at the beginning of the Uniform Resource Locator (URL) can be accessed by replacing "World-Wide-Web" with www.

Although the foregoing invention has been described in some detail by way of illustration and example for purposes of clarity of understanding, it is apparent to those skilled in the art that certain changes and modifications will be practiced. Therefore, the description and examples should not be construed as limiting the scope of the invention.

```
                          SEQUENCE LISTING

Sequence total quantity: 115
SEQ ID NO: 1            moltype = AA  length = 6
FEATURE                 Location/Qualifiers
REGION                  1..6
                        note = Synthetic Construct
source                  1..6
                        mol_type = protein
                        organism = synthetic construct
SEQUENCE: 1
YMAPEV                                                                  6

SEQ ID NO: 2            moltype = AA  length = 6
FEATURE                 Location/Qualifiers
REGION                  1..6
                        note = Synthetic Construct
source                  1..6
                        mol_type = protein
                        organism = synthetic construct
SEQUENCE: 2
IIAPEG                                                                  6

SEQ ID NO: 3            moltype = AA  length = 6
FEATURE                 Location/Qualifiers
REGION                  1..6
                        note = Synthetic Construct
source                  1..6
                        mol_type = protein
                        organism = synthetic construct
SEQUENCE: 3
EIAEAL                                                                  6

SEQ ID NO: 4            moltype = AA  length = 6
FEATURE                 Location/Qualifiers
REGION                  1..6
                        note = Synthetic Construct
source                  1..6
                        mol_type = protein
                        organism = synthetic construct
SEQUENCE: 4
SNVAEA                                                                  6

SEQ ID NO: 5            moltype = AA  length = 6
FEATURE                 Location/Qualifiers
REGION                  1..6
                        note = Synthetic Construct
source                  1..6
```

```
                        mol_type = protein
                        organism = synthetic construct
SEQUENCE: 5
ANIAEA                                                                    6

SEQ ID NO: 6            moltype = AA  length = 6
FEATURE                 Location/Qualifiers
REGION                  1..6
                        note = Synthetic Construct
source                  1..6
                        mol_type = protein
                        organism = synthetic construct
SEQUENCE: 6
ANMAEN                                                                    6

SEQ ID NO: 7            moltype = AA  length = 6
FEATURE                 Location/Qualifiers
REGION                  1..6
                        note = Synthetic Construct
source                  1..6
                        mol_type = protein
                        organism = synthetic construct
SEQUENCE: 7
NWAENA                                                                    6

SEQ ID NO: 8            moltype = AA  length = 6
FEATURE                 Location/Qualifiers
REGION                  1..6
                        note = Synthetic Construct
source                  1..6
                        mol_type = protein
                        organism = synthetic construct
SEQUENCE: 8
LWAEAK                                                                    6

SEQ ID NO: 9            moltype = AA  length = 6
FEATURE                 Location/Qualifiers
REGION                  1..6
                        note = Synthetic Construct
source                  1..6
                        mol_type = protein
                        organism = synthetic construct
SEQUENCE: 9
LIAEAK                                                                    6

SEQ ID NO: 10           moltype = AA  length = 6
FEATURE                 Location/Qualifiers
REGION                  1..6
                        note = Synthetic Construct
source                  1..6
                        mol_type = protein
                        organism = synthetic construct
SEQUENCE: 10
NVAENA                                                                    6

SEQ ID NO: 11           moltype = AA  length = 6
FEATURE                 Location/Qualifiers
REGION                  1..6
                        note = Synthetic Construct
source                  1..6
                        mol_type = protein
                        organism = synthetic construct
SEQUENCE: 11
LVAEAH                                                                    6

SEQ ID NO: 12           moltype = AA  length = 6
FEATURE                 Location/Qualifiers
REGION                  1..6
                        note = Synthetic Construct
source                  1..6
                        mol_type = protein
                        organism = synthetic construct
SEQUENCE: 12
LIANAK                                                                    6

SEQ ID NO: 13           moltype = AA  length = 6
FEATURE                 Location/Qualifiers
REGION                  1..6
                        note = Synthetic Construct
```

```
MOD_RES                  5
                         note = Xaa = D-Glutamic acid
source                   1..6
                         mol_type = protein
                         organism = synthetic construct
SEQUENCE: 13
LFAPXA                                                                    6

SEQ ID NO: 14            moltype = AA   length = 6
FEATURE                  Location/Qualifiers
REGION                   1..6
                         note = Synthetic Construct
MOD_RES                  5
                         note = Xaa = D-Glutamic acid
source                   1..6
                         mol_type = protein
                         organism = synthetic construct
SEQUENCE: 14
LIAPXA                                                                    6

SEQ ID NO: 15            moltype = AA   length = 6
FEATURE                  Location/Qualifiers
REGION                   1..6
                         note = Synthetic Construct
source                   1..6
                         mol_type = protein
                         organism = synthetic construct
SEQUENCE: 15
TNWAEN                                                                    6

SEQ ID NO: 16            moltype = AA   length = 6
FEATURE                  Location/Qualifiers
REGION                   1..6
                         note = Synthetic Construct
source                   1..6
                         mol_type = protein
                         organism = synthetic construct
SEQUENCE: 16
TWAPES                                                                    6

SEQ ID NO: 17            moltype = AA   length = 6
FEATURE                  Location/Qualifiers
REGION                   1..6
                         note = Synthetic Construct
source                   1..6
                         mol_type = protein
                         organism = synthetic construct
SEQUENCE: 17
TWSPEL                                                                    6

SEQ ID NO: 18            moltype = AA   length = 6
FEATURE                  Location/Qualifiers
REGION                   1..6
                         note = Synthetic Construct
MOD_RES                  6
                         note = Xaa = N-methyl-Alanine
source                   1..6
                         mol_type = protein
                         organism = synthetic construct
SEQUENCE: 18
SWAEAX                                                                    6

SEQ ID NO: 19            moltype = AA   length = 6
FEATURE                  Location/Qualifiers
REGION                   1..6
                         note = Synthetic Construct
MOD_RES                  4
                         note = Xaa = D-Glutamic acid
source                   1..6
                         mol_type = protein
                         organism = synthetic construct
SEQUENCE: 19
SWAXAS                                                                    6

SEQ ID NO: 20            moltype = AA   length = 6
FEATURE                  Location/Qualifiers
REGION                   1..6
                         note = Synthetic Construct
source                   1..6
```

```
                              mol_type = protein
                              organism = synthetic construct
SEQUENCE: 20
AWAEAK                                                                6

SEQ ID NO: 21                 moltype = AA   length = 6
FEATURE                       Location/Qualifiers
REGION                        1..6
                              note = Synthetic Construct
MOD_RES                       4
                              note = Xaa = D-Glutamic acid
source                        1..6
                              mol_type = protein
                              organism = synthetic construct
SEQUENCE: 21
AWAXAK                                                                6

SEQ ID NO: 22                 moltype = AA   length = 6
FEATURE                       Location/Qualifiers
REGION                        1..6
                              note = Synthetic Construct
source                        1..6
                              mol_type = protein
                              organism = synthetic construct
SEQUENCE: 22
AWANAK                                                                6

SEQ ID NO: 23                 moltype = AA   length = 6
FEATURE                       Location/Qualifiers
REGION                        1..6
                              note = Synthetic Construct
MOD_RES                       4
                              note = Xaa = D-Asparagine
source                        1..6
                              mol_type = protein
                              organism = synthetic construct
SEQUENCE: 23
AWAXAK                                                                6

SEQ ID NO: 24                 moltype = AA   length = 6
FEATURE                       Location/Qualifiers
REGION                        1..6
                              note = Synthetic Construct
source                        1..6
                              mol_type = protein
                              organism = synthetic construct
SEQUENCE: 24
AWAPEA                                                                6

SEQ ID NO: 25                 moltype = AA   length = 6
FEATURE                       Location/Qualifiers
REGION                        1..6
                              note = Synthetic Construct
MOD_RES                       5
                              note = Xaa = D-Glutamic acid
source                        1..6
                              mol_type = protein
                              organism = synthetic construct
SEQUENCE: 25
AWAPXA                                                                6

SEQ ID NO: 26                 moltype = AA   length = 6
FEATURE                       Location/Qualifiers
REGION                        1..6
                              note = Synthetic Construct
source                        1..6
                              mol_type = protein
                              organism = synthetic construct
SEQUENCE: 26
PSAPEN                                                                6

SEQ ID NO: 27                 moltype = AA   length = 6
FEATURE                       Location/Qualifiers
REGION                        1..6
                              note = Synthetic Construct
source                        1..6
                              mol_type = protein
                              organism = synthetic construct
SEQUENCE: 27
```

```
HMAPEV                                                                        6

SEQ ID NO: 28          moltype = AA   length = 6
FEATURE                Location/Qualifiers
REGION                 1..6
                       note = Synthetic Construct
source                 1..6
                       mol_type = protein
                       organism = synthetic construct
SEQUENCE: 28
YIAPEV                                                                        6

SEQ ID NO: 29          moltype = AA   length = 6
FEATURE                Location/Qualifiers
REGION                 1..6
                       note = Synthetic Construct
source                 1..6
                       mol_type = protein
                       organism = synthetic construct
SEQUENCE: 29
KAPEPL                                                                        6

SEQ ID NO: 30          moltype = AA   length = 6
FEATURE                Location/Qualifiers
REGION                 1..6
                       note = Synthetic Construct
source                 1..6
                       mol_type = protein
                       organism = synthetic construct
SEQUENCE: 30
LVAEAK                                                                        6

SEQ ID NO: 31          moltype = AA   length = 6
FEATURE                Location/Qualifiers
REGION                 1..6
                       note = Synthetic Construct
source                 1..6
                       mol_type = protein
                       organism = synthetic construct
SEQUENCE: 31
WMAPET                                                                        6

SEQ ID NO: 32          moltype = AA   length = 6
FEATURE                Location/Qualifiers
REGION                 1..6
                       note = Synthetic Construct
source                 1..6
                       mol_type = protein
                       organism = synthetic construct
SEQUENCE: 32
EAPEDL                                                                        6

SEQ ID NO: 33          moltype = AA   length = 6
FEATURE                Location/Qualifiers
REGION                 1..6
                       note = Synthetic Construct
source                 1..6
                       mol_type = protein
                       organism = synthetic construct
SEQUENCE: 33
DVAPED                                                                        6

SEQ ID NO: 34          moltype = AA   length = 6
FEATURE                Location/Qualifiers
REGION                 1..6
                       note = Synthetic Construct
source                 1..6
                       mol_type = protein
                       organism = synthetic construct
SEQUENCE: 34
YLAPEV                                                                        6

SEQ ID NO: 35          moltype = AA   length = 6
FEATURE                Location/Qualifiers
REGION                 1..6
                       note = Synthetic Construct
source                 1..6
                       mol_type = protein
                       organism = synthetic construct
```

```
SEQUENCE: 35
YMAPEH                                                                      6

SEQ ID NO: 36           moltype = AA  length = 6
FEATURE                 Location/Qualifiers
REGION                  1..6
                        note = Synthetic Construct
source                  1..6
                        mol_type = protein
                        organism = synthetic construct
SEQUENCE: 36
QIAEGM                                                                      6

SEQ ID NO: 37           moltype = AA  length = 6
FEATURE                 Location/Qualifiers
REGION                  1..6
                        note = Synthetic Construct
source                  1..6
                        mol_type = protein
                        organism = synthetic construct
SEQUENCE: 37
WTAPEA                                                                      6

SEQ ID NO: 38           moltype = AA  length = 6
FEATURE                 Location/Qualifiers
REGION                  1..6
                        note = Synthetic Construct
source                  1..6
                        mol_type = protein
                        organism = synthetic construct
SEQUENCE: 38
WYAPEC                                                                      6

SEQ ID NO: 39           moltype = AA  length = 6
FEATURE                 Location/Qualifiers
REGION                  1..6
                        note = Synthetic Construct
source                  1..6
                        mol_type = protein
                        organism = synthetic construct
SEQUENCE: 39
SNVAEA                                                                      6

SEQ ID NO: 40           moltype = AA  length = 6
FEATURE                 Location/Qualifiers
REGION                  1..6
                        note = Synthetic Construct
source                  1..6
                        mol_type = protein
                        organism = synthetic construct
SEQUENCE: 40
YRAPEI                                                                      6

SEQ ID NO: 41           moltype = AA  length = 6
FEATURE                 Location/Qualifiers
REGION                  1..6
                        note = Synthetic Construct
source                  1..6
                        mol_type = protein
                        organism = synthetic construct
SEQUENCE: 41
ANVAEK                                                                      6

SEQ ID NO: 42           moltype = AA  length = 7
FEATURE                 Location/Qualifiers
REGION                  1..7
                        note = Synthetic Construct
source                  1..7
                        mol_type = protein
                        organism = synthetic construct
SEQUENCE: 42
ANVAENA                                                                     7

SEQ ID NO: 43           moltype = AA  length = 7
FEATURE                 Location/Qualifiers
REGION                  1..7
                        note = Synthetic Construct
source                  1..7
                        mol_type = protein
```

```
                            organism = synthetic construct
SEQUENCE: 43
GGQIANI                                                                 7

SEQ ID NO: 44               moltype = AA  length = 6
FEATURE                     Location/Qualifiers
REGION                      1..6
                            note = Synthetic Construct
MOD_RES                     2
                            note = Xaa = Aminoisobutyric acid
source                      1..6
                            mol_type = protein
                            organism = synthetic construct
SEQUENCE: 44
IXAEAK                                                                  6

SEQ ID NO: 45               moltype = AA  length = 6
FEATURE                     Location/Qualifiers
REGION                      1..6
                            note = Synthetic Construct
MOD_RES                     3
                            note = Xaa = N-methyl-Alanine
source                      1..6
                            mol_type = protein
                            organism = synthetic construct
SEQUENCE: 45
IIXEAK                                                                  6

SEQ ID NO: 46               moltype = AA  length = 8
FEATURE                     Location/Qualifiers
REGION                      1..8
                            note = Synthetic Construct
MOD_RES                     7
                            note = Xaa = beta-Alanine
source                      1..8
                            mol_type = protein
                            organism = synthetic construct
SEQUENCE: 46
IWGLDGXK                                                                8

SEQ ID NO: 47               moltype = AA  length = 6
FEATURE                     Location/Qualifiers
REGION                      1..6
                            note = Synthetic Construct
MOD_RES                     3
                            note = Xaa = N-methyl-Alanine
source                      1..6
                            mol_type = protein
                            organism = synthetic construct
SEQUENCE: 47
IIXEAK                                                                  6

SEQ ID NO: 48               moltype = AA  length = 6
FEATURE                     Location/Qualifiers
REGION                      1..6
                            note = Synthetic Construct
MOD_RES                     2
                            note = Xaa = alpha-Aminobutyric acid
source                      1..6
                            mol_type = protein
                            organism = synthetic construct
SEQUENCE: 48
LXAEAK                                                                  6

SEQ ID NO: 49               moltype = AA  length = 6
FEATURE                     Location/Qualifiers
REGION                      1..6
                            note = Synthetic Construct
MOD_RES                     2
                            note = Xaa = Aminoisobutyric acid
source                      1..6
                            mol_type = protein
                            organism = synthetic construct
SEQUENCE: 49
LXAEAK                                                                  6

SEQ ID NO: 50               moltype = AA  length = 6
FEATURE                     Location/Qualifiers
REGION                      1..6
```

```
                        note = Synthetic Construct
MOD_RES                 3
                        note = Xaa = D-Alanine
source                  1..6
                        mol_type = protein
                        organism = synthetic construct
SEQUENCE: 50
LIXEAK                                                                        6

SEQ ID NO: 51           moltype = AA   length = 6
FEATURE                 Location/Qualifiers
REGION                  1..6
                        note = Synthetic Construct
MOD_RES                 3
                        note = Xaa = N-methyl-Alanine
source                  1..6
                        mol_type = protein
                        organism = synthetic construct
SEQUENCE: 51
LIXEAK                                                                        6

SEQ ID NO: 52           moltype = AA   length = 6
FEATURE                 Location/Qualifiers
REGION                  1..6
                        note = Synthetic Construct
MOD_RES                 4
                        note = Xaa = Aminoisobutyric acid
source                  1..6
                        mol_type = protein
                        organism = synthetic construct
SEQUENCE: 52
LIAXEA                                                                        6

SEQ ID NO: 53           moltype = AA   length = 6
FEATURE                 Location/Qualifiers
REGION                  1..6
                        note = Synthetic Construct
MOD_RES                 4
                        note = Xaa = D-Glutamic acid
source                  1..6
                        mol_type = protein
                        organism = synthetic construct
SEQUENCE: 53
LIAXAK                                                                        6

SEQ ID NO: 54           moltype = AA   length = 7
FEATURE                 Location/Qualifiers
REGION                  1..7
                        note = Synthetic Construct
source                  1..7
                        mol_type = protein
                        organism = synthetic construct
SEQUENCE: 54
LIADEAK                                                                       7

SEQ ID NO: 55           moltype = AA   length = 6
FEATURE                 Location/Qualifiers
REGION                  1..6
                        note = Synthetic Construct
source                  1..6
                        mol_type = protein
                        organism = synthetic construct
SEQUENCE: 55
LIAEAA                                                                        6

SEQ ID NO: 56           moltype = AA   length = 6
FEATURE                 Location/Qualifiers
REGION                  1..6
                        note = Synthetic Construct
source                  1..6
                        mol_type = protein
                        organism = synthetic construct
SEQUENCE: 56
LIAEAK                                                                        6

SEQ ID NO: 57           moltype = AA   length = 6
FEATURE                 Location/Qualifiers
REGION                  1..6
                        note = Synthetic Construct
```

```
source                       1..6
                             mol_type = protein
                             organism = synthetic construct
SEQUENCE: 57
LIAGEG                                                                   6

SEQ ID NO: 58                moltype = AA   length = 6
FEATURE                      Location/Qualifiers
REGION                       1..6
                             note = Synthetic Construct
source                       1..6
                             mol_type = protein
                             organism = synthetic construct
SEQUENCE: 58
LIAGGE                                                                   6

SEQ ID NO: 59                moltype = AA   length = 6
FEATURE                      Location/Qualifiers
REGION                       1..6
                             note = Synthetic Construct
source                       1..6
                             mol_type = protein
                             organism = synthetic construct
SEQUENCE: 59
LIAKGK                                                                   6

SEQ ID NO: 60                moltype = AA   length = 6
FEATURE                      Location/Qualifiers
REGION                       1..6
                             note = Synthetic Construct
source                       1..6
                             mol_type = protein
                             organism = synthetic construct
SEQUENCE: 60
LIANAK                                                                   6

SEQ ID NO: 61                moltype = AA   length = 6
FEATURE                      Location/Qualifiers
REGION                       1..6
                             note = Synthetic Construct
source                       1..6
                             mol_type = protein
                             organism = synthetic construct
SEQUENCE: 61
LIAPEA                                                                   6

SEQ ID NO: 62                moltype = AA   length = 6
FEATURE                      Location/Qualifiers
REGION                       1..6
                             note = Synthetic Construct
MOD_RES                      5
                             note = Xaa = Hydroxyproline
source                       1..6
                             mol_type = protein
                             organism = synthetic construct
SEQUENCE: 62
LIAPXA                                                                   6

SEQ ID NO: 63                moltype = AA   length = 6
FEATURE                      Location/Qualifiers
REGION                       1..6
                             note = Synthetic Construct
source                       1..6
                             mol_type = protein
                             organism = synthetic construct
SEQUENCE: 63
LIAQAK                                                                   6

SEQ ID NO: 64                moltype = AA   length = 8
FEATURE                      Location/Qualifiers
REGION                       1..8
                             note = Synthetic Construct
MOD_RES                      7
                             note = Xaa = beta-Alanine
source                       1..8
                             mol_type = protein
                             organism = synthetic construct
SEQUENCE: 64
IWGLDGXK                                                                 8
```

```
SEQ ID NO: 65            moltype = AA  length = 6
FEATURE                  Location/Qualifiers
REGION                   1..6
                         note = Synthetic Construct
MOD_RES                  4
                         note = Xaa = Aminoisobutyric acid
source                   1..6
                         mol_type = protein
                         organism = synthetic construct
SEQUENCE: 65
LIAXEA                                                                   6

SEQ ID NO: 66            moltype = AA  length = 7
FEATURE                  Location/Qualifiers
REGION                   1..7
                         note = Synthetic Construct
MOD_RES                  5
                         note = Xaa = D-Glutamic acid
source                   1..7
                         mol_type = protein
                         organism = synthetic construct
SEQUENCE: 66
LIAPXAK                                                                  7

SEQ ID NO: 67            moltype = AA  length = 6
FEATURE                  Location/Qualifiers
REGION                   1..6
                         note = Synthetic Construct
MOD_RES                  3
                         note = Xaa = Hydroxyproline
source                   1..6
                         mol_type = protein
                         organism = synthetic construct
SEQUENCE: 67
LIXEAK                                                                   6

SEQ ID NO: 68            moltype = AA  length = 8
FEATURE                  Location/Qualifiers
REGION                   1..8
                         note = Synthetic Construct
MOD_RES                  7
                         note = Xaa = beta-Alanine
source                   1..8
                         mol_type = protein
                         organism = synthetic construct
SEQUENCE: 68
WIALEGXK                                                                 8

SEQ ID NO: 69            moltype = AA  length = 6
FEATURE                  Location/Qualifiers
REGION                   1..6
                         note = Synthetic Construct
MOD_RES                  5
                         note = Xaa = D-Glutamic acid
source                   1..6
                         mol_type = protein
                         organism = synthetic construct
SEQUENCE: 69
FIAPXA                                                                   6

SEQ ID NO: 70            moltype = AA  length = 7
FEATURE                  Location/Qualifiers
REGION                   1..7
                         note = Synthetic Construct
source                   1..7
                         mol_type = protein
                         organism = synthetic construct
SEQUENCE: 70
ANVAENA                                                                  7

SEQ ID NO: 71            moltype = AA  length = 6
FEATURE                  Location/Qualifiers
REGION                   1..6
                         note = Synthetic Construct
source                   1..6
                         mol_type = protein
                         organism = synthetic construct
SEQUENCE: 71
```

```
LIAEAK                                                                          6

SEQ ID NO: 72            moltype = AA  length = 6
FEATURE                  Location/Qualifiers
REGION                   1..6
                         note = Synthetic Construct
source                   1..6
                         mol_type = protein
                         organism = synthetic construct
SEQUENCE: 72
LIAPEA                                                                          6

SEQ ID NO: 73            moltype = AA  length = 6
FEATURE                  Location/Qualifiers
REGION                   1..6
                         note = Synthetic Construct
VARIANT                  2
                         note = Xaa = Any Amino Acid
source                   1..6
                         mol_type = protein
                         organism = synthetic construct
SEQUENCE: 73
LXAEAK                                                                          6

SEQ ID NO: 74            moltype = AA  length = 6
FEATURE                  Location/Qualifiers
REGION                   1..6
                         note = Synthetic Construct
VARIANT                  3
                         note = Xaa = Any Amino Acid
source                   1..6
                         mol_type = protein
                         organism = synthetic construct
SEQUENCE: 74
LIXEAK                                                                          6

SEQ ID NO: 75            moltype = AA  length = 6
FEATURE                  Location/Qualifiers
REGION                   1..6
                         note = Synthetic Construct
VARIANT                  2
                         note = Xaa = Any Amino Acid
source                   1..6
                         mol_type = protein
                         organism = synthetic construct
SEQUENCE: 75
LXAEAK                                                                          6

SEQ ID NO: 76            moltype = AA  length = 7
FEATURE                  Location/Qualifiers
REGION                   1..7
                         note = Synthetic Construct
source                   1..7
                         mol_type = protein
                         organism = synthetic construct
SEQUENCE: 76
GGQIANI                                                                         7

SEQ ID NO: 77            moltype = AA  length = 6
FEATURE                  Location/Qualifiers
REGION                   1..6
                         note = Synthetic Construct
source                   1..6
                         mol_type = protein
                         organism = synthetic construct
SEQUENCE: 77
EGIAGK                                                                          6

SEQ ID NO: 78            moltype = AA  length = 6
FEATURE                  Location/Qualifiers
REGION                   1..6
                         note = Synthetic Construct
source                   1..6
                         mol_type = protein
                         organism = synthetic construct
SEQUENCE: 78
LIADAK                                                                          6

SEQ ID NO: 79            moltype = AA  length = 6
```

```
FEATURE              Location/Qualifiers
REGION               1..6
                     note = Synthetic Construct
source               1..6
                     mol_type = protein
                     organism = synthetic construct
SEQUENCE: 79
LIANAK                                                                          6

SEQ ID NO: 80        moltype = AA   length = 6
FEATURE              Location/Qualifiers
REGION               1..6
                     note = Synthetic Construct
source               1..6
                     mol_type = protein
                     organism = synthetic construct
SEQUENCE: 80
LIAEAA                                                                          6

SEQ ID NO: 81        moltype = AA   length = 6
FEATURE              Location/Qualifiers
REGION               1..6
                     note = Synthetic Construct
source               1..6
                     mol_type = protein
                     organism = synthetic construct
SEQUENCE: 81
LIAQAK                                                                          6

SEQ ID NO: 82        moltype = AA   length = 6
FEATURE              Location/Qualifiers
REGION               1..6
                     note = Synthetic Construct
source               1..6
                     mol_type = protein
                     organism = synthetic construct
SEQUENCE: 82
LIAGGE                                                                          6

SEQ ID NO: 83        moltype = AA   length = 6
FEATURE              Location/Qualifiers
REGION               1..6
                     note = Synthetic Construct
source               1..6
                     mol_type = protein
                     organism = synthetic construct
SEQUENCE: 83
LIAGEG                                                                          6

SEQ ID NO: 84        moltype = AA   length = 6
FEATURE              Location/Qualifiers
REGION               1..6
                     note = Synthetic Construct
source               1..6
                     mol_type = protein
                     organism = synthetic construct
SEQUENCE: 84
ANVAEK                                                                          6

SEQ ID NO: 85        moltype = AA   length = 6
FEATURE              Location/Qualifiers
REGION               1..6
                     note = Synthetic Construct
source               1..6
                     mol_type = protein
                     organism = synthetic construct
SEQUENCE: 85
LIAKGK                                                                          6

SEQ ID NO: 86        moltype = AA   length = 15
FEATURE              Location/Qualifiers
REGION               1..15
                     note = Synthetic Construct
source               1..15
                     mol_type = protein
                     organism = synthetic construct
SEQUENCE: 86
GTPGPQGIAG QRGVV                                                               15
```

```
SEQ ID NO: 87           moltype = AA  length = 6
FEATURE                 Location/Qualifiers
REGION                  1..6
                        note = Synthetic Construct
VARIANT                 2
                        note = Xaa = Any Amino Acid
source                  1..6
                        mol_type = protein
                        organism = synthetic construct
SEQUENCE: 87
IXAEAK                                                                      6

SEQ ID NO: 88           moltype = AA  length = 6
FEATURE                 Location/Qualifiers
REGION                  1..6
                        note = Synthetic Construct
VARIANT                 2
                        note = Xaa = Any Amino Acid
source                  1..6
                        mol_type = protein
                        organism = synthetic construct
SEQUENCE: 88
LXAEAK                                                                      6

SEQ ID NO: 89           moltype = AA  length = 6
FEATURE                 Location/Qualifiers
REGION                  1..6
                        note = Synthetic Construct
source                  1..6
                        mol_type = protein
                        organism = synthetic construct
SEQUENCE: 89
LPAEAK                                                                      6

SEQ ID NO: 90           moltype = AA  length = 6
FEATURE                 Location/Qualifiers
REGION                  1..6
                        note = Synthetic Construct
source                  1..6
                        mol_type = protein
                        organism = synthetic construct
SEQUENCE: 90
LIPEAK                                                                      6

SEQ ID NO: 91           moltype = AA  length = 6
FEATURE                 Location/Qualifiers
REGION                  1..6
                        note = Synthetic Construct
VARIANT                 3
                        note = Xaa = Any Amino Acid
source                  1..6
                        mol_type = protein
                        organism = synthetic construct
SEQUENCE: 91
LIXEAK                                                                      6

SEQ ID NO: 92           moltype = AA  length = 6
FEATURE                 Location/Qualifiers
REGION                  1..6
                        note = Synthetic Construct
VARIANT                 4
                        note = Xaa = Any Amino Acid
source                  1..6
                        mol_type = protein
                        organism = synthetic construct
SEQUENCE: 92
LIAXEA                                                                      6

SEQ ID NO: 93           moltype = AA  length = 8
FEATURE                 Location/Qualifiers
REGION                  1..8
                        note = Synthetic Construct
VARIANT                 7
                        note = Xaa = Any Amino Acid
source                  1..8
                        mol_type = protein
                        organism = synthetic construct
SEQUENCE: 93
IWGLDGXK                                                                    8
```

-continued

```
SEQ ID NO: 94          moltype = AA  length = 8
FEATURE                Location/Qualifiers
REGION                 1..8
                       note = Synthetic Construct
VARIANT                7
                       note = Xaa = Any Amino Acid
source                 1..8
                       mol_type = protein
                       organism = synthetic construct
SEQUENCE: 94
WIALEGXK                                                                    8

SEQ ID NO: 95          moltype = AA  length = 9
FEATURE                Location/Qualifiers
REGION                 1..9
                       note = Synthetic Construct
source                 1..9
                       mol_type = protein
                       organism = synthetic construct
SEQUENCE: 95
GPQGIAGQR                                                                   9

SEQ ID NO: 96          moltype = AA  length = 6
FEATURE                Location/Qualifiers
REGION                 1..6
                       note = Synthetic Construct
source                 1..6
                       mol_type = protein
                       organism = synthetic construct
SEQUENCE: 96
QGIAGQ                                                                      6

SEQ ID NO: 97          moltype = AA  length = 7
FEATURE                Location/Qualifiers
REGION                 1..7
                       note = Synthetic Construct
source                 1..7
                       mol_type = protein
                       organism = synthetic construct
SEQUENCE: 97
QGIAGQR                                                                     7

SEQ ID NO: 98          moltype = AA  length = 6
FEATURE                Location/Qualifiers
REGION                 1..6
                       note = Synthetic Construct
source                 1..6
                       mol_type = protein
                       organism = synthetic construct
SEQUENCE: 98
FGIAGF                                                                      6

SEQ ID NO: 99          moltype = AA  length = 5
FEATURE                Location/Qualifiers
REGION                 1..5
                       note = Synthetic Construct
source                 1..5
                       mol_type = protein
                       organism = synthetic construct
SEQUENCE: 99
GIAGQ                                                                       5

SEQ ID NO: 100         moltype = AA  length = 6
FEATURE                Location/Qualifiers
REGION                 1..6
                       note = Synthetic Construct
source                 1..6
                       mol_type = protein
                       organism = synthetic construct
SEQUENCE: 100
QGAIAQ                                                                      6

SEQ ID NO: 101         moltype = AA  length = 6
FEATURE                Location/Qualifiers
REGION                 1..6
                       note = Synthetic Construct
source                 1..6
                       mol_type = protein
```

```
                        organism = synthetic construct
SEQUENCE: 101
FGIAGF                                                                          6

SEQ ID NO: 102          moltype = AA   length = 6
FEATURE                 Location/Qualifiers
REGION                  1..6
                        note = Synthetic Construct
source                  1..6
                        mol_type = protein
                        organism = synthetic construct
SEQUENCE: 102
CGIAGC                                                                          6

SEQ ID NO: 103          moltype = AA   length = 6
FEATURE                 Location/Qualifiers
REGION                  1..6
                        note = Synthetic Construct
source                  1..6
                        mol_type = protein
                        organism = synthetic construct
SEQUENCE: 103
EGIAGK                                                                          6

SEQ ID NO: 104          moltype =    length =
SEQUENCE: 104
000

SEQ ID NO: 105          moltype =    length =
SEQUENCE: 105
000

SEQ ID NO: 106          moltype =    length =
SEQUENCE: 106
000

SEQ ID NO: 107          moltype = AA   length = 6
FEATURE                 Location/Qualifiers
REGION                  1..6
                        note = Synthetic Construct
VARIANT                 3
                        note = Xaa = Any Amino Acid
source                  1..6
                        mol_type = protein
                        organism = synthetic construct
SEQUENCE: 107
IIXEAK                                                                          6

SEQ ID NO: 108          moltype = AA   length = 6
FEATURE                 Location/Qualifiers
REGION                  1..6
                        note = Synthetic Construct
VARIANT                 3
                        note = Xaa = Any Amino Acid
source                  1..6
                        mol_type = protein
                        organism = synthetic construct
SEQUENCE: 108
LIXEAK                                                                          6

SEQ ID NO: 109          moltype = AA   length = 6
FEATURE                 Location/Qualifiers
REGION                  1..6
                        note = Synthetic Construct
VARIANT                 4
                        note = Xaa = Any Amino Acid
source                  1..6
                        mol_type = protein
                        organism = synthetic construct
SEQUENCE: 109
LIAXAK                                                                          6

SEQ ID NO: 110          moltype = AA   length = 6
FEATURE                 Location/Qualifiers
REGION                  1..6
                        note = Synthetic Construct
VARIANT                 5
                        note = Xaa = Any Amino Acid
source                  1..6
```

```
                        mol_type = protein
                        organism = synthetic construct
SEQUENCE: 110
LIAPXA                                                              6

SEQ ID NO: 111          moltype = AA  length = 6
FEATURE                 Location/Qualifiers
REGION                  1..6
                        note = Synthetic Construct
VARIANT                 4
                        note = Xaa = Any Amino Acid
source                  1..6
                        mol_type = protein
                        organism = synthetic construct
SEQUENCE: 111
LIAXAK                                                              6

SEQ ID NO: 112          moltype = AA  length = 4
FEATURE                 Location/Qualifiers
REGION                  1..4
                        note = Synthetic Construct
source                  1..4
                        mol_type = protein
                        organism = synthetic construct
SEQUENCE: 112
LIAE                                                                4

SEQ ID NO: 113          moltype = AA  length = 4
FEATURE                 Location/Qualifiers
REGION                  1..4
                        note = Synthetic Construct
source                  1..4
                        mol_type = protein
                        organism = synthetic construct
SEQUENCE: 113
NVAE                                                                4

SEQ ID NO: 114          moltype = AA  length = 6
FEATURE                 Location/Qualifiers
REGION                  1..6
                        note = Synthetic Construct
MOD_RES                 4
                        note = Xaa = D-Glutamic acid
source                  1..6
                        mol_type = protein
                        organism = synthetic construct
SEQUENCE: 114
NVAXNA                                                              6

SEQ ID NO: 115          moltype = AA  length = 7
FEATURE                 Location/Qualifiers
REGION                  1..7
                        note = Synthetic Construct
MOD_RES                 5
                        note = Xaa = D-Glutamic acid
source                  1..7
                        mol_type = protein
                        organism = synthetic construct
SEQUENCE: 115
ANVAXNA                                                             7
```

What is claimed is:

1. A method of treating pain in a patient in need thereof, comprising administering to the patient a composition comprising a therapeutically effective amount of one or more peptides which inhibit the activity of NF κB selected from the group consisting of peptides of six to eight amino acid residues in length, wherein the one or more peptides are selected from the group consisting of peptides of:

CORE SEQUENCE (1): Xxx-Ala-Pro-Glu
where Xxx is selected from the group consisting of Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, a-Amino-1-naphthalenepropanoic acid, β-cyclohexyl-Ala, dehydroalanine, and β-tert-butyl-Ala;

CORE SEQUENCE (2): Xxx-Ala-Pro-D-Glu
where Xxx is selected from the group consisting of Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala;

CORE SEQUENCE (3): Xxx-Ala-Glu-Ala
where Xxx is selected from the group consisting of Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala;

CORE SEQUENCE (4): Xxx-Ala-D-Glu-Ala
where Xxx is selected from the group consisting of Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala;

CORE SEQUENCE (5): Xxx-Ala-Asn-Ala
where Xxx is selected from the group consisting of Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala;

CORE SEQUENCE (6): Xxx-Ala-D-Asn-Ala
where Xxx is selected from the group consisting of Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala;

CORE SEQUENCE (7): Xxx-Ala-Glu-Asn
where Xxx is selected from the group consisting of Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala;

CORE SEQUENCE (8): Xxx-Ala-D-Glu-Asn
where Xxx is selected from the group consisting of Met, Ile, Val, Cys, Trp, Tyr, Phe, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala;

and SEQ ID NOS: 001-007, 010, 011, 013-029, and 031-040;
wherein the one or more peptides exclude peptides comprising the sequence LWAEAK (SEQ ID NO:008), peptides comprising the sequence LIAEAK (SEQ ID NO:009), peptides comprising the sequence LVAEAK (SEQ ID NO:030), peptides comprising the sequence LIANAK (SEQ ID NO:012), and peptides comprising SEQ ID NOS: 041-113.

2. A method of treating pain in a patient in need thereof, comprising administering to the patient a composition comprising a therapeutically effective amount of one or more peptides which inhibit the activity of NF κB selected from the group consisting of peptides of six to eight amino acid residues in length, wherein the peptide comprises the sequence:
Xxx-Ala-Pro-D-Glu (CORE SEQUENCE (2)),
where Xxx is selected from the group consisting of Cys, Trp, 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala.

3. The method of claim 1, wherein the composition further comprises a pharmaceutically acceptable carrier.

4. The method of claim 2, wherein the composition further comprises a pharmaceutically acceptable carrier.

5. The method of claim 1, wherein Xxx is selected from the group consisting of Cys and Trp.

6. The method of claim 2, wherein Xxx is selected from the group consisting of Cys and Trp.

7. The method of claim 1, wherein Xxx is selected from the group consisting of 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala.

8. The method of claim 2, wherein Xxx is selected from the group consisting of 5-methyl-Trp, allo-Ile, β-styryl-Ala, naphthyl-Ala, diphenyl-Ala, α-aminobutyric acid, α-aminocaproic acid, norleucine, α-amino-2-phenylbutyric acid, α-Amino-1-naphthalenepropanoic acid, β-cyclohexyl-Ala, dehydroalanine, and β-tert-butyl-Ala.

9. The method of claim 2, wherein the peptide is selected from the group consisting of peptides of six to eight amino acid residues in length comprising the sequence:
AWAP[D]EA (SEQ ID NO:025).

10. The method of claim 2, wherein the peptide is AWAP[D]EA (SEQ ID NO:025).

11. The method of claim 1, wherein the composition comprising one or more peptides is formulated as an emulsion, paste, spray, cream, or lotion.

12. The method of claim 2, wherein the composition comprising one or more peptides is formulated as an emulsion, paste, spray, cream, or lotion.

13. The method of claim 1, wherein the composition comprising one or more peptides is formulated for subcutaneous administration.

14. The method of claim 2, wherein the composition comprising one or more peptides is formulated for subcutaneous administration.

15. The method of claim 1, wherein the composition comprising one or more peptides is formulated for intravenous administration.

16. The method of claim 2, wherein the composition comprising one or more peptides is formulated for intravenous administration.

17. The method of claim 1, wherein the composition comprising one or more peptides is formulated as a sterile formulation.

18. The method of claim 2, wherein the composition comprising one or more peptides is formulated as a sterile formulation.

19. The method of claim 1, wherein the administering to the patient comprises topical application on or near the affected area.

20. The method of claim 1, wherein the administering to the patient comprises subcutaneous administration to or near the affected area.

21. The method of claim 1, wherein the administering to the patient comprises intravenous administration.

* * * * *